US012709640B2

(12) United States Patent
Schiros et al.

(10) Patent No.: US 12,709,640 B2
(45) Date of Patent: Aug. 18, 2026

(54) BIODEGRADABLE TEXTILE FIBERS WITH INHERENT COLOR AND PROPERTIES

(71) Applicant: The Trustees of Columbia University in the City of New York, New York, NY (US)

(72) Inventors: Theanne Schiros, New York, NY (US); Chui Lian Lee, Brooklyn, NY (US); Valentina Gomez, Brooklyn, NY (US); Morgana Katterman, New York, NY (US); Helen H. Lu, New York, NY (US); Allie Obermeyer, New York, NY (US); Philip Brudnicki, New York, NY (US); Sebastian S. Cocioba, Long Island City, NY (US); Christopher Z. Mosher, New York, NY (US); Romare M. Antrobus, New York, NY (US); Yuncan Zhu, San Diego, CA (US); Aditi Sharma, Providence, RI (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 702 days.

(21) Appl. No.: 17/914,139

(22) PCT Filed: Mar. 24, 2021

(86) PCT No.: PCT/US2021/023947

§ 371 (c)(1),
(2) Date: Sep. 23, 2022

(87) PCT Pub. No.: WO2021/195257

PCT Pub. Date: Sep. 30, 2021

(65) Prior Publication Data

US 2023/0322902 A1 Oct. 12, 2023

Related U.S. Application Data

(60) Provisional application No. 62/994,263, filed on Mar. 24, 2020.

(51) Int. Cl.

| | |
|---|---|
| ***C07K 14/78*** | (2006.01) |
| ***C07K 14/435*** | (2006.01) |
| ***C09K 11/06*** | (2006.01) |
| ***C12N 9/10*** | (2006.01) |
| ***D01F 4/00*** | (2006.01) |

(52) U.S. Cl.

CPC ........ *C07K 14/78* (2013.01); *C07K 14/43595* (2013.01); *C09K 11/06* (2013.01); *C12N 9/1044* (2013.01); *C12Y 203/02013* (2013.01); *D01F 4/00* (2013.01); *C09K 2211/1466* (2013.01); *D10B 2401/12* (2013.01)

(58) Field of Classification Search

CPC ...... C07K 14/78; C07K 14/435; C09K 11/06; C12N 9/10

See application file for complete search history.

(56) References Cited

U.S. PATENT DOCUMENTS

2018/0193524 A1 7/2018 Shoseyov

FOREIGN PATENT DOCUMENTS

| | | | |
|---|---|---|---|
| JP | H05295005 | 11/1993 | |
| JP | 2002-507410 | 3/2002 | |
| KR | 20150140916 A | 12/2015 | |
| WO | WO-2019213155 A1 * | 11/2019 | ........... A23C 11/106 |

OTHER PUBLICATIONS

Chambi et al., "Mechanical and water vapor permeability properties of biodegradables films based on methylcellulose glucomannan, pectin and gelatin." Food Science and Technology. Sep. 2011, vol. 31, No. 3, pp. 739-746.

Cherian et al., "Cellulose nanocomposites with nanofibers isolated from pineapple leaf fibers for medical applications." Carbohydrate Polymers. Oct. 15, 2011, vol. 86, No. 4, pp. 1790-1798.

International Search Report issued Jun. 30, 2021 in connection with PCT International Application No. PCT/US2021/023947, filed Mar. 24, 2021.

Notification of Transmittal of the International Search Report and the Written Opinion of the International Searching Authority, or the Declaration Jun. 30, 2021 in connection with PCT International Application No. PCT/US2021/023947, filed Mar. 24, 2021.

Written Opinion of the International Searching Authority issued Jun. 30, 2021 in connection with PCT International Application No. PCT/US2021/023947, filed Mar. 24, 2021.

Feb. 15, 2024 Canadian Office Action issued in connection with Canadian Application No. 3,172,177.

May 31, 2024 Extended European Search Report issued in connection with European Application No. 91776926.4.

International Preliminary Report on Patentability issued Oct. 6, 2022, in connection with PCT International Application No. PCT/US2021/023947.

Japanese Office Action issued Mar. 4, 2025 in connection with Japanese Application No. 2022-557883, including English-language translation.

(Continued)

*Primary Examiner* — Tekchand Saidha

(57) ABSTRACT

A biopolymer composition can be formed based, at least in part, on a recombinantly expressed protein, expressed from a DNA coding sequence of a source protein, and the recombinantly expressed protein can optionally comprise one or more tags that enhance the crosslinking capacity of the protein. It was determined that such biopolymer composition can be suitable for use to obtain, for example, a biodegradable textile that exhibits a functional characteristic associated with the recombinantly expressed protein.

18 Claims, 44 Drawing Sheets

(56) References Cited

OTHER PUBLICATIONS

A. Pinotti, M.A. García, M.N. Martino, N.E. Zaritzky, "Study on microstructure and physical properties of composite films based on chitosan and methylcellulose," Food Hydrocolloids, vol. 21, Issue 1, 2007, pp. 66-72, ISSN 0268-005X, DOI: 10.1016/j.foodhyd.2006.02.001.

Australian Examination Report No. 1 issued Nov. 4, 2025 in connection with Australian Application No. 2021242269.

European Communication pursuant to Article 94 (3) issued Nov. 3, 2025 in connection with European Application No. 21776926.4.

* cited by examiner

Fluorescent protein concentration lost to solution as a function of charge (+)

| Sample | Average |
|---|---|
| Blank | 0.000 |
| GFP 0 | 0.106 |
| GFP +6 | 0.043 |
| GFP +12 | 0.050 |
| GFP +24 | 0.106 |
| GFP +30 | 0.107 |

BIODEGRADABLE TEXTILE FIBERS WITH INHERENT COLOR AND PROPERTIES

CROSS-REFERENCE TO RELATED APPLICATIONS

This application is a § 371 national stage of PCT International Application No. PCT/US2021/023947, filed Mar. 24, 2021, claiming the benefit of U.S. Provisional Application No. 62/994,263, filed Mar. 24, 2020, the entire contents of each of which are hereby incorporated herein by reference.

This invention was made with government support under 1420634 awarded by the National Science Foundation. The government has certain rights in the invention.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

TECHNICAL FIELDS

This application relates to a biopolymer composition formed based, at least in part, on a recombinantly expressed protein, expressed from a DNA coding sequence (which may be optionally modified to comprise one or more tags that enhance the crosslinking capacity of the recombinantly expressed protein) of a source protein, and more specifically, such a biopolymer composition that is suitable for use to obtain, for example, a biodegradable textile. The biodegradable textile may be used to form products including, but not limited to, fabrics and knits for garments, interior uses, bandages, gauze, textile fibers for apparel, accessories, industrial applications, interiors, bioplastics and other purposes.

BACKGROUND

An increased public awareness of fashion's environmental impact is driving the industry towards sustainable business models. Several industry leaders are members of the Sustainable Apparel Coalition and Global Fashion Agenda, measuring their environmental and social labor impacts across the value chain in addition to working with policy makers to develop a wider framework for a circular fashion system. With an effort to reduce their environmental footprint, brands are actively seeking sustainable raw material alternatives to traditional fibers.

Traditional textile production heavily relies on petrochemicals, livestock, and agriculture—the largest industrial contributors to $CO_2$ emissions globally. The fashion industry is one of the biggest contributors to climate change, producing 1.2 billion tons of $CO_2$ emissions per year, and the single largest source of microplastic pollution globally (The price of fast fashion. Nature Clim Change, 8:1 (2018); DeFalco et al. *Scientific Reports* (2019) 9:6633). Indeed, machine washing of synthetic textiles is responsible for 23% of micro plastic pollution in the ocean.

The textile industry is also one of the most chemically intensive and ecotoxic industries on earth, and the second largest source of industrial water pollution after agriculture, both in terms of the volume generated and toxicity of effluents (Sen S, Demirer G N. Water Research 2003, 37 (8) 1868-1878; Ben Mansour H, et al. Environmental science and pollution research international (2012), DOI 10.1007/s11356-012-0802-7; Rita Kant, Natural *Science,* 4, 1(2012), 17027). Textile dyeing and finishing accounts for 20% of global water waste (R. Kirchain, et al. Sustainable Apparel Materials/Materials Systems Laboratory (2015)). As such, textile production, finishing and end of life impacts are a major threat to biodiversity, an ecosystem's greatest resilience to the impacts of climate change.

In an effort to reduce fashions environmental footprint, brands are actively seeking raw material alternatives to traditional fibers. With growing demand for sustainable raw materials, many alternatives have been introduced to the marketplace, including recycled PET, sustainably produced regenerated cellulosic fibers, recycled wool, and emerging biomaterials. However, many biomaterials still rely on conventional textile processes, which can be toxic and water intensive. Fiber alternatives, such as recycled polyester is heavily processed, relies on synthetic dyes, is not biodegradable, and releases microplastics.

BRIEF SUMMARY

In an approach to generate a biotextile material, a purified, recombinantly expressed protein is obtained, and the DNA coding sequence of the protein may optionally be modified to comprise one or more tags each increasing the crosslinking capacity of the protein. A transglutaminase may be employed as an enzyme to enhance crosslinking of the recombinantly expressed protein to another unit of recombinantly expressed protein or another constituent protein, in a biopolymer composition. As discussed, a biotextile material can be formed by employing such biopolymer composition including constituent proteins where crosslinking of the constituent proteins has been enhanced, and the biotextile material obtained in such manner can exhibit a functional characteristic associated with the recombinantly expressed protein. For example, the proteins may be enzymatically crosslinked into fibers or films, and the functional characteristic may be one or more of, e.g., stretch, rigidity, color, waterproofing, resilience, etc.

In an embodiment, the biotextile material may include or may be formed by a plurality of fibers, each having been formed by employing the biopolymer composition which includes the recombinantly expressed protein cross-linked to another unit of recombinantly expressed protein or another constituent protein. The tag added to the modified DNA coding sequence for the recombinantly expressed protein enhanced fiber formation.

In another embodiment, the biotextile material may include or may be formed by a plurality of films formed from the crosslinked composition, where the tag added to the modified DNA coding sequence for the recombinantly expressed protein enhanced film formation.

For example, the recombinantly expressed protein may be cross-linked to a gelatin protein forming a bulking material of the biotextile material. In another example, the recombinantly expressed protein is cross-linked to a cellulose protein or cellulose protein composite, the cellulose protein or cellulose protein composite forming a bulking material of the biotextile material. On the other hand, the recombinantly expressed protein may instead be cross-linked to said another unit of the recombinantly expressed protein, and a plurality of cross-linked units of the recombinantly expressed protein form a bulking material of the biotextile material.

In a method, according to another embodiment, to generate a biotextile material, a biopolymer composition comprising a purified source protein is obtained. Molecules of the source protein are crosslinked to each other or to another constituent of the biopolymer composition. A biotextile material can be generated from the crosslinked biopolymer composition, such that the biotextile material exhibit a functional characteristic associated with the purified source protein. For example, the proteins may be chemically or enzymatically crosslinked into fibers or films, and the functional characteristic may be one or more of, e.g., stretch, rigidity, color, waterproofing, resilience, etc.

BRIEF DESCRIPTION OF THE DRAWINGS

FIG. 13A: Fourier Transform Infrared Spectroscopy (FTIR) data for amide I and II of RFP and GFP immobilized in bacterial nanocellulose immersed in water for different time points. FIG. 13B: Fiber color stability in aqueous environment: Intensity of fluorescent protein resonance measured with UV-Vis after 24 hours in water. FIG. 13C: Biomaterial protein fibers, in which engineered proteins, including GFP (green) and RFP (pink) and enzymatically cross-linked to gelatin when extruded into a coagulation bath. FIG. 13D: Biomaterial ("Werewool") knit swatch with purple color produced by adding RFP to UV-sensitive blue FP (inset), enzymatically crosslinked with gelatin when extruded into a coagulation bath.

(FIG. 14A) concentration of protein incorporated into BNC; and (FIG. 14B) concentration of FP lost to solution after immersion of FP-BNC samples in distilled H2O for 24 hours. Data is expressed as average (n=5). FIG. 14C: Stability of GFP engineered with different end groups/charge as a function pH measured to inform fiber processing parameters, expressed as a percent of the UV-Vis absorption resonance for each protein. FIG. 14D: Stability of mCherry engineered with different end groups/charge as a function pH measured to inform fiber processing parameters, expressed as a percent of the UV-Vis absorption resonance for each protein. FIG. 14E: Photos of Werewool fibers with color from GFP (green) and MScarlet (pink) in a protein-polysaccharide composite (FP/whey/alginate) extruded into a $CaCl_2$) coagulation bath.

FIG. 15A: FTIR of soy protein isolate (SPI) and its primary globular subunits, 7S and 11S, enzymatically crosslinked by 1% TG in a coagulation bath or incorporated directly in the protein dope before casting films or extruding fibers. The right shift in Amide III in the 7S+TG dope group indicates a linear chemical structure for 7S. In contrast, 11S exhibits spectra conducive to aromatic chemical structures. SPI—subunit separation in 4% w/v $CaCl_2$):

7S = linear -

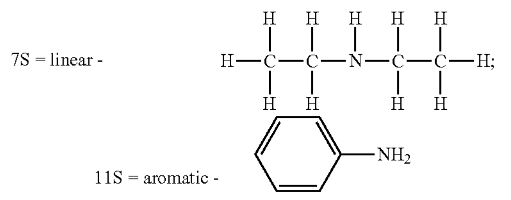

11S = aromatic -

Figure 15A:
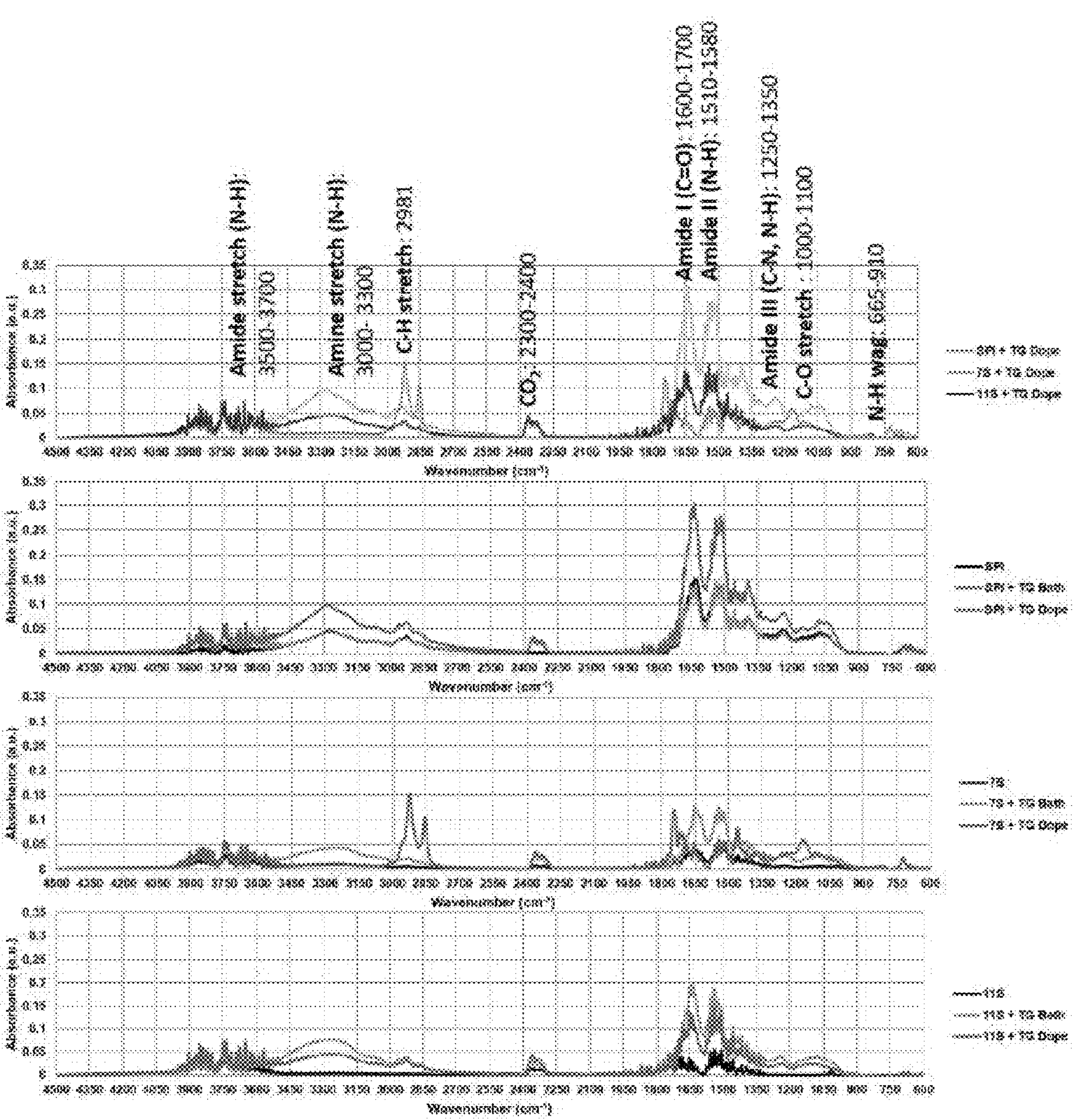
FIGS. 15A-15D: Chemical mechanism and spectral fingerprints of enzymatic cross-linking of proteins evaluated with Fourier Transform Infrared Spectroscopy (FTIR).
Figure 15B:
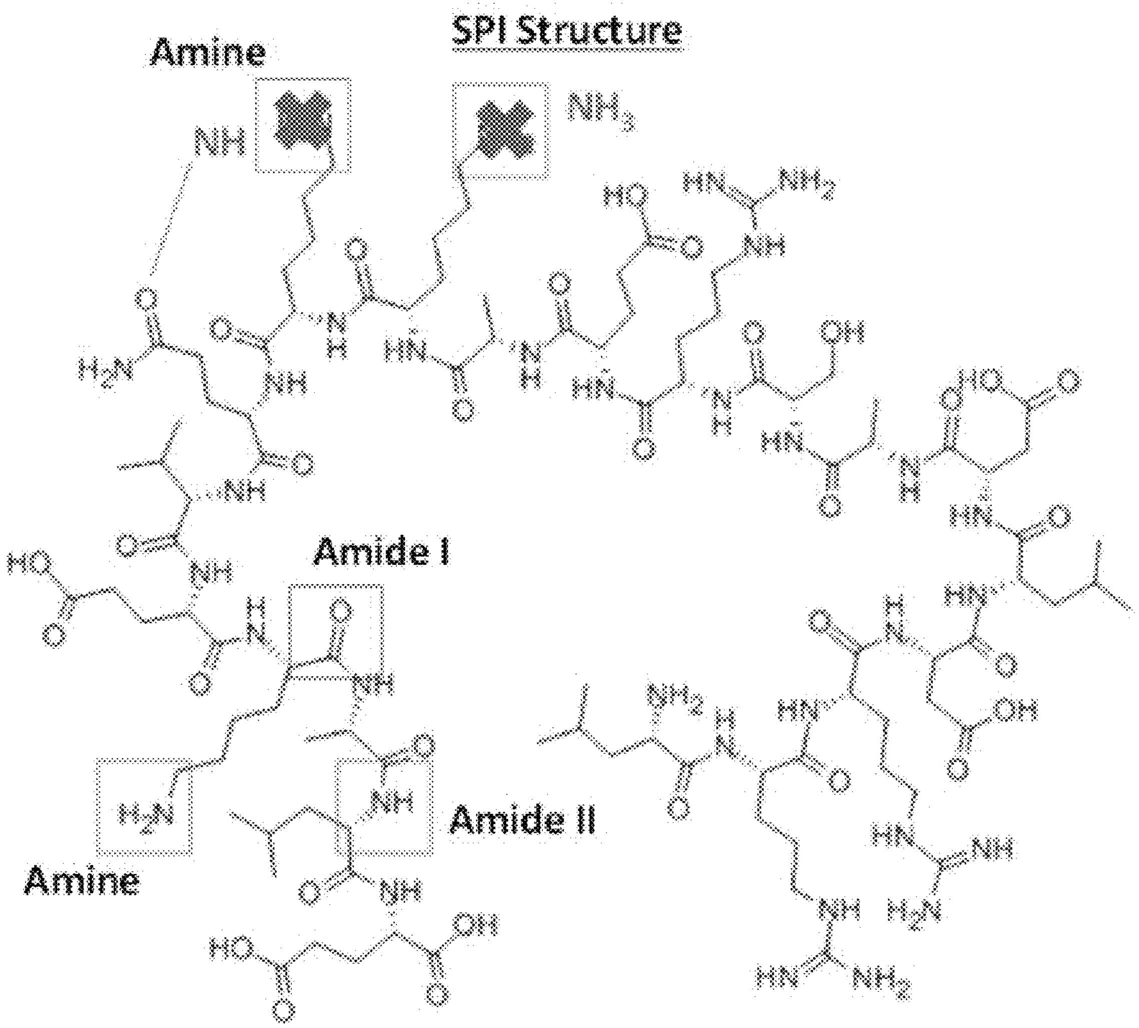
Figure 15C:
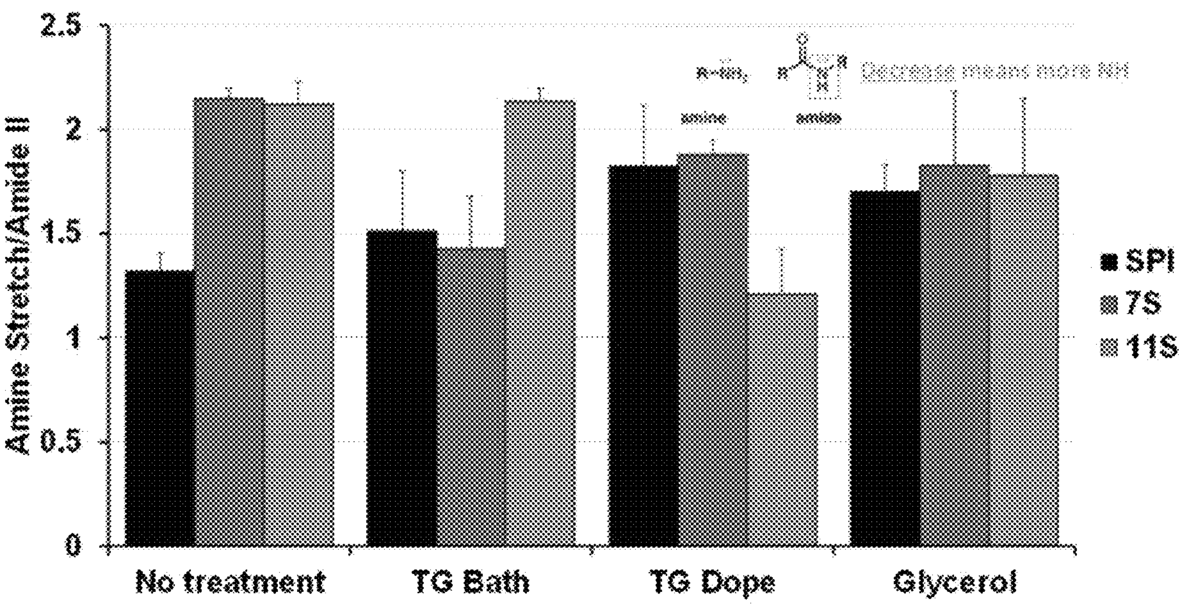
Figure 15D:
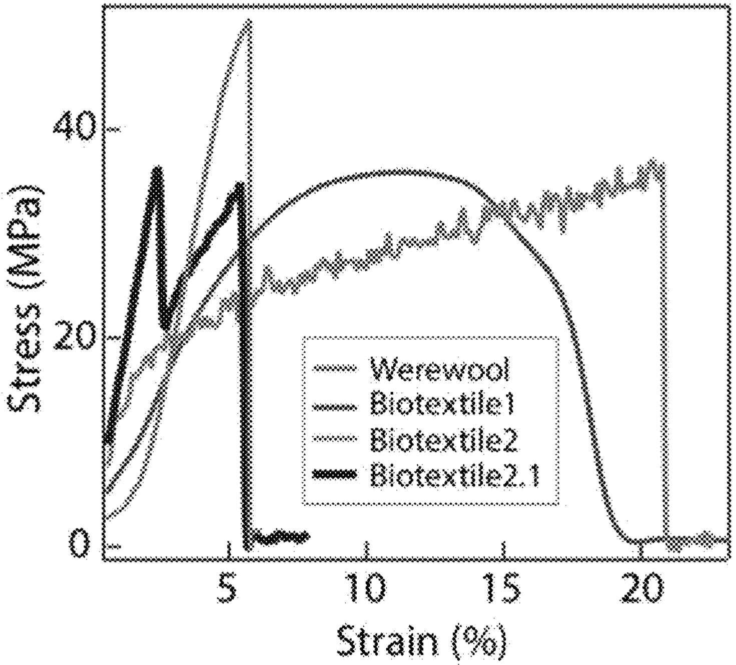

FIG. 15B: Soy protein isolate (SPI) structure and crosslinking mechanism via enzymatic catalysis of amines to amides in SPI films by transglutaminase (TG) in films and fibers. FIG. 15C: Evaluation of crosslinking with FTIR absorbance intensity. FIG. 15D: Mechanical testing of disclosed fibers (listed as "Werewool", see also FIG. 13B) compared with emerging biotextiles measured with a uniaxial tensile testing machine (Instron, Model 1321, Norwood, MA, USA), equipped with a 25 kN load cell.

Figure 16A:
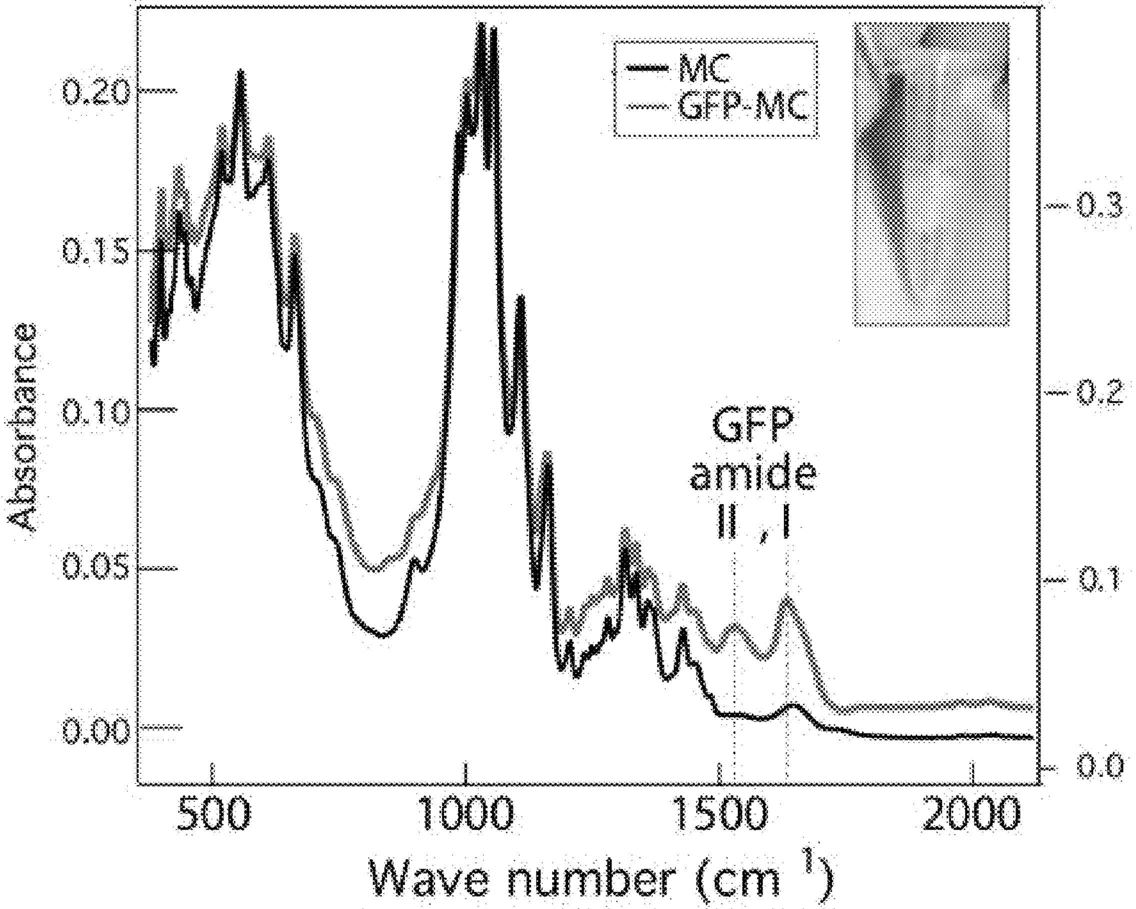
Figure 16B:
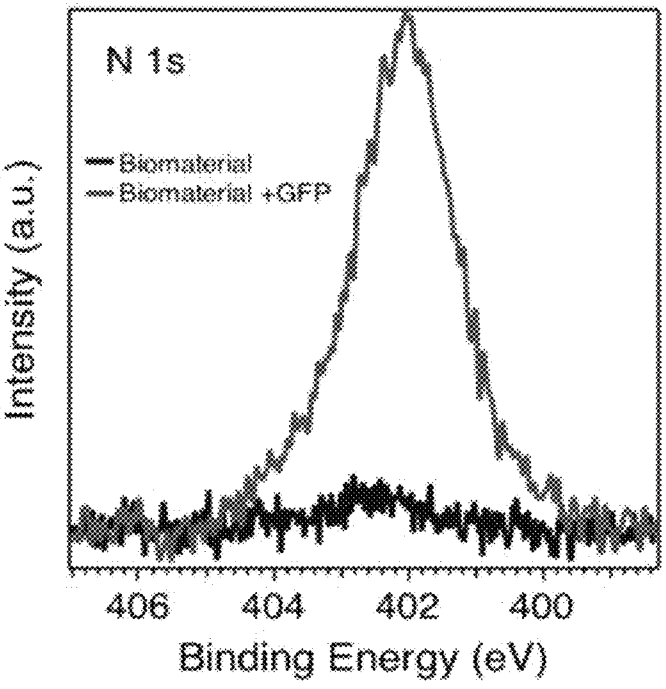
Figure 16C:
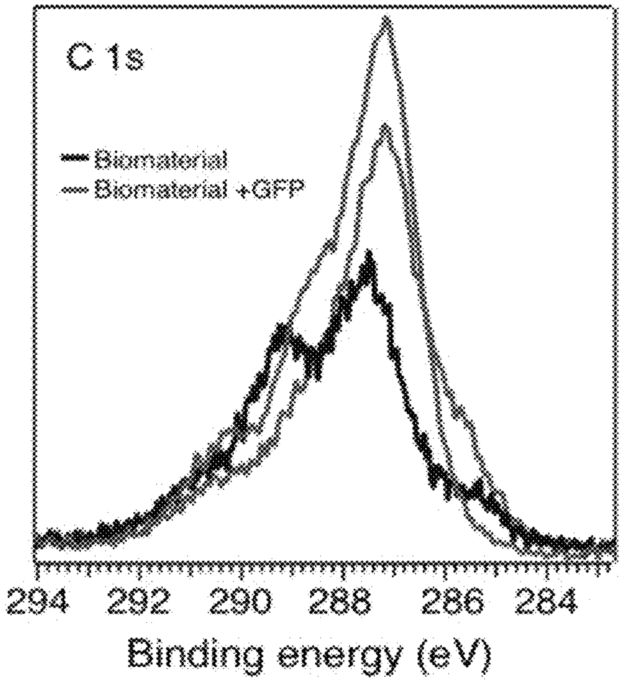

FIGS. 16A-16C: Molecular level analysis of efficacy of enzymatic linking for different proteins using Fourier Transform Infrared Spectroscopy (FTIR) and X-ray Photoelectron Spectroscopy (XPS). FIG. 16A: FTIR of BNC with color and amide peaks (green curve) indicating functionalization with GFP. Nitrogen (N Is) (FIG. 16B) and Carbon (C Is) (FIG. 16C) core level spectra of BNC with and without GFP measured using X-ray Photoelectron Spectroscopy (XPS). The increase in N 1*s* (FIG. 16B) and shift in intensity towards C≡N binding energy (C 1s, FIG. 16C) indicates functionalization of biopolymer with GFP, consistent with FTIR (FIG. 15A).

Figure 17A:
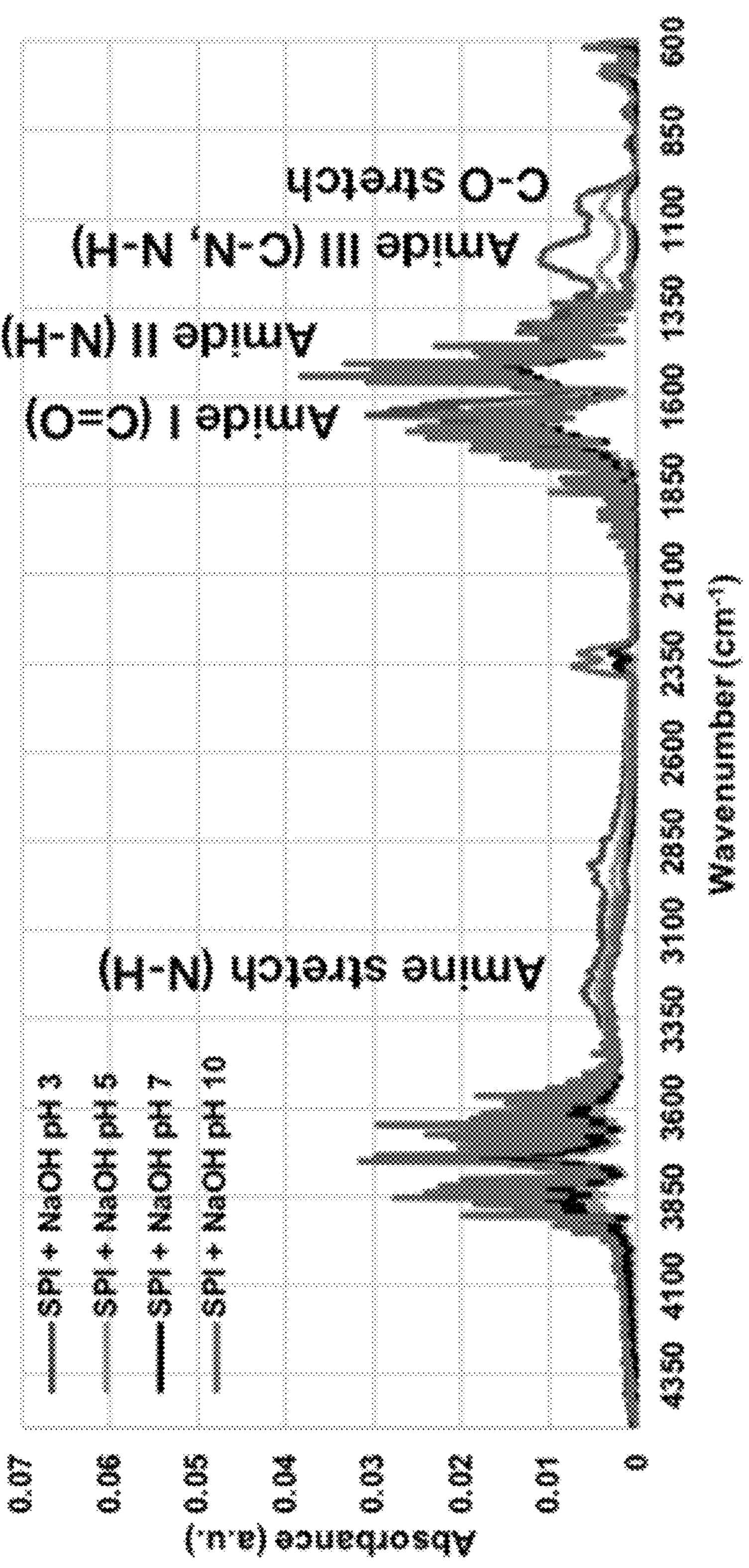
Figure 17B:
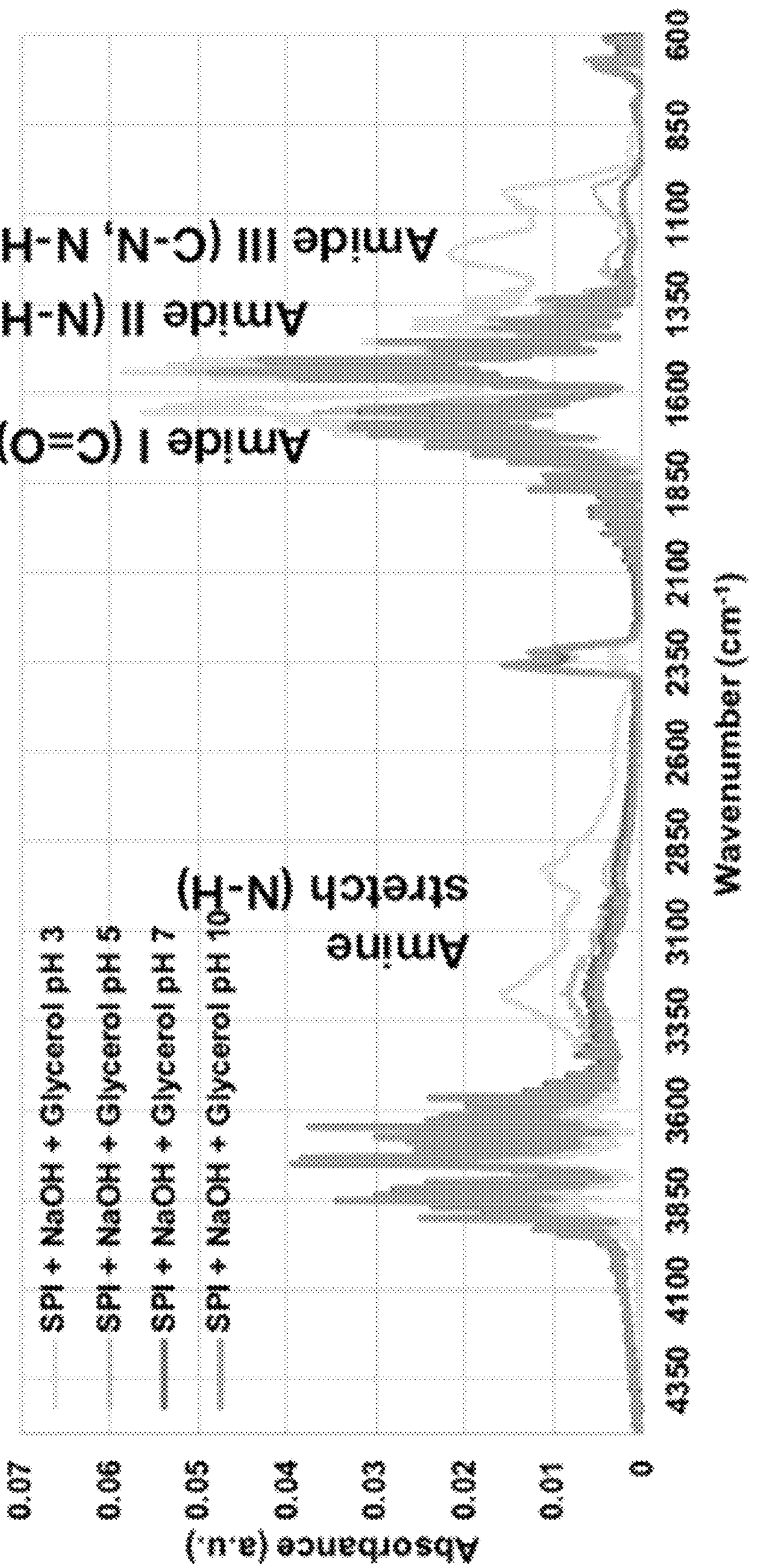
Figure 17C:
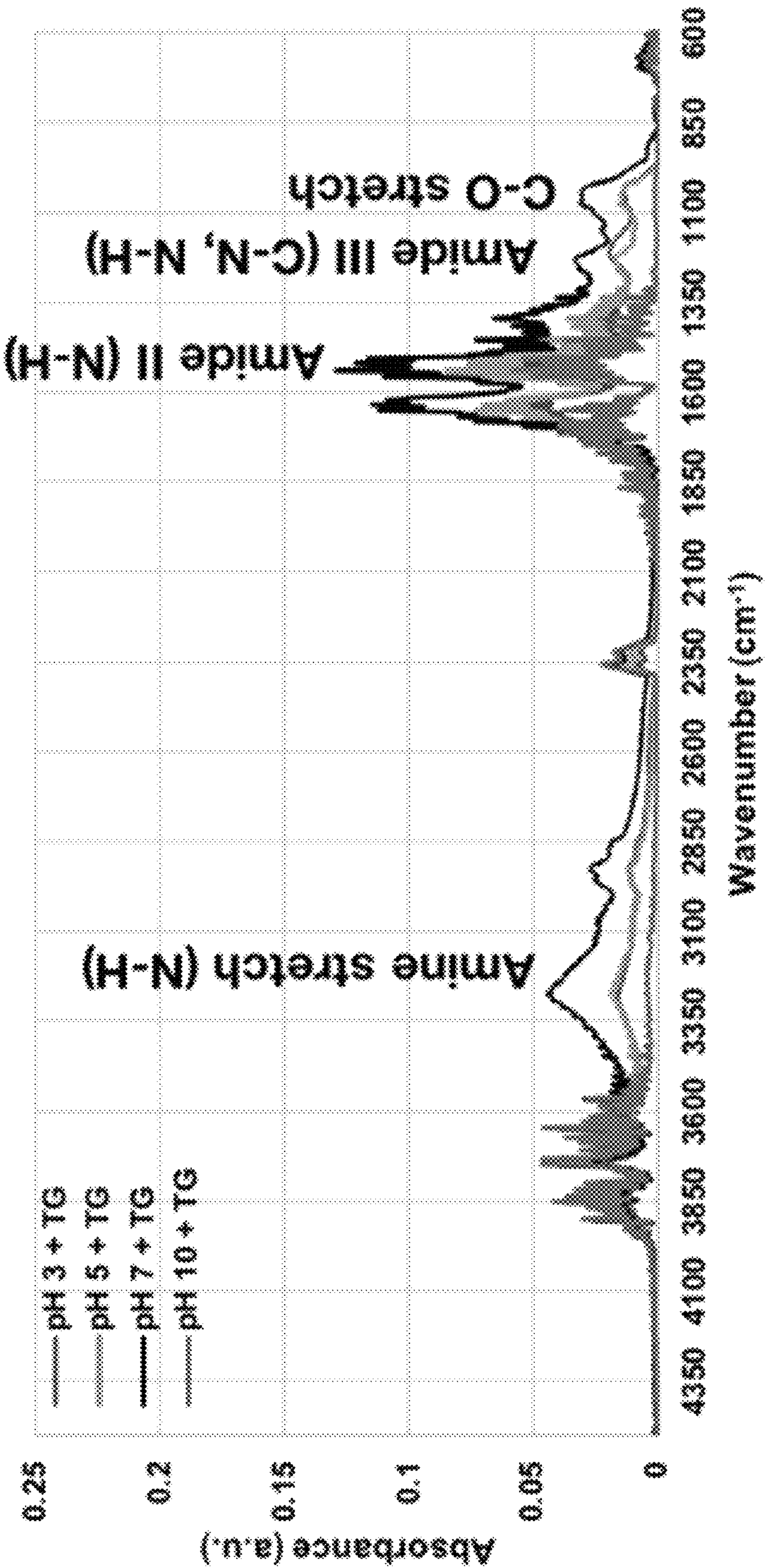
Figure 17D:
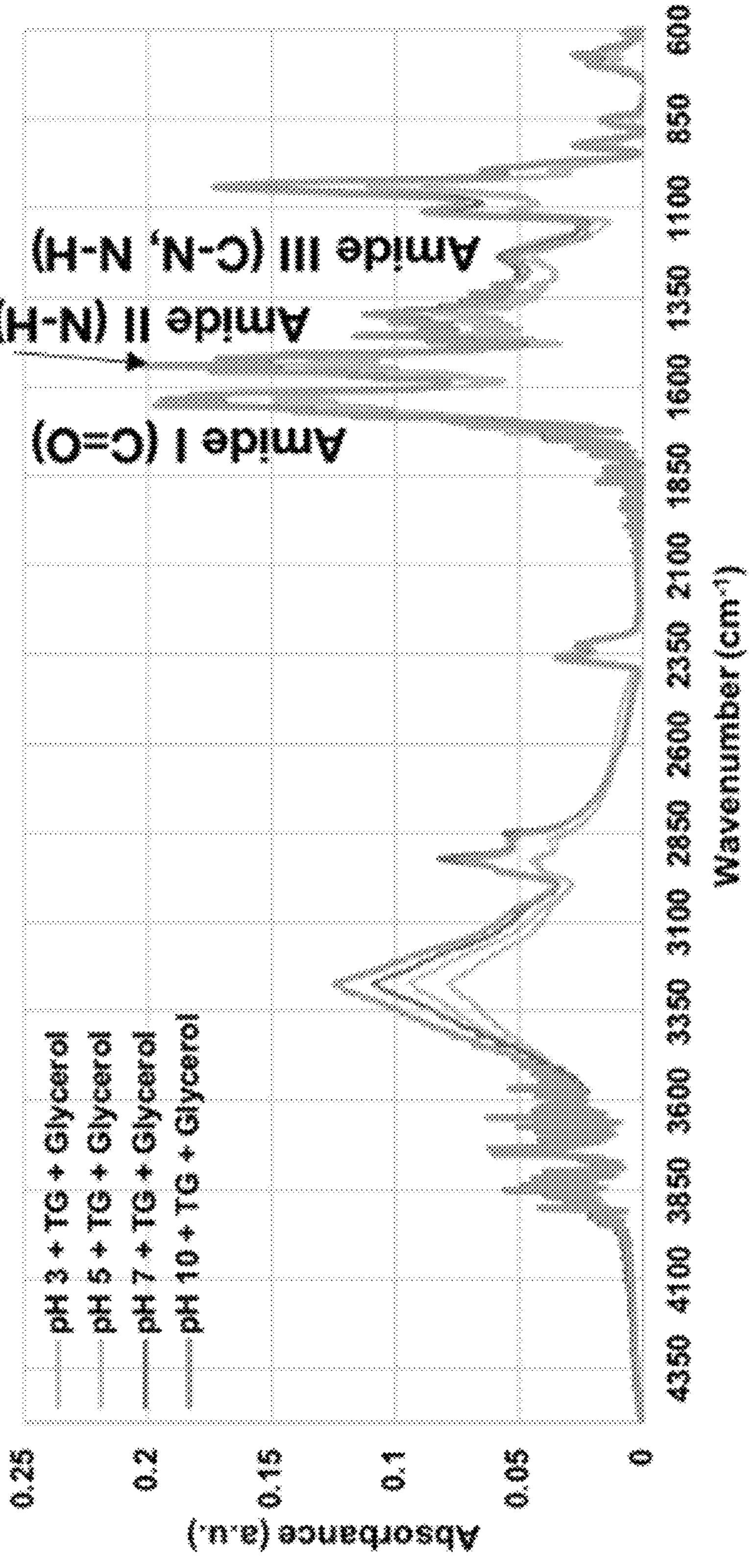

FIGS. 17A-17D: FTIR peak integration (n=3) for as fabricated SPI films. FTIR analysis (n=3) of soy protein isolate that was treated with 0.1 M NaOH, and subsequently adjusted to pH 3, 5, 7, or 10 with citric acid. Proteins are shown without and with 1% v/v or 5% v/v glycerol treatment, as well as without and with 1% w/w transglutaminase (TG) treatment. Note: In each graph, the only peak shifts detected were right shifts in amide III when a pH 3 dope was used. FIG. 17A: No Glycerol, No TG. FIG. 17B: 1% v/v Glycerol, No TG. FIG. 17C: No Glycerol, 1% w/w TG. FIG. 17D: 5% v/v Glycerol, 1% w/w TG.

Figure 18A:
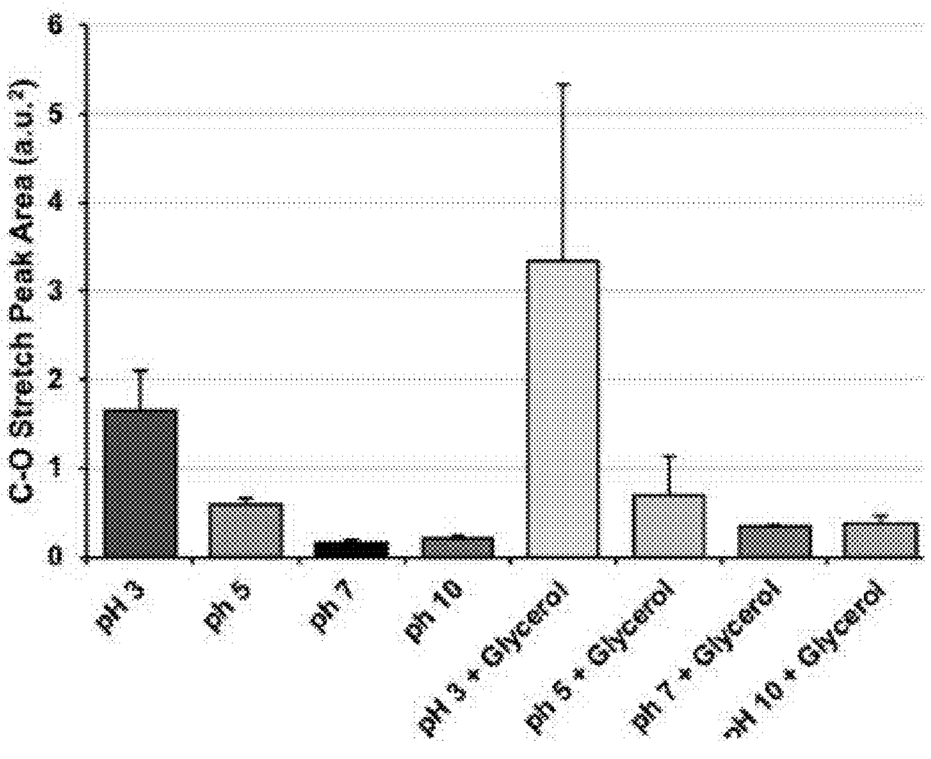
Figure 18B:
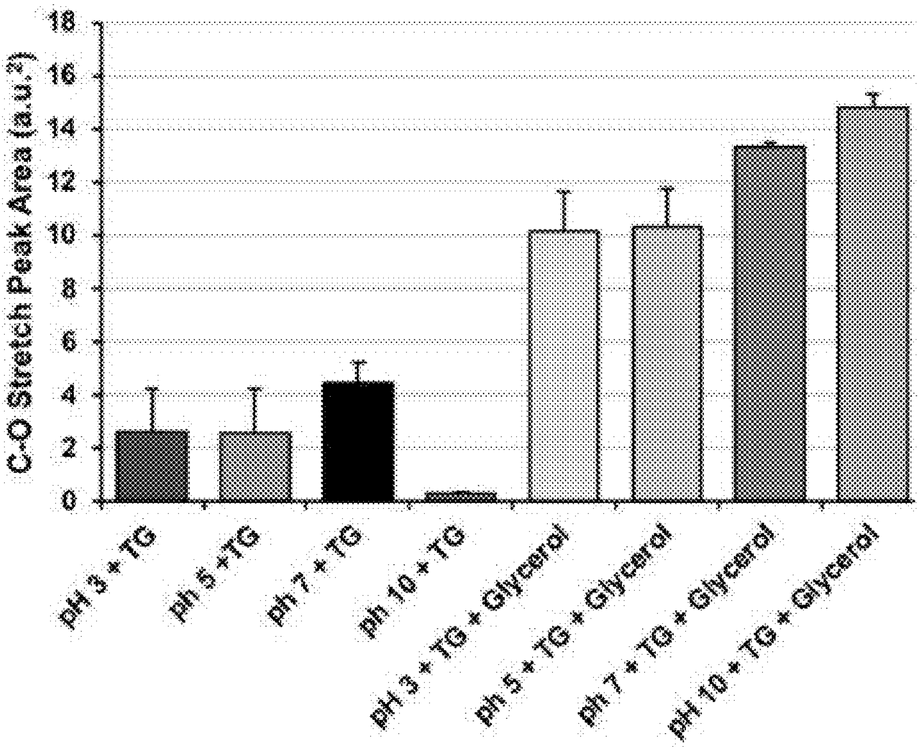
Figure 18C:
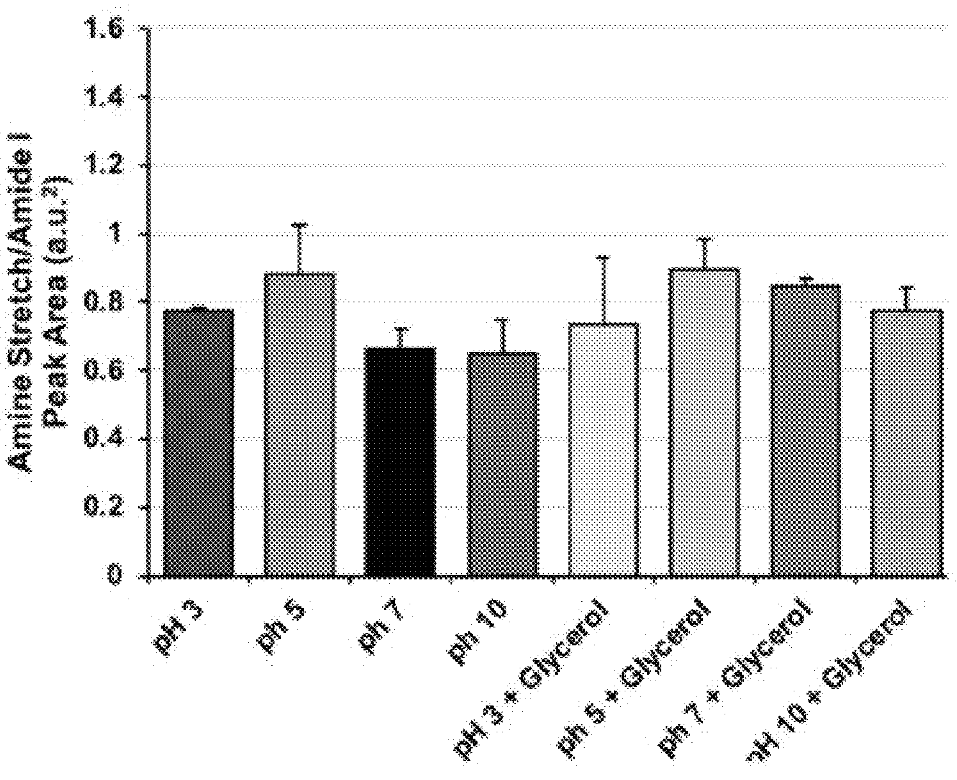
Figure 18D:
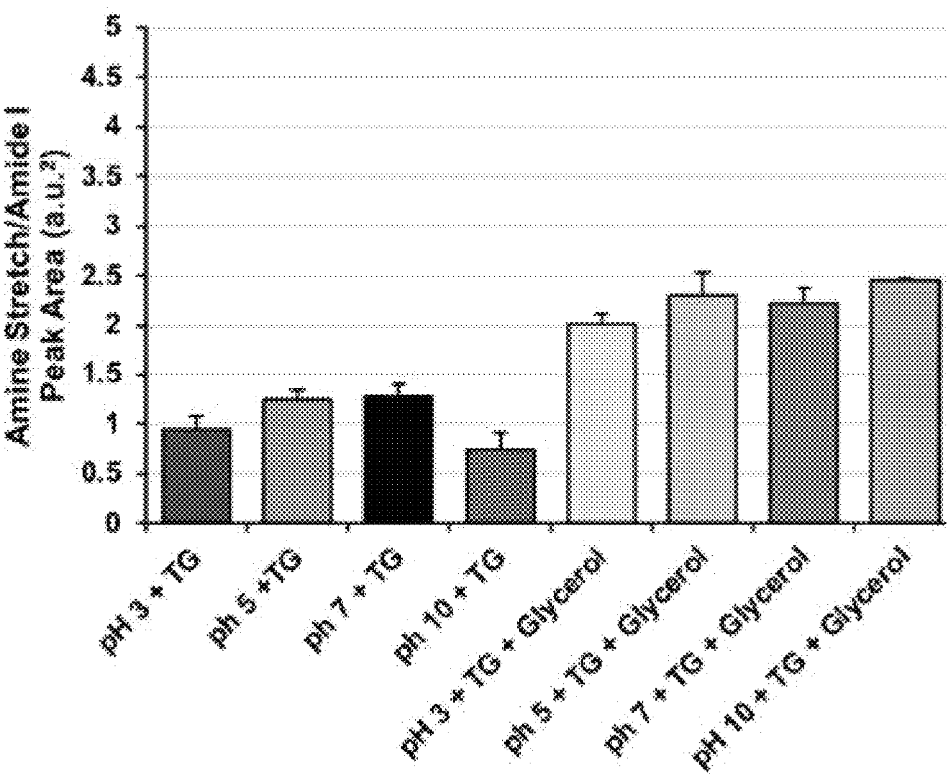
Figure 18E:
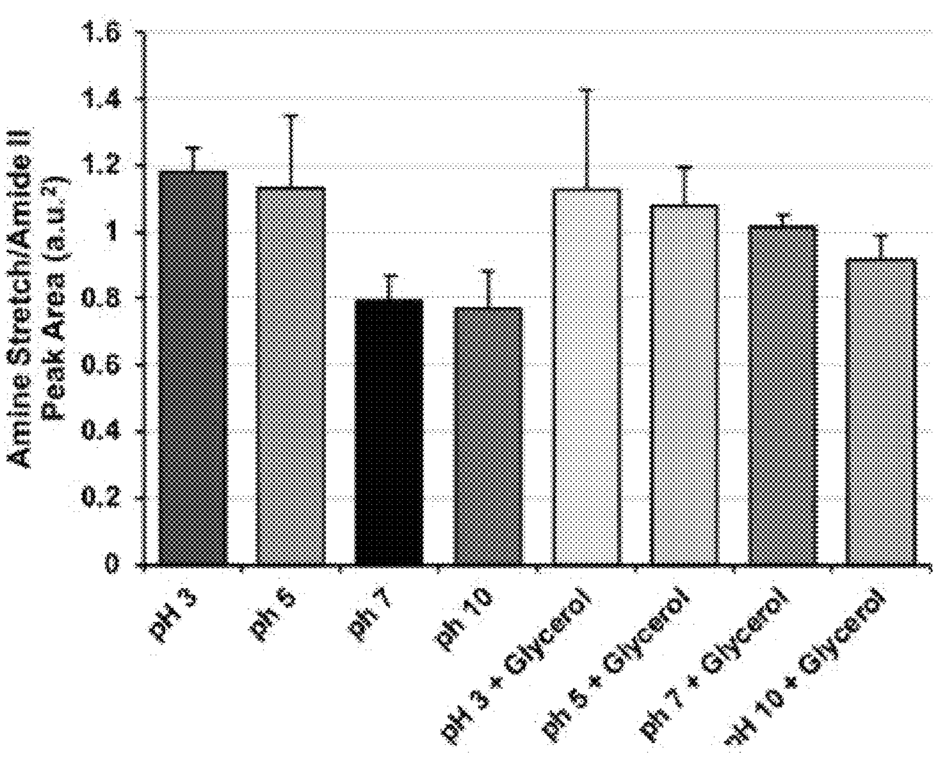
Figure 18F:
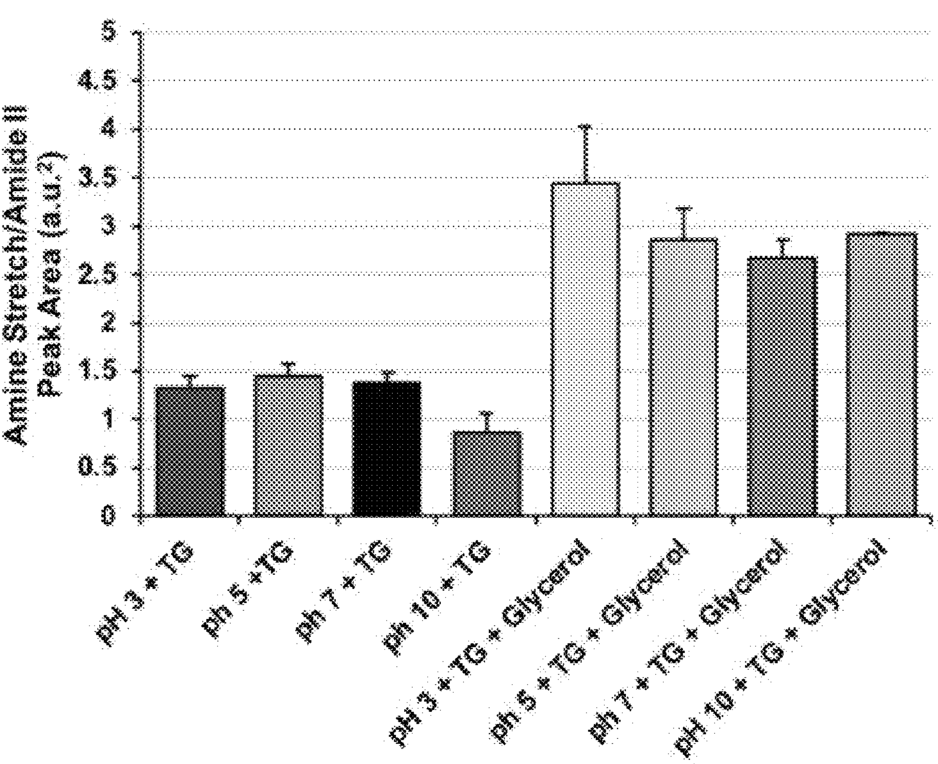

FIGS. 18A-18F: FTIR peak analysis (n=3) for as fabricated SPI films. FTIR peak integration (n=3) of soy protein isolate that was treated with 0.1 M NaOH, and subsequently adjusted to pH 3, 5, 7, or 10 with citric acid. FIG. 18A: C—O Stretch Peak Area, No TG. FIG. 18B: C—O Stretch Peak Area, +TG. FIG. 18C: Amine Stretch/Amide I Peak Area, no TG. FIG. 18D: Amine Stretch/Amide I Peak Area, +TG. FIG. 18E: Amine Stretch/Amide II Peak Area, No TG. FIG. 18F: Amine Stretch/Amide II Peak Area, +TG.

Figure 19A:
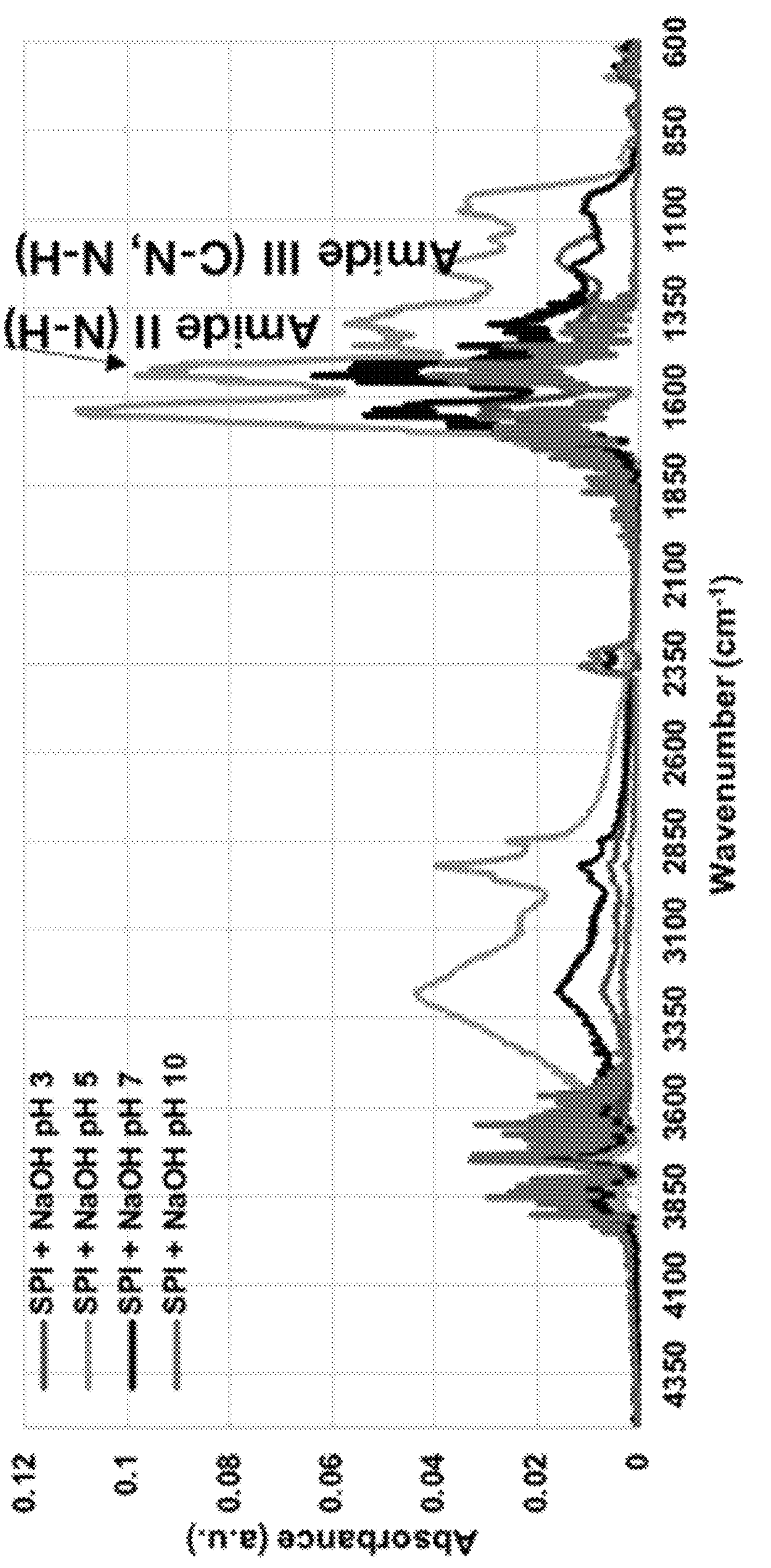
Figure 19B:
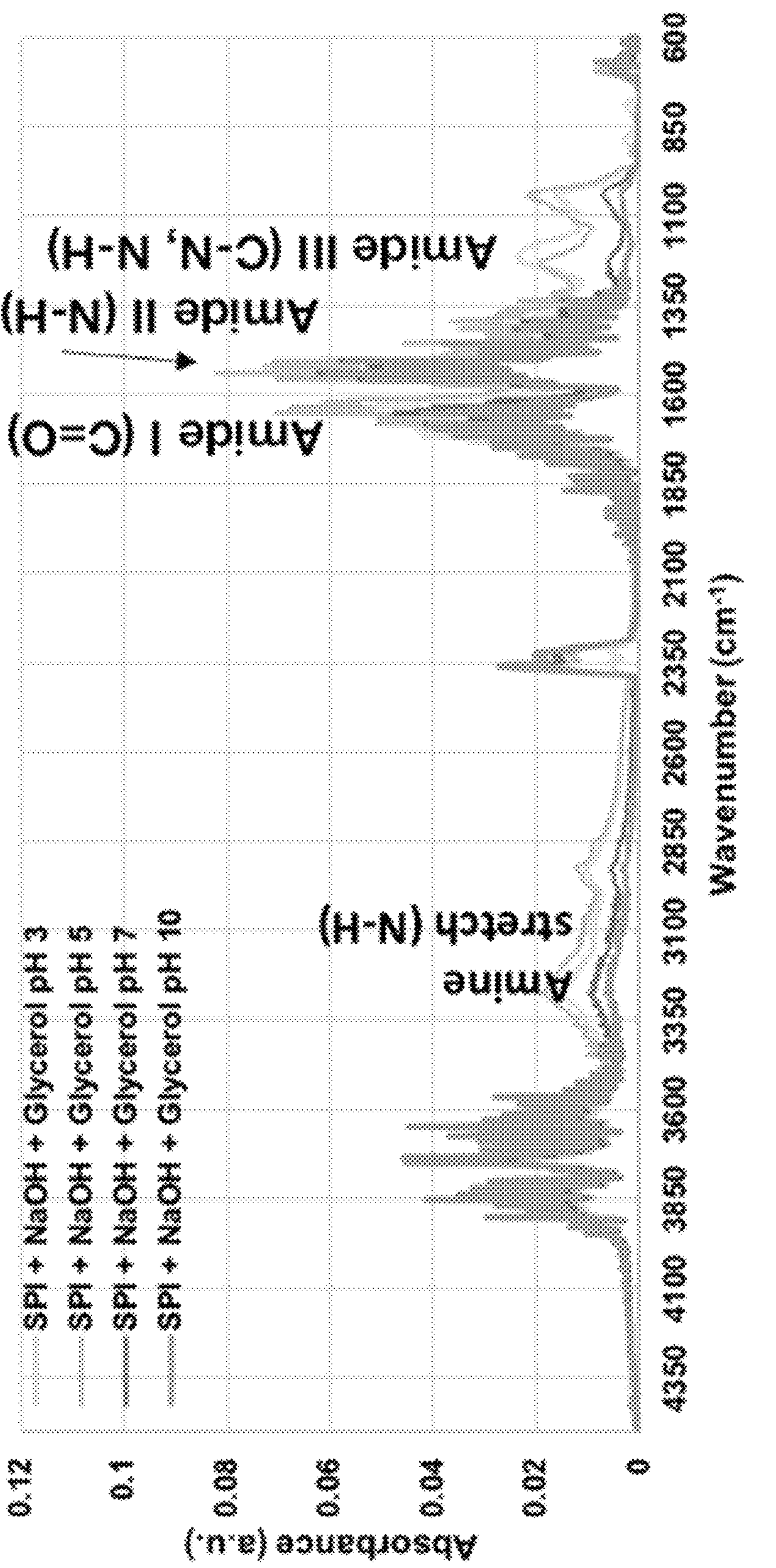
Figure 19C:
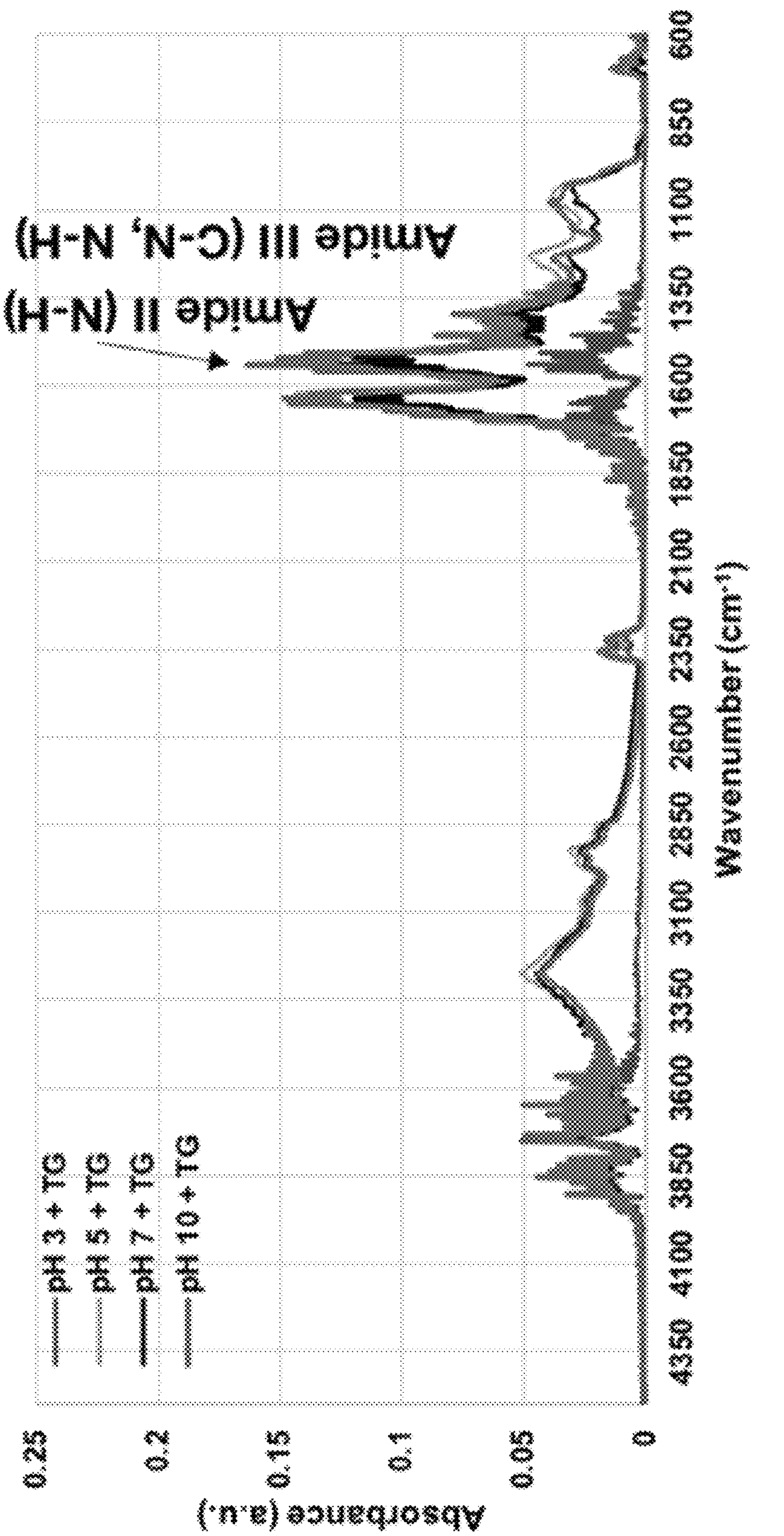
Figure 19D:
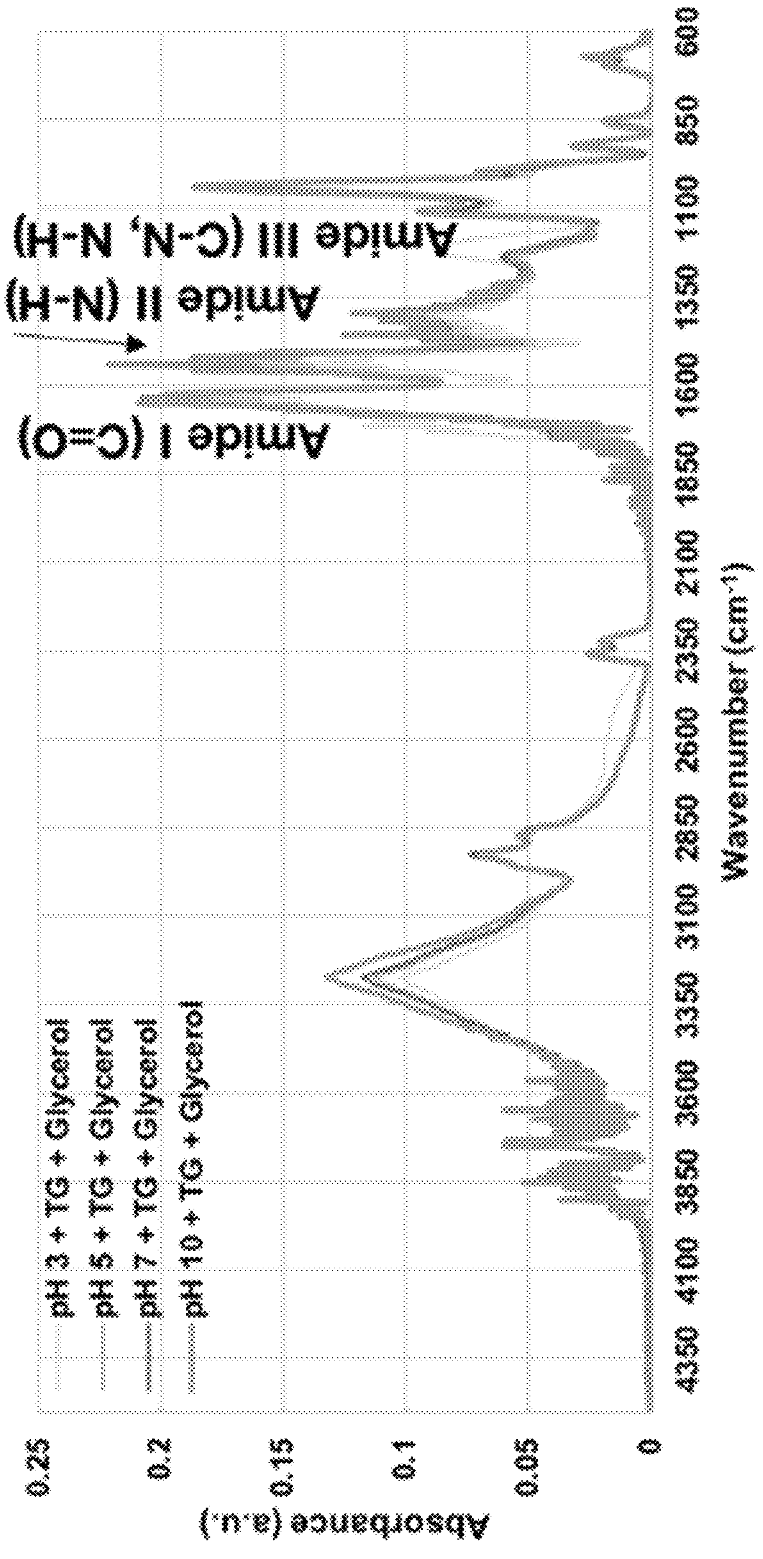

FIGS. 19A-19D: FTIR integration (n=3) for SPI films after vacuum dehydration at 25° C. FTIR analysis (n=3) of soy protein isolate treated with 0.1 M NaOH, and subsequently adjusted to pH 3, 5, 7, or 10 with citric acid. Proteins are shown without (left column) and with (right column) 1% v/v glycerol treatment, as well as without (top row) and with (bottom row) 1% w/w TG treatment. Note: In each graph, the only peak shifts detected were right shifts in amide III when a pH 3 dope was used. FIG. 19A: No Glycerol, No TG. FIG. 19B: 1% v/v Glycerol, No TG. FIG. 19C: No Glycerol, 1% w/w TG. FIG. 19D: 1% v/v Glycerol, 1% w/w TG.

Figure 20A:
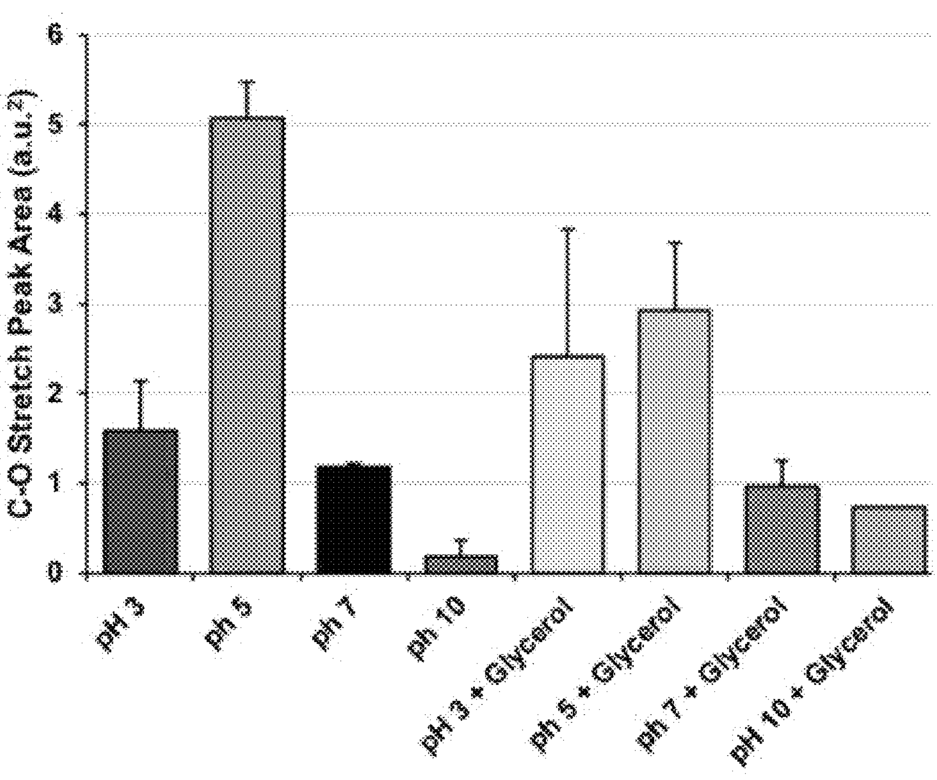
Figure 20B:
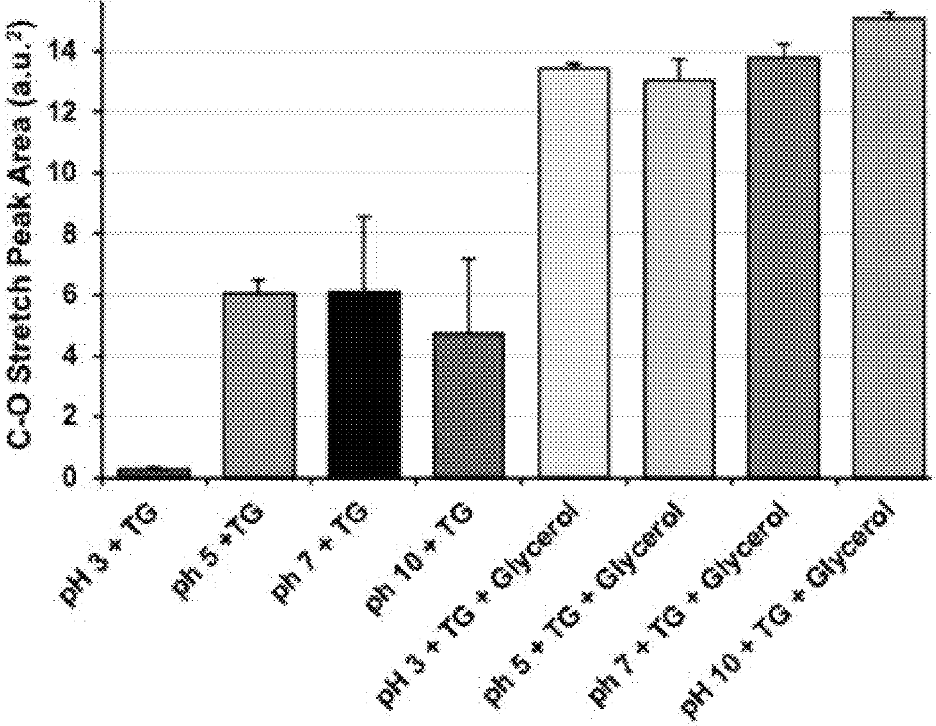
Figure 20C:
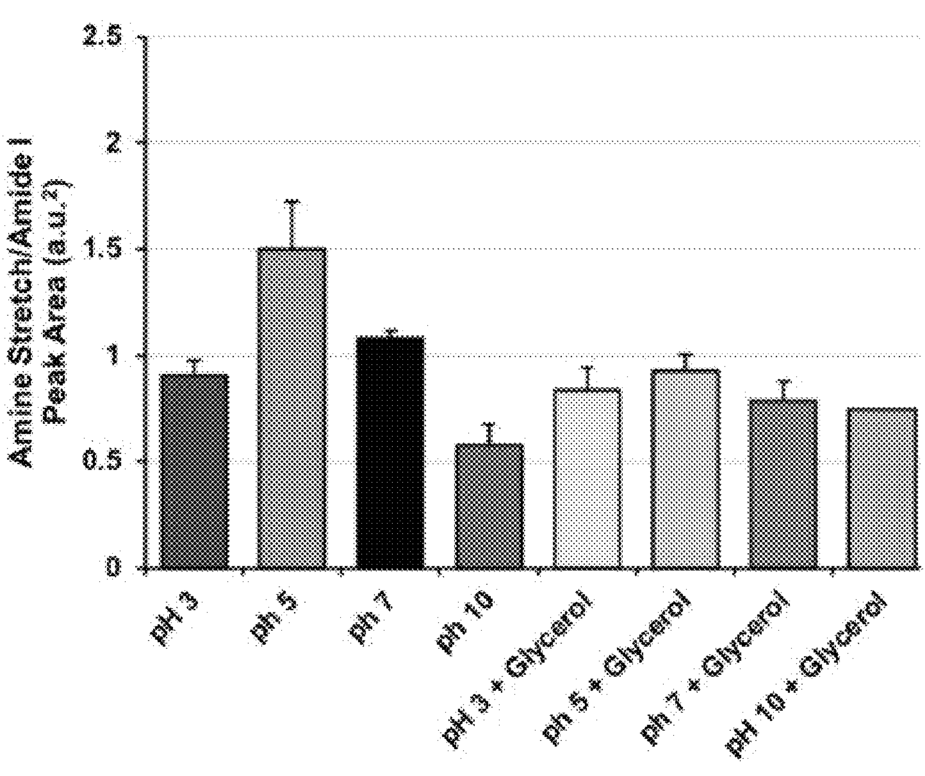
Figure 20D:
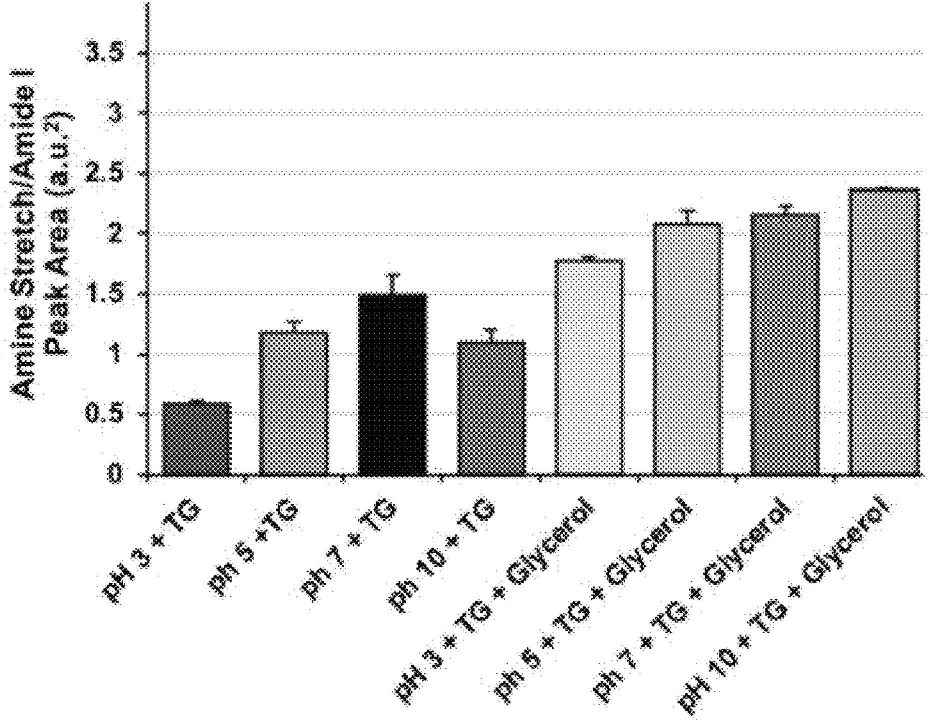
Figure 20E:
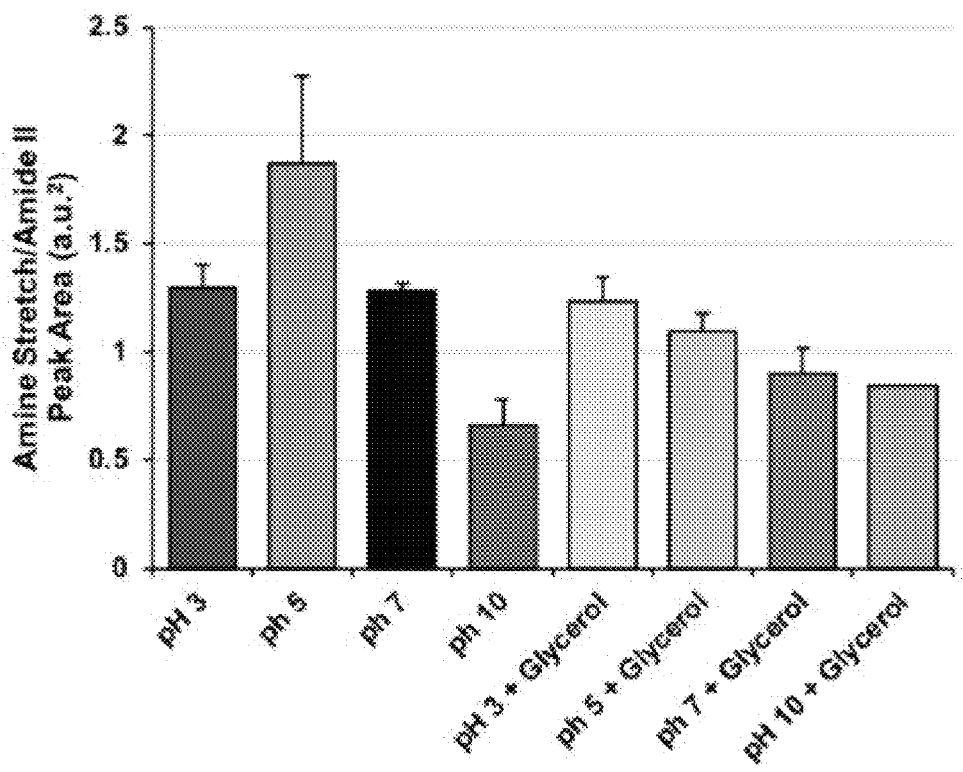
Figure 20F:
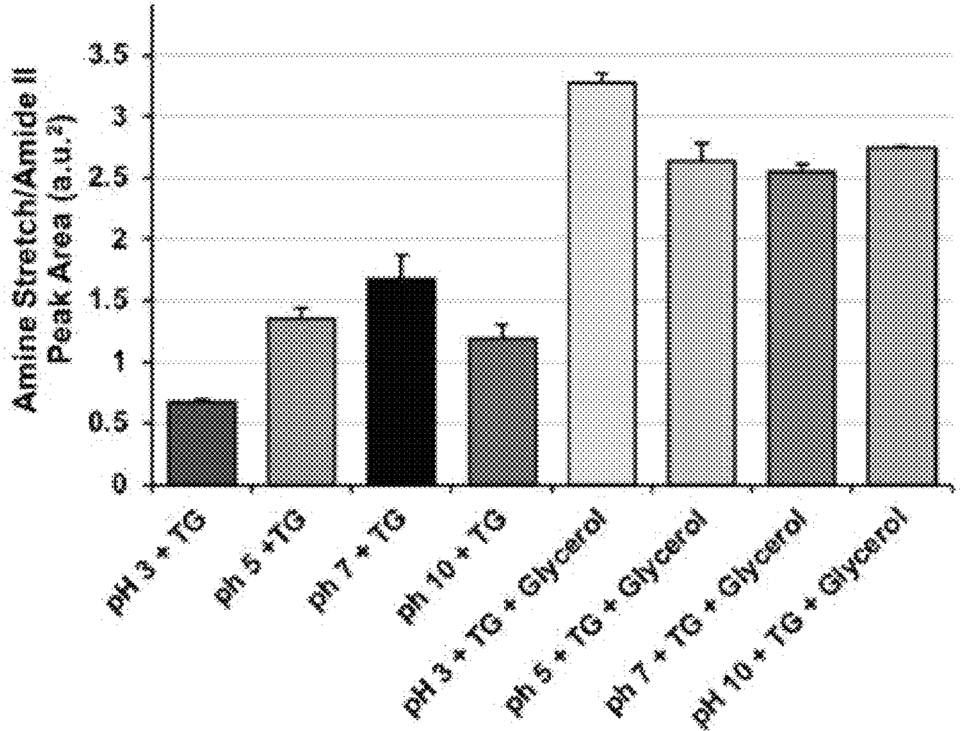

FIGS. 20A-20F: FTIR peak analysis (n=3) for SPI films after vacuum dehydration at 25° C. FTIR peak integration (n=3) of soy protein isolate that was treated with 0.1 M NaOH, and subsequently adjusted to pH 3, 5, 7, or 10 with citric acid. FIG. 20A: C—O Stretch Peak Area, No TG. FIG. 20B: C—O Stretch Peak Area, +TG. FIG. 20C: Amine Stretch/Amide I Peak Area, no TG. FIG. 20D: Amine Stretch/Amide I Peak Area, +TG. FIG. 20E: Amine Stretch/Amide II Peak Area, No TG. FIG. 20F: Amine Stretch/Amide II Peak Area, +TG.

DETAILED DESCRIPTION

In order to facilitate an understanding of the subject matter disclosed herein, each of the following terms, as used herein, shall have the meaning set forth below, except as expressly provided otherwise herein.

As used herein, "biopolymer" shall mean any polymeric biomolecule. As an example of a biopolymer, a peptide is a polymer of amino acid biomolecules. A "biopolymer composition" may refer to any composition that contains one or more biopolymers (for example, gelatin and an isolated recombinantly expressed protein; cellulose and an isolated recombinantly expressed protein; etc.). A "biopolymer raw material" is any biopolymer composition suitable for a process to generate a textile material.

As used herein, "biotextile material" shall mean any material used to create a textile, including but not limited to a fabric, fiber, or film, that is generated from a biopolymer composition.

As used herein, "bulking agent" or "bulking material" shall mean any substance or material used to provide additional structure or bulk, to a biotextile material generated using any of the methods described herein. Examples of a bulking agent or bulking material include, but are not limited to, cellulose, bacterial or microbial nanocellulose, methyl cellulose, gelatin, etc.

As used herein, "cellulose" shall mean a polysaccharide consisting of a linear chain of multiple β(1-4) linked D-glucose units. Cellulose is generated by, for example, most plant cells or certain bacterial cells. As used herein "nanocellulose" shall mean a nano-structured cellulose, which may have a fibril width of several nanometers and range of lengths up to several micrometers.

As used herein, "crosslink" shall mean formation of a bond to link two distinct molecules together, e.g. two protein units may be crosslinked by a transglutaminase that forms a covalent bond between glutamine on one of the protein units and a lysine on the other protein unit.

As used herein, "crosslinking capacity" shall mean the ability of a molecule to be crosslinked. The crosslinking capacity of a protein is a function of its amino acid composition. For example, the crosslinking capacity of a protein to be crosslinked to another unit of the protein by the crosslinking enzyme transglutaminase is a function of the glutamine and lysine content of the protein, e.g. an increase in the glutamine or lysine content of a protein enhances the transglutaminase crosslinking capacity of the protein.

As used herein, "functional characteristic associated with a protein" shall mean any physical property or characteristic of the protein that is a manifestation of the structure of the protein. For example, a functional characteristic associated with green fluorescent protein is green fluorescence or green coloring.

As used herein, "gelatin" shall mean a substance that is typically a glutinous mixture of peptides and proteins derived from collagen taken from, as examples, animal parts, from seaweed extracts, from plant extracts, etc. As used herein, a "gelatin protein" is a protein used to derive a gelatin or a protein that is part of a gelatin substance.

As used herein, "polymer" means a chemical compound or mixture of compounds formed by polymerization and including repeating structural units. Polymers may be constructed in multiple forms and compositions or combinations of compositions. Polymers may be natural or synthetic. Examples of natural polymers include collagen, cellulose, silk fibroin, keratin, gelatin and polysaccharides such as chitosan and alginate.

As used herein, "purified protein" or "purified source protein" shall mean a protein molecule or protein molecules that have been substantially isolated or enriched from its original composition. For example, a recombinant protein may be purified from a bacterial lysate. Additionally, a purified protein may be purified from a natural product, for example, casein protein may be purified from mammalian milk. A purified source protein may comprise several different protein molecules, for example soy protein isolate, which comprises different types of protein molecules, may be purified from soybeans.

As used herein, "recombinantly expressed protein" shall mean any protein that is expressed from a non-naturally occurring, recombinant DNA construct. The recombinantly expressed protein may be expressed, for example, from a recombinant DNA expression construct in *E. coli* or *S. cerevisiae*.

As used herein, "source protein" shall mean a protein possessing a functional characteristic that is desired to be exhibited by a biotextile material.

As used herein, "tag" shall mean any amino acid modification to a source protein to enhance the isolation, detection, or crosslinking capacity of the protein. A tag sequence may be added to a DNA coding sequence of a source protein using recombinant DNA methods in order to express the tag as part of the recombinantly expressed protein. A recombinantly expressed protein may be modified at any position to contain the tag. A tag that enhances the crosslinking capacity of a recombinantly expressed protein is at least one amino acid in length. The tag may be added to a source protein, for example, as at least one amino acid appended to a terminus of a source protein, or as at least one amino acid inserted into the source protein. A tag may be added to a source protein by substituting an amino acid of the source protein for another amino acid. For example, an amino acid of a source protein may be substituted for a glutamine or lysine residue in order to enhance the transglutaminase crosslinking capacity of the protein.

As used herein, "transglutaminase" shall mean any enzyme that possesses transglutaminase activity, namely the formation of an isopeptide bond between a carboxamide group of a glutamine and an amino group of a lysine in a peptide. A transglutaminase may be isolated from any source, for example, a bacterial or mammalian cell. As used herein, a "transglutaminase curing bath" is any solution that contains an amount of transglutaminase for the purpose of crosslinking molecules that are exposed to the solution.

As used herein, all numerical ranges provided are intended to expressly include at least the endpoints and all numbers that fall between the endpoints of ranges.

As mentioned supra, the fashion industry is built on agriculture, livestock and petrochemical industries, and it is currently one of the most extractive and polluting industries in the world, and a major contributor to global climate change.

The subject matter disclosed herein enables textiles having desirable fiber characteristics to be obtained. As disclosed, many of the drawbacks of conventional approaches for manufacturing textile can be avoided by employing selected proteins, which can be engineered using recombinant DNA techniques and produced at scale for raw materials by microbes such as non-pathogenic *Escherichia coli* (*E. coli*), while decreasing the need for large amounts of water and energy and chemically intensive processes.

The following embodiments and examples (including details thereof) are set forth to aid in an understanding of the subject matter of this disclosure but are not intended to, and should not be construed to, limit in any way the invention that is claimed.

Figure 12A:
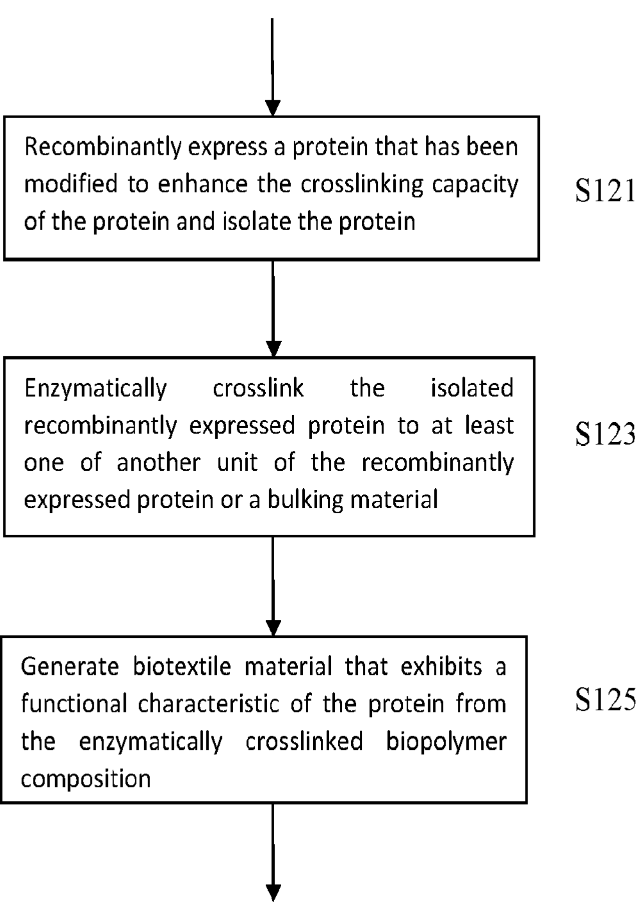
FIG. 12A: A flow chart for a method for generating a biotextile material, according to an embodiment.

The flow chart depicted in FIG. 12A outlines a method for generating a biotextile material, according to an embodiment of this disclosure. The method comprises a step of recombinantly expressing a protein to enhance the crosslinking capacity of the protein and isolating said protein (S121). The recombinantly expressed protein may be modified using recombinant DNA techniques to contain one or more tags that enhance the capacity of the protein to be crosslinked. For example, such a tag may contain at least one of a glutamine or lysine residue to enhance the ability of a transglutaminase enzyme to crosslink the protein.

The method further comprises a step of enzymatically crosslinking the isolated recombinantly expressed protein to at least one other unit of the recombinantly expressed protein or a bulking material (S123). For example, the isolated, recombinantly expressed protein may be part of a biopolymer composition that also comprises a bulking material, such as bacterial nanocellulose or gelatin. The biopolymer composition may be exposed to a crosslinking enzyme (e.g. transglutaminase), to crosslink the isolated recombinantly expressed protein to the bulking material. Alternatively, the isolated, recombinantly expressed protein may be exposed to a crosslinking enzyme (for example, in a transglutaminase curing bath), with addition of a bulking material to the transglutaminase curing bath.

The method further comprises a step of generating a biotextile material that exhibits a functional characteristic of the recombinantly expressed protein (S125). For example, the recombinantly expressed protein may be a fluorescent protein which is characterized by the functional characteristic of a fluorescent color. Surprisingly, upon enzymatic crosslinking of a biopolymer composition, as disclosed herein, comprising the fluorescent protein and generation of a biotextile material from the crosslinked biopolymer composition, the biotextile material (e.g., used as or in a fabric or film) exhibits and maintains the functional characteristic of the recombinantly expressed protein (in this example, fluorescent color).

In this disclosure, a method is described for generating a biotextile material comprising:

a) obtaining a biopolymer composition comprising a purified, recombinantly expressed protein, the recombinantly expressed protein having been expressed from a DNA coding sequence of a source protein, the DNA coding sequence having been optionally modified to include at least one tag sequence that enhances the crosslinking capacity of the recombinantly expressed protein;
b) exposing the composition to an enzyme to enzymatically crosslink the recombinantly expressed protein to at least another unit of the recombinantly expressed protein or another constituent of the biopolymer composition; and
c) generating a biotextile material based on the crosslinked composition, the biotextile material exhibiting a functional characteristic associated with the recombinantly expressed protein.

In some embodiments, the biotextile material generated in (c) includes a plurality of fibers formed from the crosslinked composition, and the tag sequence added to the modified DNA coding sequence for the recombinantly expressed protein in (a) enhances fiber formation in (c).

In some embodiments, the biotextile material generated in (c) includes a plurality of films formed from the crosslinked composition, and the tag sequence added to the modified DNA coding sequence for the recombinantly expressed protein in (a) enhances film formation in (c). The tag sequence enhances fiber or film formation because it enhances the crosslinking capacity of a source protein that may otherwise be unable to be enzymatically crosslinked at sufficient levels to generate a biotextile material. Notably, depending on the amino acid composition of the source protein, the protein may be sufficiently crosslinked without requiring modification by addition of a tag. Surprisingly, a fiber or film formed from the biotextile material exhibits a functional characteristic of the source protein after ex-vivo enzymatic crosslinking in (b).

In some embodiments, the source protein is a fluorescent protein, and the recombinantly expressed protein has at least a fluorescence property of the source protein. The fluorescence property i.e. color, exhibited by a biotextile material generated from a biopolymer composition comprising the fluorescent protein eliminates the need to dye the textile using traditional, environmentally unsustainable methods.

In some embodiments, the source protein is a green fluorescent protein (GFP), a red fluorescent protein (RFP), a near-infrared fluorescent protein, or a blue fluorescent protein (BFP). Near-infrared fluorescent proteins include fluorescent proteins that are visible as colors other than red, for example, near-infrared fluorescent proteins include small ultra-red fluorescent protein, which actually fluoresces blue.

In some embodiments, said another constituent of the biopolymer composition is a gelatin protein, and the enzyme employed in (b) includes a transglutaminase, and the gelatin protein cross-linked in (b) to the recombinantly expressed protein forms a bulking material of the biotextile material.

In some embodiments, wherein the enzyme employed in (b) includes a transglutaminase, and the recombinantly expressed protein is cross-linked to said another unit of the recombinantly expressed protein in (b), and a plurality of cross-linked units of the recombinantly expressed protein form a bulking material of the biotextile material.

In some embodiments, said another constituent of the biopolymer composition is a cellulose protein or cellulose protein composite, and the enzyme employed in (b) includes a transglutaminase, and the cellulose protein or cellulose protein composite, cross-linked in (b) to the recombinantly expressed protein, forms a bulking material of the biotextile material.

In some embodiments, the source protein is at least one of casein, elastin, a whey protein, or pelovaterin. The source protein may be any protein selected to impart a desired functional characteristic property of the protein to a textile. The casein may be in any form, including but not limited to alpha-, beta-, and kappa-casein. The whey protein may be any protein found in whey, including but not limited to, lactalbumin, lactoglobulin, and albumin.

In some embodiments, a concentration of the recombinantly expressed protein in the composition is 0.10%-0.2% per unit volume.

In some embodiments, the biopolymer composition obtained in (a) is in solution and an amount of the recombinantly expressed protein in the solution is in a range from 0.84 mg/ml to 3.495 mg/ml.

In some embodiments, the recombinantly expressed protein in the biopolymer composition is lyophilized.

In some embodiments, the composition comprises at least one of a gelatin, cellulose, or polysaccharide.

In some embodiments, the cellulose is methyl-cellulose or microbial nanocellulose.

In some embodiments, in the biopolymer composition, a ration of the recombinantly expressed protein to the microbial nanocellulose ratio is at least 1:1000 by mass.

In some embodiments, a concentration of the gelatin in the composition is at least 20% of the composition.

In some embodiments, in the composition, a ratio of the recombinantly expressed protein to the gelatin is at least 1:1000 by mass.

In some embodiments, the enzyme is a transglutaminase.

In some embodiments, a concentration of the transglutaminase to which the composition is exposed is 0.01% to 15% per unit volume of the composition.

In some embodiments, in the composition, a ratio of the recombinantly expressed protein to the transglutaminase is in a range from 1:1 to 300:1.

In some embodiments, the crosslinking step (b) comprises exposing the composition to a transglutaminase curing bath maintained at a temperature of 25° C. or lower.

In some embodiments, the transglutaminase curing bath has a pH in the range of 5.6-8.8.

In some embodiments, the composition is exposed to the transglutaminase curing bath for at least 15 minutes.

In some embodiments, the composition comprises a bulking agent.

In some embodiments, the bulking agent is first isolated and purified into a fiber, film, or pellicle prior to enzymatic crosslinking with the recombinantly expressed protein.

In some embodiments, the biotextile material is at least one of a fiber, film, or biopolymer raw material.

In some embodiments, further comprising extruding fiber by using the biotextile material.

In some embodiments, the fiber is extruded at rate of 1.75-2.0 ml per minute.

In some embodiments, constant tension is applied to the fiber during extrusion.

In some embodiments, further comprising electrospinning fiber by using the crosslinked composition.

In some embodiments, further comprising casting the crosslinked composition into a film, gel, or pellet suitable for textile production.

In this disclosure, a product formed from the biotextile material generated by the method of any one of the above embodiments is also described.

In this disclosure, a composition is described of a biotextile material comprising: (i) a recombinantly expressed protein expressed from a DNA coding sequence of a source protein, the DNA coding sequence having been optionally modified to include at least one tag sequence that enhances the crosslinking capacity of the recombinantly expressed protein; and (ii) another protein or another unit of the recombinantly expressed protein, crosslinked to said recombinantly expressed protein, the biotextile material exhibiting a functional characteristic associated with the recombinantly expressed protein.

In some embodiments, the biotextile material includes a plurality of fibers, and the tag sequence added to the modified DNA coding sequence for the recombinantly expressed protein enhanced fiber formation.

In some embodiments, the biotextile material includes a plurality of films formed from the crosslinked composition, and the tag added to the modified DNA coding sequence for the recombinantly expressed protein enhanced film formation.

In some embodiments, the source protein is a fluorescent protein, and both the recombinantly expressed protein and the biotextile material each has at least a fluorescence property of the source protein.

In some embodiments, the source protein is a green fluorescent protein (GFP), a red fluorescent protein (RFP), a near-infrared fluorescent protein, or a blue fluorescent protein (BFP). Near-infrared fluorescent proteins include fluorescent proteins that are visible as colors other than red, for example, near-infrared fluorescent proteins include small ultra-red fluorescent protein, which actually fluoresces blue.

In some embodiments, the recombinantly expressed protein is cross-linked to a gelatin protein forming a bulking material of the biotextile material.

In some embodiments, the recombinantly expressed protein is cross-linked to said another unit of the recombinantly expressed protein, and a plurality of cross-linked units of the recombinantly expressed protein form a bulking material of the biotextile material.

In some embodiments, the recombinantly expressed protein is cross-linked to a cellulose protein or cellulose protein composite, the cellulose protein or cellulose protein composite forming a bulking material of the biotextile material.

In some embodiments, the protein of the composition is isolated from a raw material as an alternative to recombinant expression. For example, in some embodiments the protein is any one of casein isolated from cow milk, elastin from the abductor muscle of post-consumer oysters, pelovaterin isolated from Chinese softshell turtle eggshells, or a soy protein isolate from soybeans.

Figure 12B:
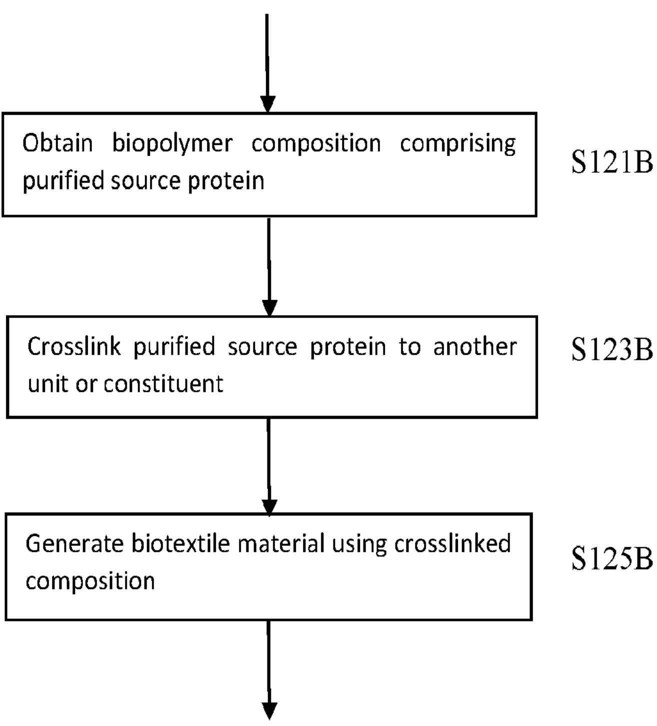
FIG. 12B: A flow chart for a method, according to another embodiment, for generating a biotextile material.
Figure 12C:
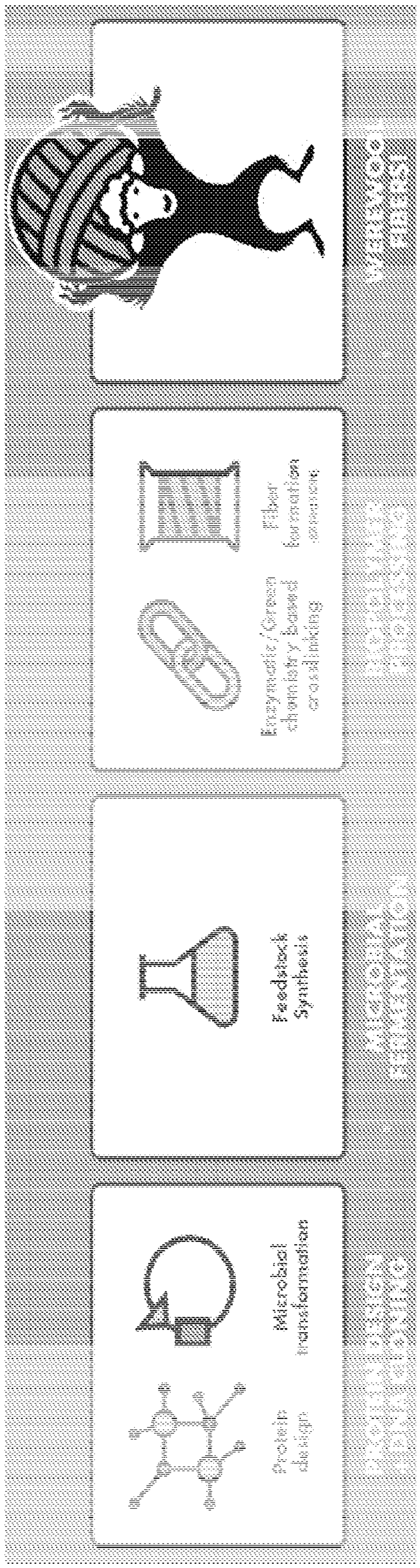
FIG. 12C: A simplified flowchart for biomaterial fiber formation.

The flow chart depicted in FIG. 12B outlines a method, according to another embodiment, for generating a biotextile material. The method comprises a step of obtaining a purified source protein (S121B). The purified source protein may be purified from a cell lysate that expresses the protein or purified from a natural composition.

The method further comprises a step of crosslinking the purified source protein to at least one other unit of the purified source protein or a bulking material (S123B). For example, the purified source protein may be part of a biopolymer composition that also comprises a bulking material, gelatin, cellulose, polysaccharide, protein-polysaccharide blend, or soy protein isolate or a subunit thereof. The biopolymer composition may be exposed to a crosslinking enzyme (e.g. transglutaminase) and/or to a calcium chloride solution to crosslink the components of the biopolymer composition.

The method further comprises a step of generating a biotextile material that exhibits a functional characteristic of the recombinantly expressed protein (S125B). For example, the purified source protein may be an elastin protein which is characterized by the functional characteristic of elasticity. Upon enzymatic crosslinking of a biopolymer composition comprising the elastin protein and generation of a biotextile material from the crosslinked biopolymer composition, the biotextile material (e.g., used as or in a fabric or film) exhibits and maintains the functional characteristic of the purified source protein (in this example, elasticity).

In some embodiments, the biopolymer composition comprises a recombinantly expressed protein or a protein isolated from a raw material that is capable of being sufficiently enzymatically cross-linked to components of the biopolymer composition without the addition of a tag that enhances the cross-linking capacity of the protein.

In this disclosure, a method is described for generating a biotextile material comprising:

a) obtaining a biopolymer composition comprising a purified source protein;

b) crosslinking a molecule of the purified source protein to at least another molecule of the purified source protein or another constituent of the biopolymer composition; and c) generating a biotextile material based on the crosslinked composition, the biotextile material exhibiting a functional characteristic associated with the purified source protein.

In some embodiments, the source protein is a recombinantly expressed protein, and the recombinantly expressed protein is expressed from a DNA coding sequence of the source protein. In some embodiments, the purified source protein is obtained from a natural resource and no recombinant expression is necessary, for example, casein may be isolated directly from mammalian milk.

In some embodiments, further comprising modifying the DNA coding sequence of the source protein to include at least one tag sequence that enhances a crosslinking capacity of the recombinantly expressed protein.

In some embodiments, the crosslinking is performed in (b) by exposing the composition to a crosslinking enzyme and/or a solution comprising calcium chloride. In some embodiments, the concentration of calcium chloride in the crosslinking solution is 0.1 to 10% w/v calcium chloride, preferably 3-5% w/v calcium chloride.

In some embodiments, the crosslinking enzyme is transglutaminase.

In some embodiments, the source protein is at least one of casein, elastin, pelovaterin, a whey protein, or a fluorescent protein. The source protein may be any protein selected to impart a desired functional characteristic property of the protein to a textile. The casein may be in any form, including but not limited to alpha-, beta-, and kappa-casein. The whey protein may be any protein found in whey, including but not limited to, lactalbumin, lactoglobulin, and albumin.

In some embodiments, the biopolymer composition obtained in (a) comprises at least one of a gelatin, cellulose, polysaccharide, protein-polysaccharide blend, soy protein isolate, or a primary globular subunit of soy protein isolate, such as the 7S or 11S subunits.

In some embodiments, the biopolymer composition obtained in (a) comprises a bulking agent.

In some embodiments, the biopolymer composition is obtained in (a) in a solution having a pH between 3 and 10.

In some embodiments, further comprising exposing the biopolymer composition obtained in (a) to a glycerol solution, wherein a concentration of glycerol in the solution is 0.1% to 10% v/v.

In some embodiments, further comprising exposing the biopolymer composition obtained in (a) to a glycerol solution, wherein the biopolymer composition obtained in (a) comprises a soy protein isolate, and wherein the crosslinking is performed in (b) by exposing the composition to transglutaminase.

In this disclosure, a product formed from the biotextile material generated by any one of the methods disclosed above is provided.

Disclosed herein are methods and compositions of biodegradable performance fibers with inherent color and performance. A protein that codes for a specific attribute in an organism e.g. stretch, rigidity, color, waterproofing, resilience, etc., is identified and the DNA sequence encoding the protein is altered to engineer the protein to be suitable for fiber generation of a biotextile material. The proteins are enzymatically crosslinked into fibers or films.

The inventive fiber development platform reduces the fashion industry's impact on our dwindling natural resources by eliminating the ecotoxicity of dyes and the end of life implications of synthetic fibers. The enzymatically crosslinked fibers are made with a circular life cycle by returning nutrients to the ecosystem at the end of their useful life, eliminating textile dye and finishing and microplastic pollution.

Furthermore, the disclosed methods may adhere to ASTM, AATCC, and ISO textile testing standards. To ensure that the inventive fiber is produced in a closed loop system, the methods described herein may be utilized with green chemistry and responsible waste management. Widely recognized fashion industry tools such as the Higg index, life cycle assessment, Blue sign, and Cradle to Cradle certification allows for the monitoring, quantification, and continual reduction the environmental and social impacts of the fiber production. Indeed, compared to the production of conventional polyester, a life cycle assessment shows that even without considering eliminating the use of toxic synthetic dyes and end of life microplastic pollution, production of the disclosed fibers has a 55% lower carbon footprint, and uses 84% less water, which amounts to 1000× less water than cotton production.

From a technical standpoint, the fiber development platform described herein utilizes the color, diversity, and breadth of performance that nature has evolved over the past 3.8 billion years to generate high-performance, biodegradable textile fibers. This is an expansive approach which allows for development of an array of fibers with a variety of different functions. The novel methods of generating biotextile materials and performance fibers described herein have been developed to exhibit both high sustainability and circularity.

At the raw material stage of production, the biotextile materials are made in a laboratory and are not reliant on agriculture, livestock or petrochemicals, which are three of the largest industrial $CO_2$ contributors globally. The methods of generating the novel biotextile material uses inputs like sugar, potentially waste stream sugar, for example, to feed their microbial raw material processing step. This approach minimizes inputs such as water, fertilizer, and local environmental impacts like eutrophication caused by chemical runoffs in the raising of conventional livestock/agriculture.

The methods and biotextile compositions described herein offer the textile industry inherent structural color in a fiber, which cuts out the intensive water use and toxicity that is linked with textile dyeing. The alternative biotextile materials described herein also have the potential to replace widely used ecotoxic performance fibers and finishing processes without sacrificing performance. For example, while elastane only contributes to a small percentage of a garment, the presence of just 1% of this fiber renders a garment un-recyclable, and chemical finishes like waterproofing leach formaldehyde into the public water system. The biodegradable fibers use protein structure to provide these properties, and minimize the impact on human health and the environment. Indeed, while synthetic textiles are a leading source of microplastic pollution, the low impact fibers described herein have a circular lifecycle and are designed to not outlive a human lifespan in the ecosystem.

Inspired by nature and using the tools of biotechnology, biodegradable performance fibers with inherent color and performance have been created as described herein. Through evolution, nature has developed a myriad of performance properties that are dependent on and determined by protein structure. Methods to engineer proteins and integrate them into fabrics such that the fabric inherits a beneficial property of the protein in order to create sustainable performance textiles have been developed and are disclosed herein. Design and engineering of protein and protein-composite fibers to develop materials with beneficial properties such as color, moisture management, stretch, and water resistance, and that meet the performance demands of today's consumer have been developed and are described herein.

Transglutaminase is utilized to enzymatically cross-link cellular and engineered proteins and biopolymer composites into raw materials and fibers for textile applications, with the desired function of the protein e.g. fluorescent color, retained ex-vivo. Engineered proteins are generated and used to create biodegradable fibers with a range of inherent structural coloring and natural fluorescence by utilizing, for example, modified red and green fluorescent proteins (FP). Prototype fibers have been created and the material properties of these prototype fibers has been tested. For instance, for a pink fiber, a red fluorescent protein (RFP) from the discosoma coral has been utilized to impart red color to the fiber ex vivo. Not only does this protein provide color, it also provides UV protective properties to the coral. Surprisingly, these same properties are maintained in the fiber upon using enzymatic cross-linking methods to generate performance biotextiles as described herein. This demonstrates that the methods can generate fibers that retain the performance and functional characteristics of a protein outside of a living cell for use in textile applications, achieving color for textiles without the toxicity and water demands of conventional textile dyeing methods.

Accordingly, after identifying a performance property of interest, the DNA sequence of the protein having the desired property is isolated and edited or otherwise engineered to make it suited for fiber formation. Using microbes such as *E. coli* as raw material producing factories, the protein is expressed with the desired trait(s) to produce the feedstock for the fibers. The enzyme transglutaminase is used to crosslink proteins into biodegradable biopolymer performance fibers for textile applications, to extrude and electrospin fibers, or cast the material into films, gels, and or pellets suitable for textile production and spinning processes.

The transglutaminase crosslinks biopolymers and biopolymer composites, which is a combination of proteins and/or a combination of proteins and polysaccharides, that can be incorporated directly into a biopolymer hydrogel "dope" before extrusion or casting. Alternatively, the protein composite dope can be extruded into a transglutaminase curing bath. The concentration of a transglutaminase in a coagulation bath or in dope ranges from 0.01%-15%, with 1% concentration optimal, with protein: transglutaminase ratios ranging from 1:1 to 300:1. The dope composition may be a singular protein or a composite, which can include a variety of proteins and also may incorporate other biopolymers including polysaccharides for composite fibers and films. Composites include different protein combinations e.g. red and blue proteins, fluorescent proteins and casein or gelatin, and protein-cellulose composites, including methylcellulose and microbial nanocellulose. Pure fluorescent protein fibers can be created with this method. In previous tests, fibers have been successfully extruded using 20% gelatin and ~0.15% GFP in 1 mL of PBS. Solutions containing modified GFP at a concentration ranging from 0.84-3.495 mg/mL have been used to extrude fibers and cast films. Higher concentrations can also be achieved by lyophilizing the protein solution allowing for higher fluorescent protein concentrations. Preferably a minimal protein concentration needed to achieve color is used; as well as minimal media for the *E. coli* to express the protein. For composites, minimum GFP:gelatin or GFP:bacterial nanocellulose ratios with visible color were 1:>1000 by mass.

The functionality of the biofabric materials generated by enzymatic cross-linking of a cellular and/or engineered protein expressed and amplified in *E. coli* or yeast, wherein the protein is selected or designed to map a desired textile property into a functional fiber, film or biopolymer raw material suitable for industrial spinning processes, has been demonstrated as described herein. Such proteins, which may be modified with a tag that enhances the cross-linking capacity of the protein include, but are not limited to: casein, soy protein isolate, green and red fluorescent proteins (GFP, RFP), blue proteins, and elastin, which a protein abundant in the abductor muscle of post-consumer oysters. Such proteins are crosslinked into biotextile materials such as fibers, films, and biopolymer raw materials such that the biotextile material exhibits properties including but not limited to color, stretch, waterproofing, antimicrobial activity, etc.

For example, the methods described herein have been employed to create purple fibers without dyes or pigments by combining red and blue proteins; in this case the red fluorescent protein (RFP) offered UV-protection to the blue fluorescent protein allowing the color to be retained ex-vivo in a functional fiber. Enzymatic cross-linking with transglutaminase for a variety of proteins including colored and fluorescent proteins, casein, soy protein, and elastin, including marine elastin from the adductor muscle remaining in oyster shells post consumption is disclosed herein. Elastin is a structural protein found in connective tissues, elastic ligaments and cartilage. It is a different structural protein than collagen, and is composed of soluble tropoelastin protein containing primarily glycine and valine and modified alanine and proline residues. Elastin has the specific structural property of being elastic—allowing biological tissues to return to their original shape after being stretched or contracted. The adductor muscle, for example, is responsible for the opening and closing of an oyster shell, and consists mainly of elastin. This demonstration may indicate the possibility of a biodegradable spandex alternative based on protein fibers created with the novel platform and methodology for generating biotextile materials as described herein.

The fiber generation platform described herein creates the opportunity to transform low impact raw materials e.g. cellular and engineered proteins and biopolymer composites, into compostable performance fibers that promote circularity in the fashion industry. The technology offers the fashion industry independence from the climate and water impacts of conventional textile fibers, toxic dyes, and finishing processes, and an opportunity for brands to adhere to environmental regulations and effluent treatment laws, all while protecting human health.

Every kilogram of fiber created from the platform that supplants conventional (natural, manufactured, synthetic, recycled) fibers, minimizes the fashion industry's social and environmental impact. The biodegradable performance fibers also reduce a product's end of life impact, do not contribute to microplastic pollution, or toxic leachates, but rather return to the Earth as nutrients for a healthy ecosystem. Upon commercialization, the biodegradable performance fibers provide potentially limitless variation in inherent fiber color, function, and performance that consumer's demand.

As the marketplace for biomaterials continues to grow, the fiber development platform described herein enables exploration and engineering of naturally-based products to lead fiber industry innovation by creating novel textiles with a circular lifecycle while maintaining the performance attributes the market demands such as color, moisture management, and stretch, without the environmental impact from traditional inputs and processes.

In summary, the inventive technology is a platform for generating a wide array of customizable biodegradable protein fibers for use in textiles. Engineered proteins are synthesized in *E. coli* and enzymatically cross-linked with transglutaminase to form protein and biopolymer composites into functional fibers. Several fiber prototypes have been generated and tested using this approach. Unexpectedly, the functional characteristics of the engineered protein are exhibited by a biotextile material generated from a composition containing the engineered protein after the composition is enzymatically crosslinked ex vivo. Accordingly, this platform may be used to generate a range of textile fabrics with an array of pigments and functional characteristics such as UV protection, waterproofing, elasticity, among others. This technology has potential applications in encouraging sustainable development in the fashion and textile industries. Various other inventive aspects can be integrated or employed, as discussed infra.

EXPERIMENTAL DETAILS—FIRST SET

Example 1: Protein Fiber Discovery Platform Using Enzymatic Cross-Links

In Example 1, different protein combinations were tested for fiber extrusion; mechanical properties of extruded fibers were tested; and a variable speed fiber uptake mechanism was developed in order to better control extrusion and fiber formation. Extrusion challenges are addressed and measurements of protein concentration, solubility of transglutaminase in solution, and exploration of different transglutaminase concentrations for the fiber coagulation bath are described.

Results

Testing Protein Formulations for Fiber Extrusion: Gelatin+Transglutaminase (TG)

Crosslinking of 20% gelatin+PBS Buffer hydrogel was achieved by crosslinking in a 1% transglutaminase bath as described below. Fibers were then extruded and mechanically tested (See FIG. 3 for mechanical properties).

Fibers were extruded and mechanically tested from a GFP+gelatin hydrogel (3 ml GFP+2 ml PBS+1000 mg gelatin) crosslinked in a 1% transglutaminase bath according to the extrusion method below. This fiber did not dissolve in PBS solution overnight, and the GFP stayed in the fiber with fluorescent color intact (FIG. 2).

TABLE 1

Fluorescent Protein - Transglutaminase Ratios

| Study | Protein | Protein (mg) | [TGase] (% w/v) | TGase Bath Vol (mL) | TGase* (mg) | Protein Tgase |
|---|---|---|---|---|---|---|
| 1 | BFP | 53.7 | 25 | 1 | 2.5 | 21 |
| | BFP | 250 | 25 | 1 | 2.5 | 100 |
| | BFP | 100 | 25 | 0.2 | 0.5 | 200 |
| 2 | GFP+ | 48.5 | — | 0.5 | 1.25 | 39 |
| | GFP+ | 22.9 | — | 0.5 | 1.25 | 18 |
| | GFP+ | 98.4 | — | 0.5 | 1.25 | 79 |
| | GFP+ | 48.9 | — | 0.5 | 2.5 | 20 |
| | GFP+ | 27 | — | 0.5 | 2.5 | 11 |
| | GFP+ | 101.1 | — | 0.5 | 2.5 | 40 |

TABLE 2

Summary of mechanical properties of different extrusion runs (same protocol for each) for gelatin and GFP cross-linked in a 1% TG coagulation bath. Variability is attributed largely to limited control over extrusion profile and speed, which is addressed by a variable speed fiber uptake mechanism.
Fluorescent Protein- Transglutaminase Ratios Gelatin

| | Sample | Thickness | Young's Modulus (Mpa) | Yield Strength (Mpa) | UTS(ultimate tensile strength (Mpa) | Ductility | Toughness (J/m2) |
|---|---|---|---|---|---|---|---|
| Gelatin | Gelatin-9a | 0.3 | 2295.6 | 30.0 | 32.5 | 1.8 | 311987.5 |
| | Gelatin-9b | 0.3 | 2160.3 | 34.7 | 41.0 | 2.4 | 504808.0 |
| | Gelatin-10 | 0.4 | 998.1 | 6.2 | 9.8 | 1.2 | 116757.3 |
| | Gelatin-11A | 0.4 | 1441.7 | 43.9 | 51.7 | 5.0 | 1093348.1 |
| | Gelatin-11b | 0.6 | 375.6 | 14.3 | 14.5 | 4.5 | 384578.6 |
| | Gelatin-12 | 0.3 | 1427.9 | 22.9 | 28.1 | 3.1 | 35847.3 |
| | Gelatin-13 | 0.3 | 1305.3 | 15.8 | 22.7 | 2.7 | 248941.0 |
| | Gelatin-14A | 0.4 | 863.2 | 31.8 | 31.8 | 5.0 | 734496.3 |
| | Gelatin-14Brr | 0.5 | 1133.4 | 27.7 | 27.8 | 3.5 | 964982.6 |
| | Gelatin-14B | 0.5 | 1381.2 | 34.6 | 34.7 | 3.7 | 551310.0 |
| | AVERAGE | 0.388 | 1338.229124 | 26.20741912 | 29.46412447 | 3.272148618 | 527005.6693 |
| | STDEV | 0.104553135 | 569.9808277 | 11.38365299 | 12.17907674 | 1.289417458 | 315721.8488 |

Gelatin + GFP

| Sample | Thickness | Young's Modulus (Mpa) | Yield Strength (Mpa) | UTS (Mpa) | Ductility | Toughness (J/m2) |
|---|---|---|---|---|---|---|
| Gelatin-GFP-1A-rerun on 100N | 0.5 | 2655.6 | 49.7 | 53.8 | 2.9 | 845559.4 |
| Gelatin-GFP-1b re run | 0.6 | 2194.4 | 39.9 | 43.9 | 2.8 | 730445.2 |
| Gelatin-GFP-1b | 0.6 | 1995.1 | 42.3 | 46.2 | 3.8 | 1020820.8 |
| Gelatin-GFP-2b | 0.4 | 1224.5 | 14.4 | 19.1 | 2.1 | 195301.1 |
| Gelatin-GFP-3a | 0.5 | 1150.4 | 28.1 | 31.5 | 5.2 | 1002275.6 |
| Gelatin-GFP-3b | 0.5 | 1898.5 | 32.5 | 32.6 | 2.6 | 431575.4 |
| Gelatin-GFP-3c | 0.5 | 1430.3 | 43.2 | 48.4 | 5.7 | 1167084.9 |
| Gelatin-GFP-3d | 0.5 | 1389.4 | 33.4 | 33.4 | 3.3 | 510445.1 |
| Gelatin-GFP-4a | 0.5 | 1923.3 | 33.1 | 33.4 | 3.4 | 646360.6 |
| Gelatin-GFP-4b | 0.6 | 1767.2 | 42.0 | 43.8 | 5.1 | 982427.6 |
| Gelatin-GFP-5a | 0.4 | 1967.9 | 48.1 | 49.2 | 3.5 | 772701.0 |
| Gelatin-GFP-6a | 0.4 | 2360.8 | 43.5 | 44.2 | 2.6 | 538878.5 |
| Gelatin-GFP-6b | 0.4 | 3055.6 | 48.8 | 60.4 | 3.6 | 726595.2 |
| Gelatin-GFP-7a | 0.4 | 1316.6 | 4.7 | 9.6 | 1.1 | 46983.4 |
| Gelatin-GFP-7b | 0.4 | 1352.0 | 5.9 | 11.1 | 1.4 | 67952.4 |
| Gelatin-GFP-8 | 0.4 | 1757.0 | 28.8 | 37.0 | 2.9 | 486381.1 |
| AVERAGE | 0.515333333 | 1762.866052 | 35.85543911 | 38.62127602 | 3.701920724 | 3.701929724 |
| STDEV | 0.061306758 | 470.9748231 | 9.9211276 | 10.32923146 | 1.235077107 | 1.235077107 |

Fiber Take Up Mechanism for Tension

To create a machine that provided the tension desired for the fiber extrusion process, a machine was made from an Arduino Uno microprocessor, a Servo motor, and 3-D printer parts. The challenge of making this machine was coding the motor's program so that the motor ran at controlled variable speeds. At first this involved attempts to create a circuit and code with a potentiometer, but ultimately a code where the chip and motor were connected to a computer to control the desired speed proved to be a simpler yet more accurate design.

Extrusion Challenges

The following parameters all have an effect on the outcome of the fiber, and have been considered in order to determine optimal conditions for fiber formation:

pH: Using PBS bath (pH7.2) was preferred, as a more acidic bath (acetate buffer pH5.5) was attempted because microbial transglutaminase generally prefers a lower pH level, however the fiber did not form as well in the acidic bath, and the hydrogel sank to the bottom of the bath without forming a usable fiber.

Time in transglutaminase coagulation bath: Exposing the fiber to the bath for approximately an hour is preferred, as a 15 minutes exposure led to the fiber falling apart upon removal from coagulation bath.

Temperature: A warmer solution (and accordingly less viscous solution) led to a smoother strand being extruded, but the strand does not maintain a consistent shape at ~20° C. Cooler temperatures, ~14-15° C., help keep fiber intact, and coagulation occurs immediately and more consistently, such that longer, more homogenous fibers are extracted in this way.

Needle/Extrusion profile: A finer extrusion profile may allow a more viscous solution. Having a blunt tip to the needle keeps the fiber longer and more uniform.

Rate of Extrusion:

At 1.75 ml/min at 14° C. the fiber stayed intact for the full syringe of solution and the texture of the fiber was very beady, potentially due to Reynold's instability.

At 2 ml/min at 14° C. the fiber came out smoother, however it was difficult to keep the length of the fiber intact.

Tension: Upon generating fibers that were bead-like in nature, it is suggested that having consistent tension on the fiber during extrusion may improve fiber strength and uniformity. Based on this, an electronic fiber uptake machine coded to control the uptake of the fiber onto a spool at a specific speed was utilized, providing the ability to control the tension of the fiber as it is being extruded.

TABLE A1

Percent concentration per ml solution (weight percent) as determined by UV-Vis.

| Protein | Dilution Factor | Absorb-ance | Extinction Coefficient (mL/mg) | Concentration (mg/mL) |
|---|---|---|---|---|
| GFP(+6) E9 | 0 | 0.9737 | 2.9722747 | 0.327594221 |
| GFP(+6) A | 1 | 0.2451 | 2.9722747 | 0.824620966 |
| GFP(+6) B | 1 | 0.2778 | 2.9722747 | 0.934637717 |
| GFP(+6) E | 1 | 0.4469 | 2.9722747 | 1.503562259 |
| GFP(+6) B1 A | 1 | 0.2471 | 2.9722747 | 0.831349819 |
| GFP(+6) B1 B | 1 | 0.4859 | 2.9722747 | 1.634774898 |
| GFP(+6) B1 C | 1 | 0.2957 | 2.9722747 | 0.994860954 |
| GFP(+6) B1 D | 1 | 0.2497 | 2.9722747 | 0.840097329 |
| GFP(+6) B1 E | 1 | 0.6024 | 2.9722747 | 2.0267306 |
| GFP(+6) B1 F | 1 | 0.2749 | 2.9722747 | 0.92488088 |
| GFP(+6) B1 7/24/1 | 1 | 0.8753 | 2.9722747 | 2.944882626 |
| GFP(+6) B1 W5 | 0 | 0.2186 | 2.9722747 | 0.073546366 |
| GFP(+6) B1 W6 | 0 | 0.1859 | 2.9722747 | 0.062544691 |
| GFP(+6) B1 E6 | 1 | 0.1311 | 2.9722747 | 0.441076331 |
| GFP(+6) B1 E7 | 1 | 0.1481 | 2.9722747 | 0.498271583 |
| mCherry W7 | 0 | 0.5527 | 2.597767 | 0.212759649 |
| mCherry W8 | 0 | 0.5574 | 2.597767 | 0.214568895 |
| mCherry E5 | 1 | 0.6813 | 2.597767 | 2.622637032 |
| mCherry E6 | 1 | 0.2543 | 2.597767 | 0.978917653 |
| mCherry A | 2 | 0.01382 | 2.597767 | 0.531995359 |
| mCherry B | 2 | 0.139 | 2.597767 | 5.350749265 |

TABLE A2

Solubility of transglutaminase in DI water and PBS solutions as determined by visual inspection. Transglutaminase is soluble in all solutions tested.

| % Solution | Measured amount of TG (TI) | Liquid added | Soluble/ insouble |
|---|---|---|---|
| 0.50% | 5.8 mg | 1 ml PBS | soluble |
| 2.50% | 22.2 mg | 1 ml PBS | soluble |
| 5% | 58.6 mg | 1 ml PBS | soluble |
| 10% | 100.8 mg | 1 ml PBS | soluble |
| 25% | 253.9 mg | 1 ml PBS | soluble |
| 50% | 508.8 mg | 1 ml PBS | soluble |
| A.5% | 5.2 mg | 1 ml DI water | soluble |
| B2.5% | 20.1 mg | 1 ml DI water | soluble |
| C5% | 50.1 mg | 1 ml DI water | soluble |
| D10% | 101.2 mg | 1 ml DI water | soluble |
| E25% | 249.5 mg | 1 ml DI water | soluble |
| F50% | 508.8 mg | 1 ml DI water | soluble |

Unsuccessful mCherry and GFP Crosslinking Attempts

Figure 11A:
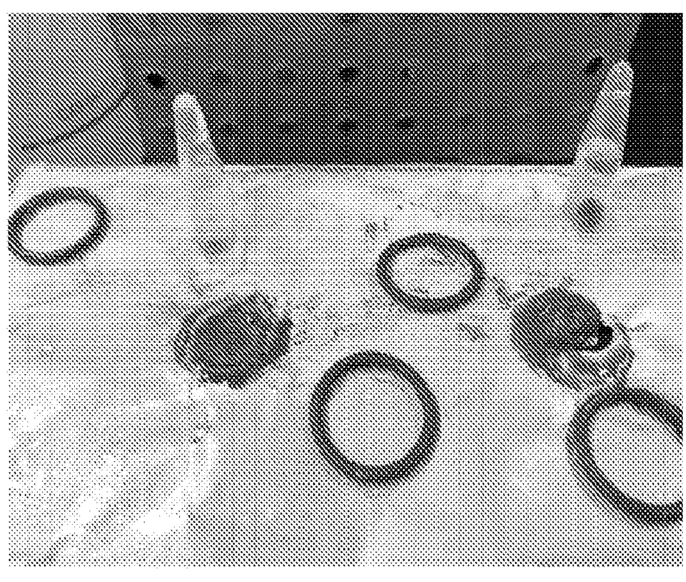
FIG. 11A: Unsuccessful mCherry-transglutaminase films after a one hour bake at 40 C.
Figure 11B:
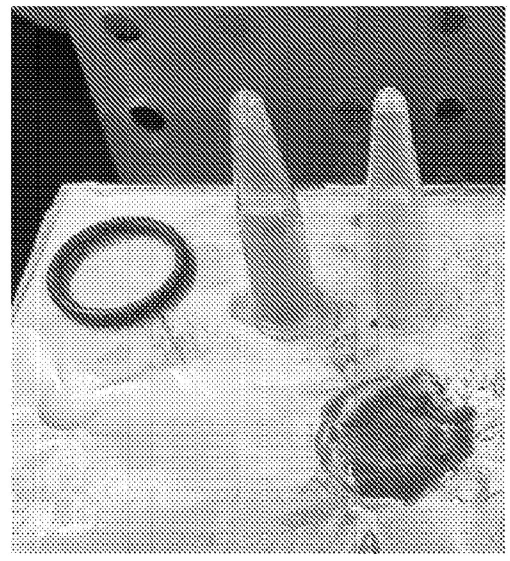
FIG. 11B: After 24 hours in distilled water, mCherry is dispersed into solution and hydrogel film has dissolved.

Unsuccessful attempts to crosslink mCherry after nickel column purification and suspension in Elution Buffer with transglutaminase were as follows: 1 ml mCherry+25% (252.5 mg) or 50% (497.4 mg) transglutaminase. Films of the mCherry-transglutaminase blend were oven dried for one hour at 40° C. Dried pieces of the hydrogel were left in PBS solution overnight to test for crosslinking. The water turned pink, indicating the hydrogel did not cross-link. It also appeared that the hydrogel completely dissolved into the PBS solution. See FIG. 11A and FIG. 11B.

Figure 11C:
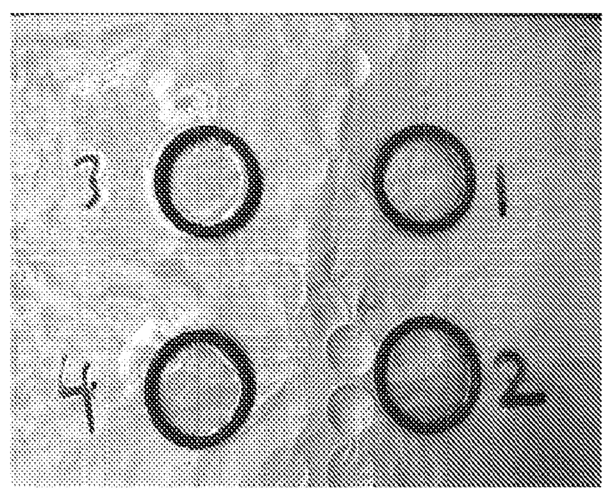
FIG. 11C: Unsuccessful GFP-transglutaminase gels before overnight bake at 38 C.
Figure 11D:
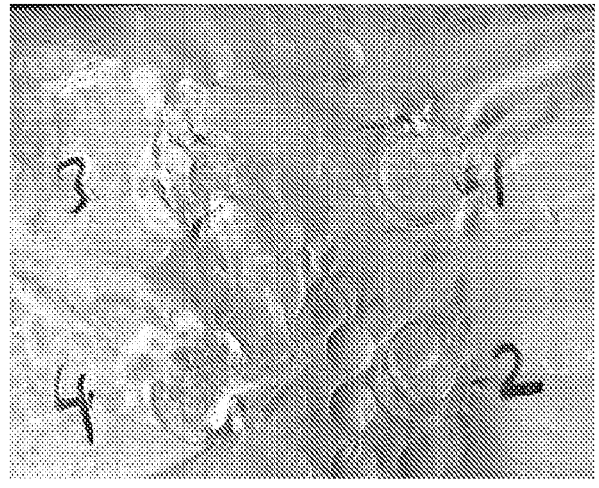
FIG. 11D: Unsuccessful GFP-transglutaminase gels after overnight bake at 38 C. No crosslinking was observed.

Using GFP (control and GFP with a positive tail), attempts to cross-link with transglutaminase and cast films under conditions described in the paragraph above were made. The composite formed a gel, which became a brittle film after an overnight bake at 38° C. As found for mCherry, an overnight soak in PBS indicated that the proteins did not cross-link as they dissolved into solution. See FIG. 11C and FIG. 11D.

Example 2: Gelatin as a Bulking Material or Carrier to Form Biopolymer Fibers and Films Containing Fluorescent Proteins to Create Textile Fibers with Structural Color Example 2 assesses the impact of the ratio of gelatin to green fluorescent protein (GFP) on fiber structure and GFP retention. Specifically, the least amount of gelatin that can still form fibers and retain GFP was determined. With certain formulations, GFP remains within the gelatin fibril, however, it was unclear if this is the result of covalent binding or simply physical entrapment within the fiber matrix. Here, the ratio of gelatin:GFP is decreased and the fiber integrity (visual, tensile) and the GFP retention ($DiH_2O$ incubation followed by testing for solution fluorescence/turbidity/absorbance) is assessed. Samples may then be tested by DSC, FTIR, and NMR to determine the method of entrapment of GRP e.g. chemical vs physical.

Figure 1A:
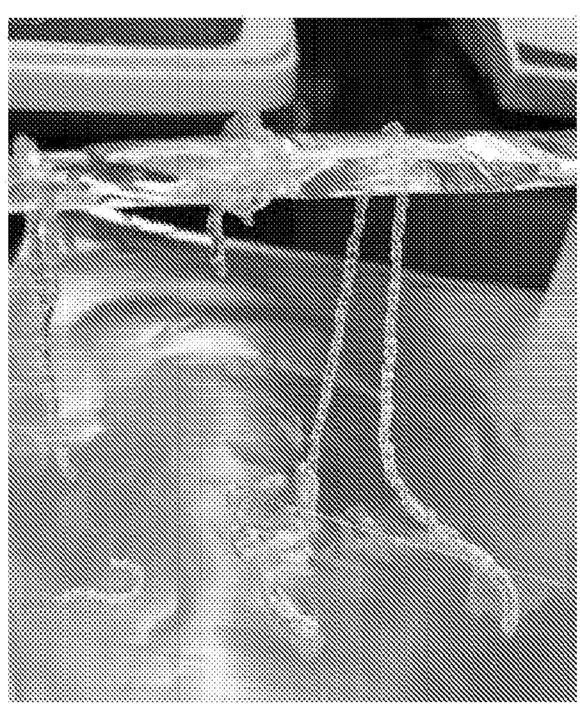
FIG. 1A: Gelatin fiber just after extrusion.
Figure 1B:
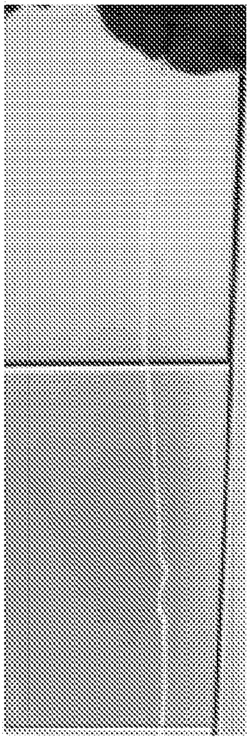
FIG. 1B: Gelatin fiber after 24 hours.
Figure 2A:
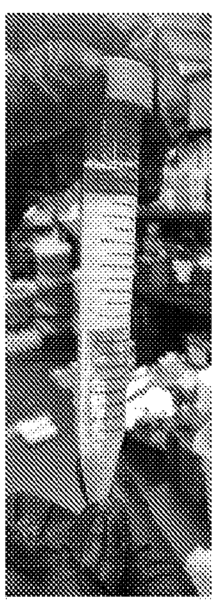
FIG. 2A: Extruded GFP+gelatin in 1% transglutaminase bath.
Figure 2B:
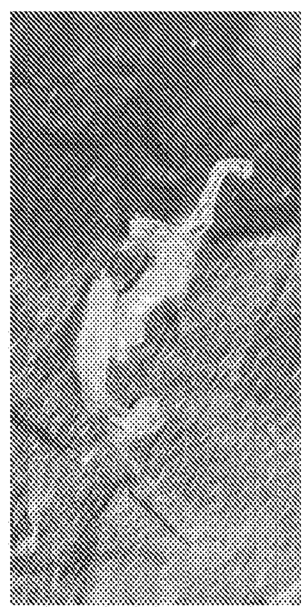
FIG. 2B: Dried GFP fiber after extrusion with color of protein retained.
Figure 2C:
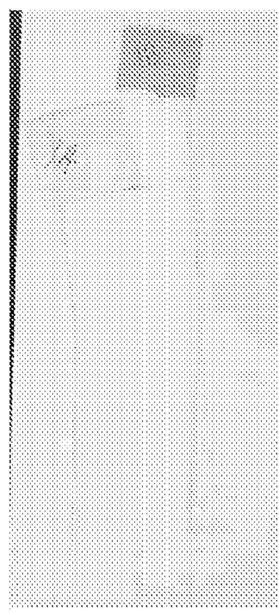
FIG. 2C: Extruded GFP+gelatin fiber samples prepared for mechanical testing.
Figure 2D:
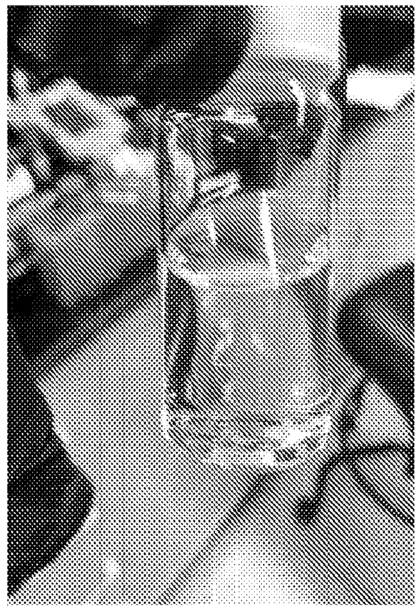
FIG. 2D: GFP+ gelatin fiber left in DI water overnight, next day photo.
Figure 3A:
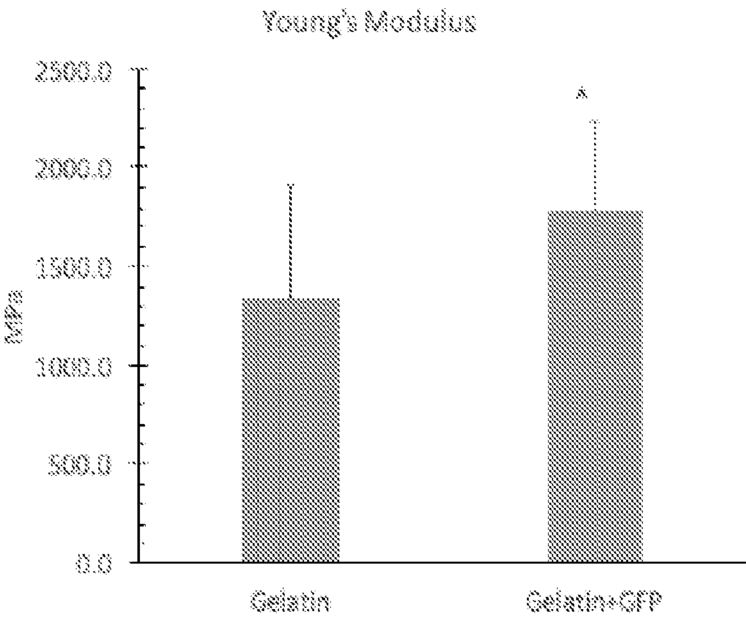
FIGS. 3A-3E: Mechanical properties, including Young's Modulus (FIG. 3A), Yield Strength (FIG. 3B), Toughness (FIG. 3C), Ultimate Tensile Stress (FIG. 3D), and Ductility (FIG. 3E) of gelatin and gelatin-GFP protein fibers crosslinked in 1% transglutaminse coagulation bath.
Figure 3B:
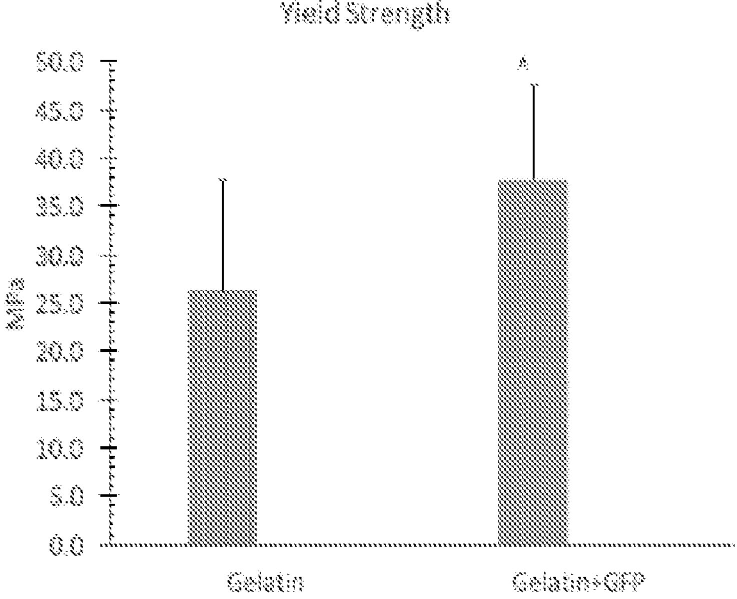
Figure 3C:
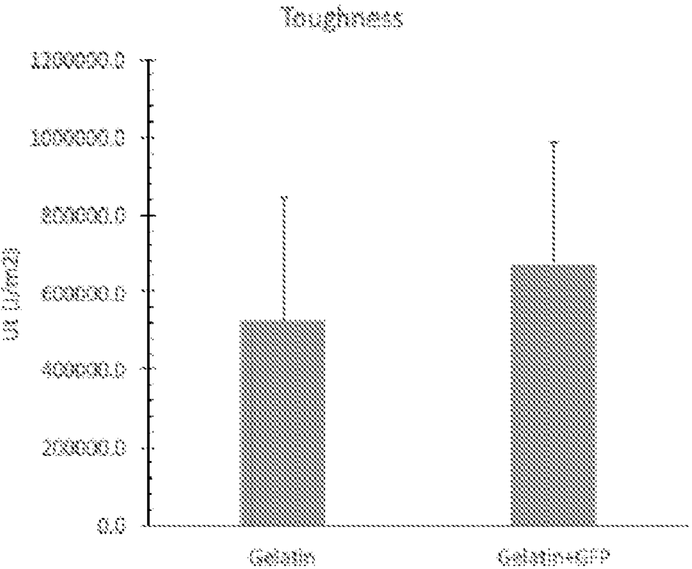
Figure 3D:
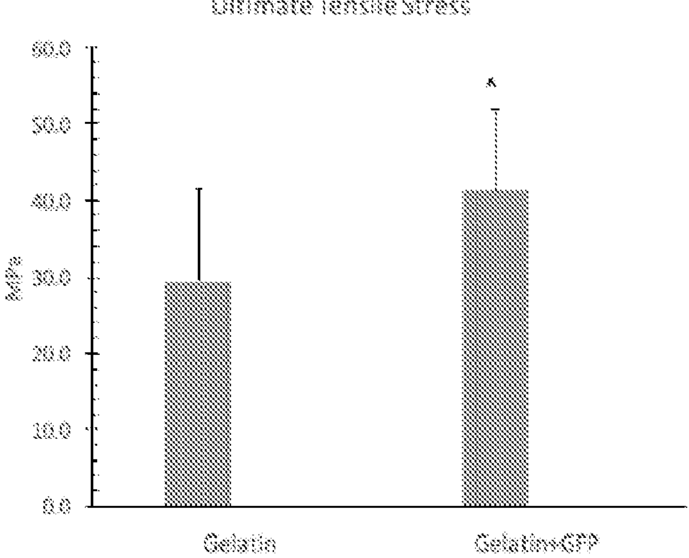
Figure 3E:
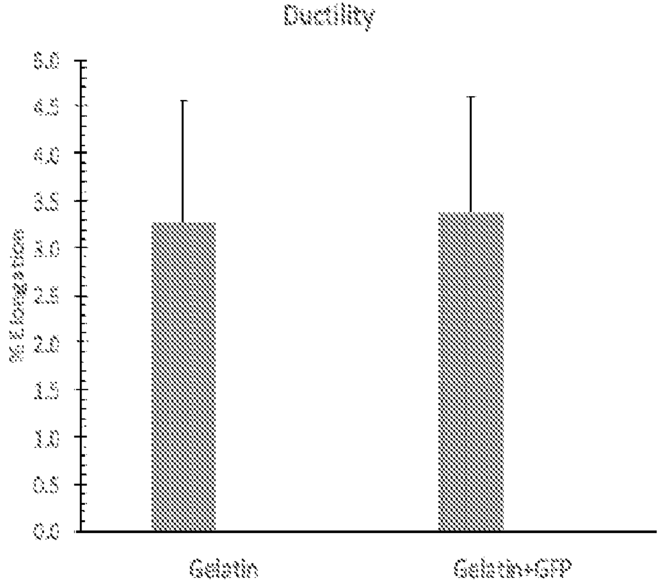
Figure 3F:
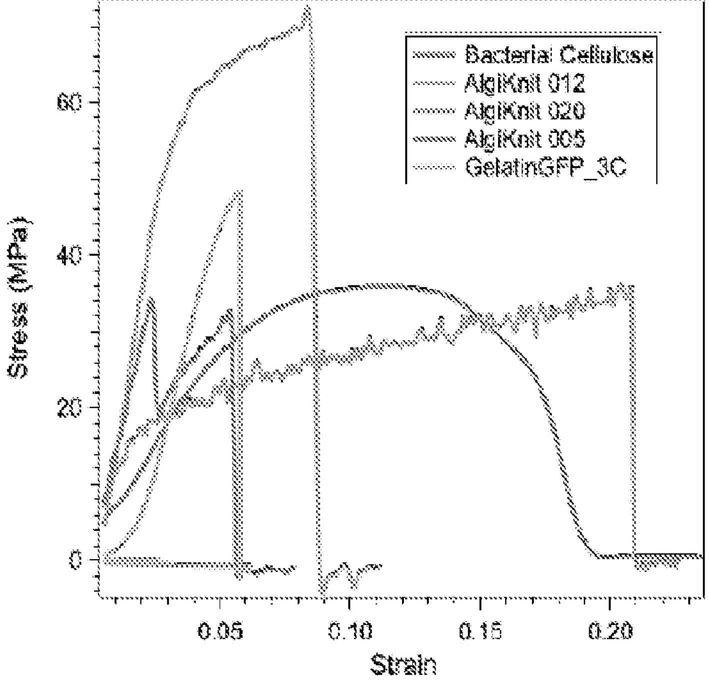
FIG. 3F: Comparison of protein engineered fiber with Algiknit and bacterial cellulose. Ductility and extrusion procedure may be improved with variable speed tension motor pulling fiber from an extrusion syringe.
Figure 4A:
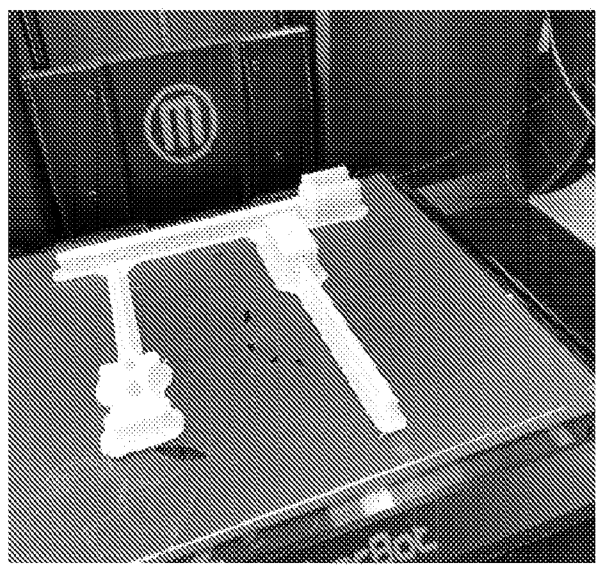
FIG. 4A: Designed and 3-D printed bobbins.
Figure 4B:
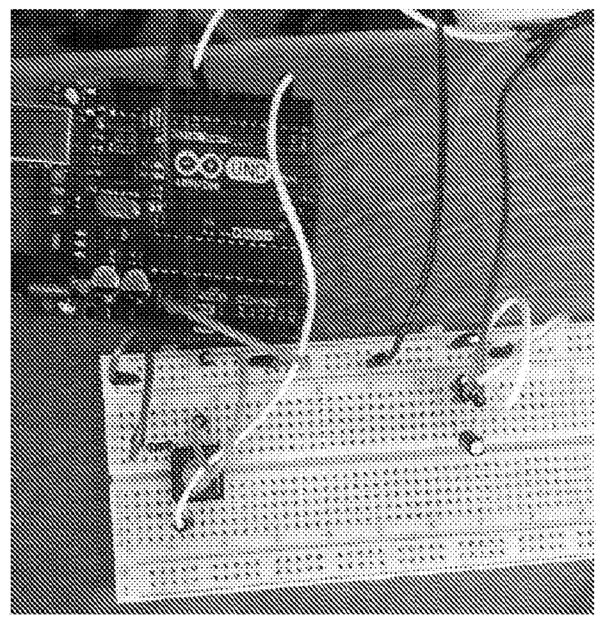
FIG. 4B: Circuit coded for a variable speed servo motor to provide tension for fiber extrusion.
Figure 4C:
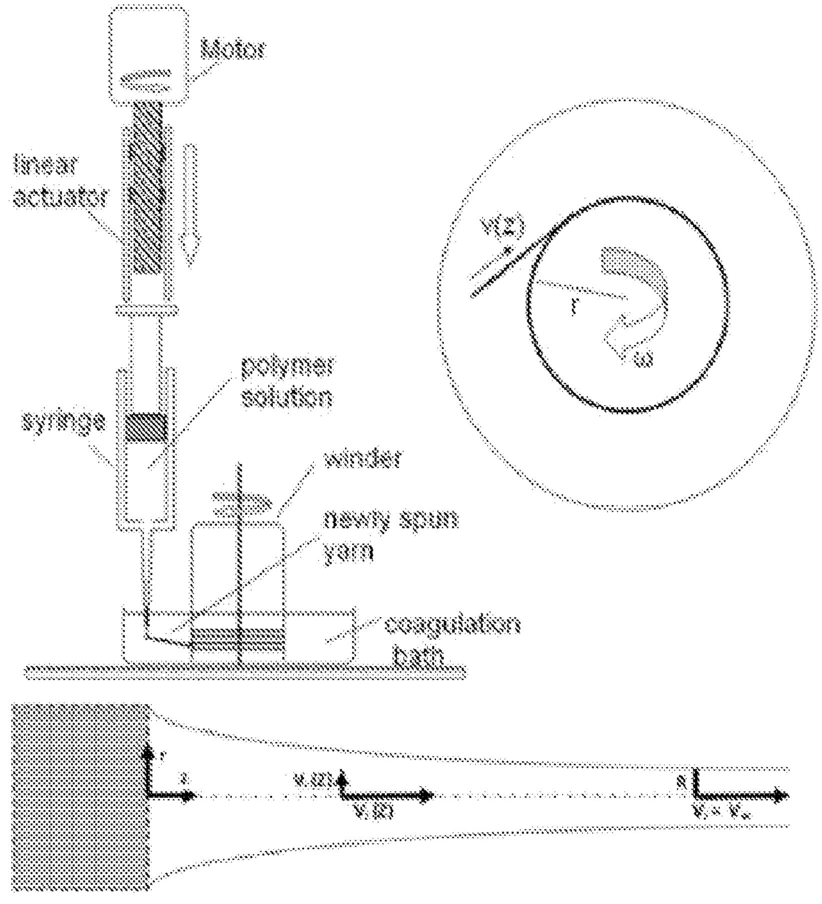
FIG. 4C: Schematic of a hydrodynamically and mechanically assisted extrusion procedure on which the mechanical fiber uptake design was based on. Modified from Wijesina, "Hydrodanymically and mechanically assisted wet spinning of elastometric polyurethane filaments", 2012.
Figure 5A:
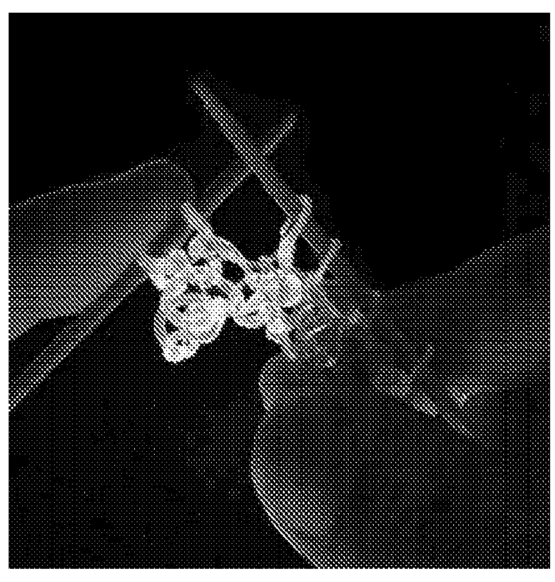
FIG. 5A: Fluorescence of a knitted a swatch made from GFP.
Figure 5B:
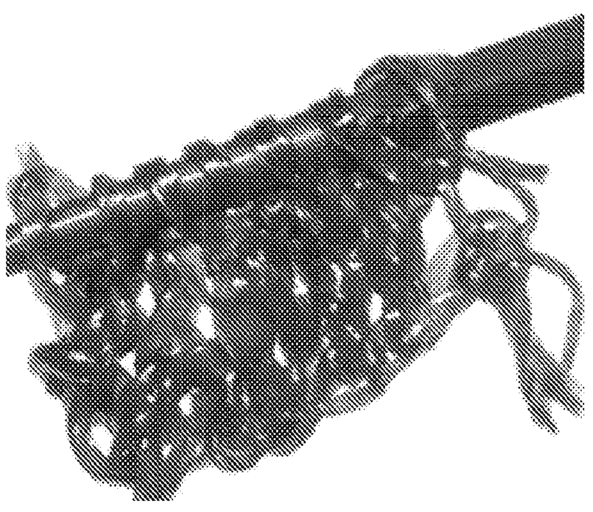
FIG. 5B: A composite protein fiber containing red and blue fluorescent proteins.
Figure 6A:
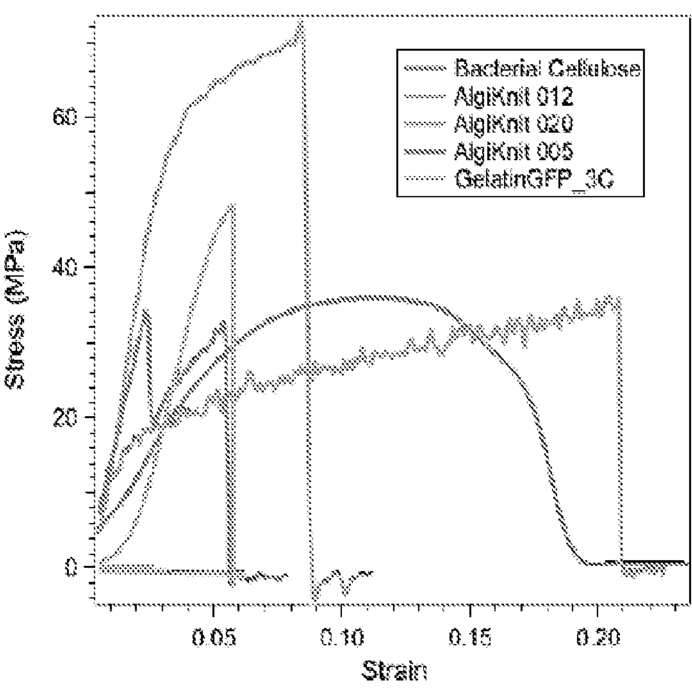
FIG. 6A: Tensile testing of GFP:gelatin compared to Algiknit and bacterial cellulose.
Figure 6B:
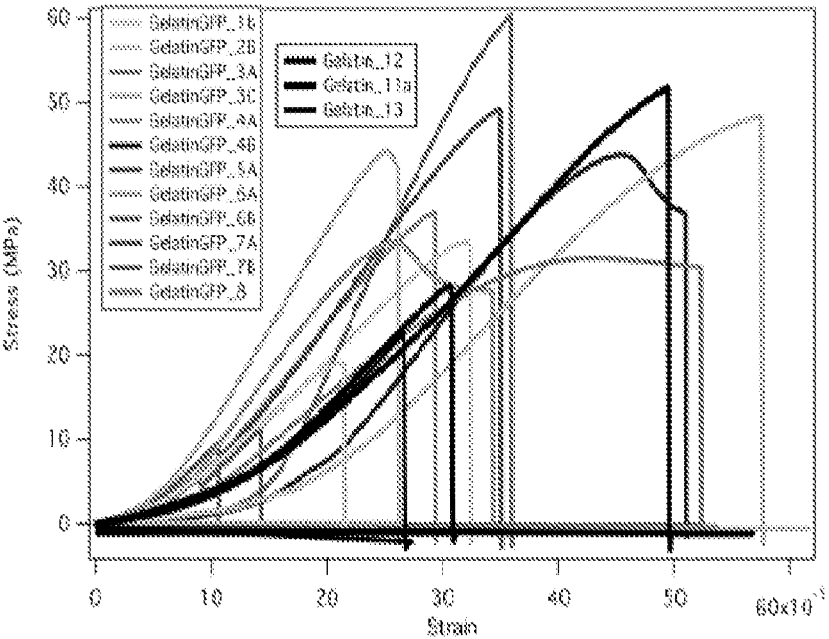
FIG. 6B: Tensile testing for n=12 GFP:gelatin fibers (color curves) showing inconsistencies across samples due to limited extrusion profile control.

It was first established that GFP and gelatin proteins are capable of enzymatic cross-linking to form a fiber that maintains the fluorescent properties of GFP, as shown in FIG. 5A for example. However, a lack of control over extrusion profiles introduced significant variation into mechanical properties based on tensile testing data, as shown in FIG. 6A and FIG. 6B. Here, uncertainties introduced by multiple parameters in the fiber extrusion process were reduced by casting films to assess the effects of the GFP:gelatin ratio and the transglutaminase have on cross-linking and mechanical properties.

Materials and Methods

Protein Composite Fiber Extrusion and Film Casting

Because gelatin forms a solid gel below room temperature, intact fibers can be extruded into a chilled (<10 C) bath while maintaining their structure via physical crosslinks. To form chemical crosslinks that maintain fiber structure at room temperature and warmer, the lysine/glutamine reactive enzyme transglutaminase (TG) can be dissolved in the chilled bath, where it can form covalent bonds between gelatin polymer chains to produce fibers.

Fiber Extrusion

Fibers were formed by extruding gelatin-GFP composite dopes with gelatin percent concentrations ranging from 10-20% and gelatin:GFP ratios between 115:1 and 400:1 in PBS, followed by 1 hr crosslinking using 1% transglutaminase in a chilled buffer bath (100 ml). Successful fiber formation with gelatin, GFP and transglutaminase was recorded using the following protocol:

1% TG bath was prepared using 1000 mg TG and 100 ml PBS buffer. The protein hydrogel "dope" was prepared as follows:

1. Mix 3 ml GFP+2 ml PBS in a 50 ml Falcon tube.
2. Add 1000 mg gelatin to the solution and vortex to mix.
3. Heat at 50 C to eliminate bubbles and bring solution to a temperature to achieve requisite viscosity to draw dope into syringe.
4. Fill syringe with dope and return to oven with the tip up to eliminate air bubbles (~2 mins).
5. Dope was cooled to approximately room temperature in a syringe, and fibers were mechanically extruded a rate of 1.75 ml/min using a 1 ml BD plastic tip submerged into a 50 ml coagulation bath cooled on ice to 12C. Preliminary extrusion utilized a moving tray, however a variable speed motor for fiber uptake/winding that enables a stationary bath has also been used successfully.

6. Fibers were incubated to enzymatically cross-link in a coagulation bath for at least 1 hour, removed, and dried on teflon covered foil tray in ambient conditions.

Film/Gel Casting

Figure 7:
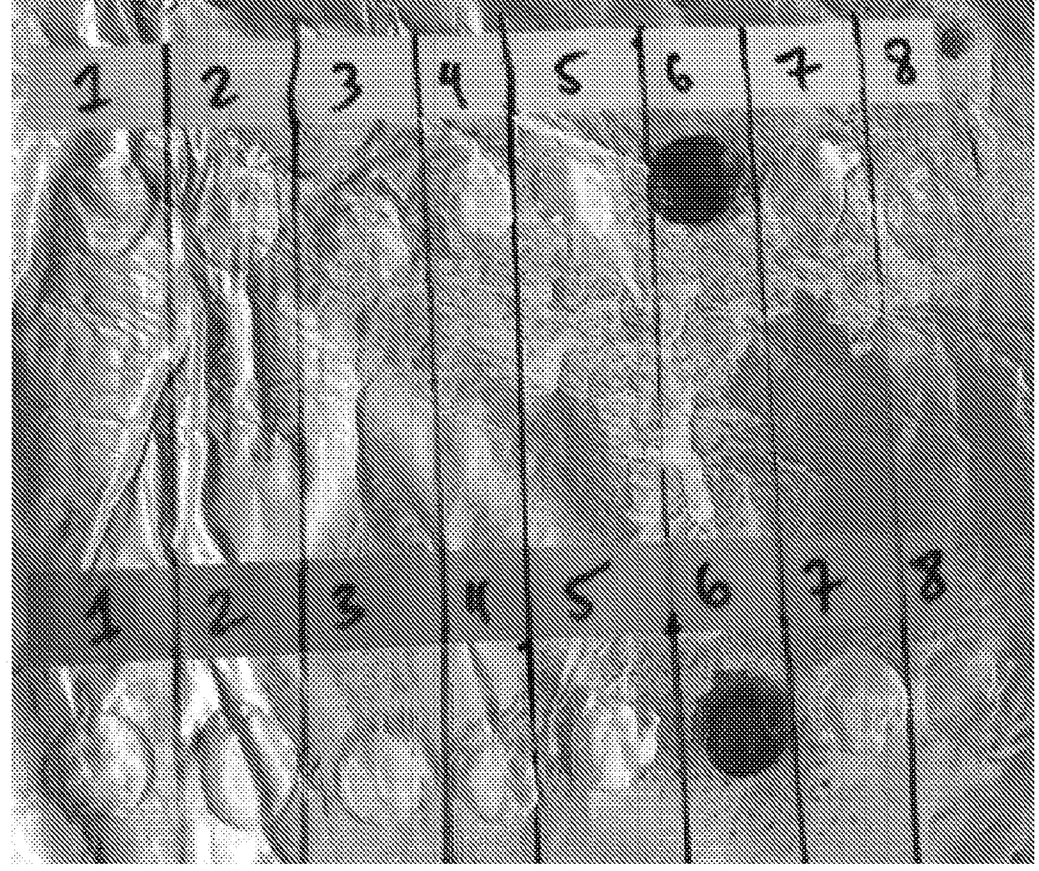
FIG. 7: GFP:gelatin and RFP:gelatin 2 cm diameter films cast in transglutaminase as per concentrations listed in Table 1 and Table 2.
Figure 8:
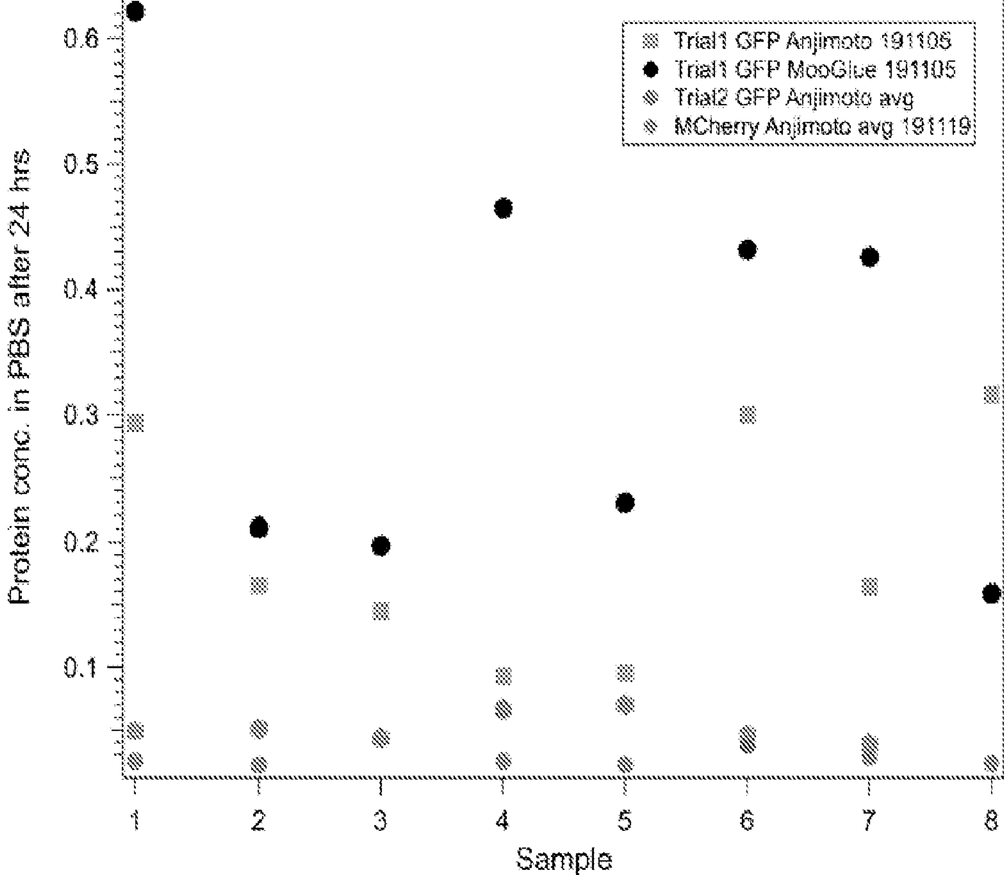
FIG. 8: Protein concentration in PBS solution after a 24 our soak of films of GFP+gelatin cast in a transglutaminase bath for different sources of transglutaminase for GFP: gelatin ratios shown in Table 1 (Group A—MooGlue) and Table 2 (Group B—Anjimoto). Trial 2 represents the average of n=3 films cast in the ratios indicated in Table 2. Lower protein concentrations in the PBS solution indicate a higher degree of cross-linking in the films.
Figure 9A:
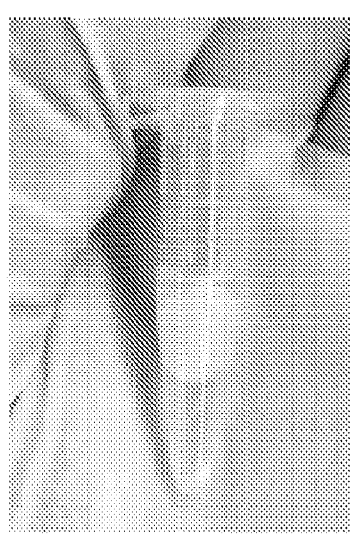
FIG. 9A: Purified bacterial nanocellulose (BNC) pellicle submerged in 1.57 mL of a GFP solution with a concentration of 3.19 mg/ml.
Figure 9B:
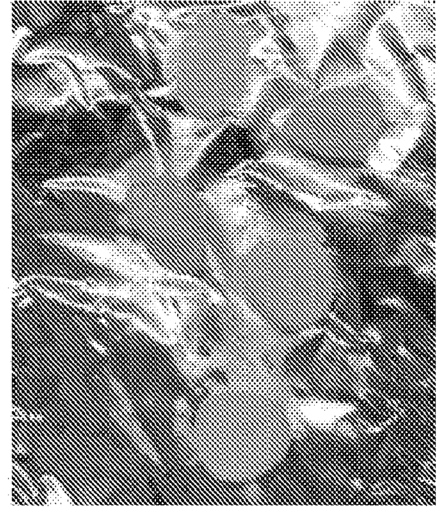
FIG. 9B: GFP-treated BNC pellicles removed from the solution after 24 hours. Color is retained after samples are rinsed and immersed in PBS solution for 24 hours.
Figure 10A:
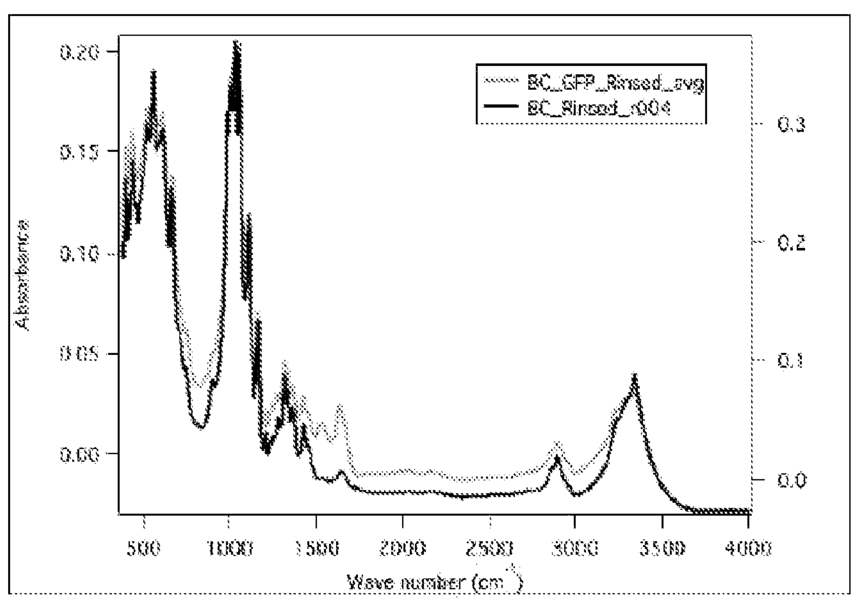
FIG. 10A: FTIR spectra of bacterial cellulose (BC, black curve) and BC/GFP composites (green curve).
Figure 10B:
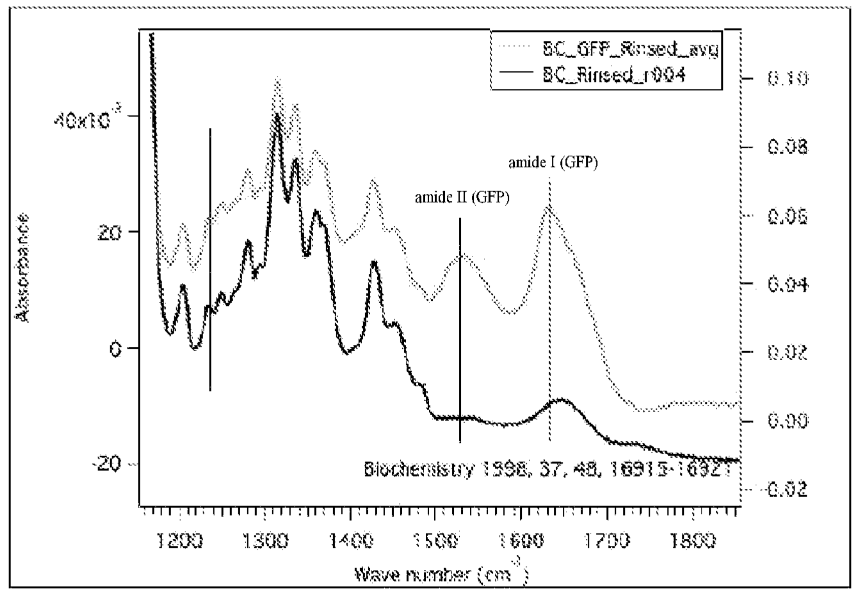
FIG. 10B: A zoomed in portion of the FTIR spectra shown in FIG. 10A.

Inconsistencies between fibers extruded as above (length, kinks, diameter, beading) introduce uncertainties to tensile testing data. To address the effects of GFP:gelatin ratios, as shown in Table 3 regarding crosslinking density and mechanical properties of the protein composites, 2 cm diameter films were cast as shown in FIG. 7. Smaller films (2 cm diameter) were cast to minimize mass diffusion limitations on cross-linking throughout the bulk of larger films. The following method was used:

1. Combine fluorescent proteins and PBS according to amounts in Table 3 in a 1.5 ml Eppendorf tube, add gelatin according to amounts in Table 3, and vortex each solution immediately to ensure a uniform solution. Heat tubes in oven at 50 C for 15 minutes, or until gelatin mixture has the requisite viscosity to draw up into a (18 g) syringe.
2. Chill 1% TG bath on ice until it reaches no higher than 14 C (lower temperatures are also acceptable). Pipette 200 microliters of the TG bath into the appropriate number of wells of a 96 well plate and leave on ice.
3. Dispense protein mixture ("dope") into each well of the plate until full. Note that dope begins to gel immediately. Using a labeled 6-well plate, place one 2 cm rubber ring in each well, and divide mixture evenly among rings, let the gel cool for five minutes.
4. Add transglutaminase bath to each well to cover solution
5. Cover plate and incubate overnight in 4C to crosslink.
6. Remove from the refrigerator and place on Teflon covered foil to dry under ambient conditions.

As an additional note to this protocol, ensure that the gelatin mixture does not have air bubbles in the syringe before expelling into rubber rings. Place syringe with the tip up in the oven until air bubbles float to the top of the syringe, expel, then continue to fill rings.

For SEM samples, 4.5 mm skin biopsy punch to make samples were used.

For mechanical testing, the length of the sample is at least three times the width in a rectangular/bone shape.

Protein Composite Fiber Extrusion and Film Casting

Two study groups were evaluated in this experiment, Group A (Moo Glue) and Group B (Activa by Anjimoto), to investigate potential differences in the crosslinking mechanics.

The protein ranges outlined in Table 3 (Group A) and Table 4 (Group B) targets keeping the concentration of gelatin at a constant 20%. Note that the gelatin concentration affects viscosity of the composition and thereby fiber extrusion capacity. Because the GFP in solution is dilute, a 0.5 mL of GFP solution has been utilized to achieve a 1.75 mg target, and accordingly at least 100 mg of gelatin is used in order to stay at or above the 20% target in this example.

GFP Concentrations and Protocol for Sample Groups

GFP solution with a concentration of 3.495 mg/mL was used for this test. In previous tests, fibers have been successfully extruded using 20% gelatin and 0.15% GFP in 1 mL of PBS.

1. Combine target GFP volume with target PBS volume as described in Table 3.
2. Weigh out and dissolve the target amount of gelatin in each solution. Mix in 1 ml Eppendorf tubes, vortex to combine, and place in incubator at 50 C for 20 minutes to aid in mixing.
3. 1% transglutaminase bath in two formulations were prepared in 150 ml Pyrex Bottles, covered, placed on stir plate for 10 minutes, and then placed in an ice bath to temp 12-14C:
   A) 100 ml DI-H2O+1001.5 mg TG (Moo Glue)
   B) 100 ml DI-H2O+1001 mg TG (Activa)
4. Remove protein gels from the oven and pour directly into 12 well plates filled with approximately 5000 ul of chilled (12-14° C.) transglutaminase coagulation bath. Incubate films in TG bath to crosslink for 1 hour, using tweezers to remove and place on teflon covered foil sheet for two days at room temperature. Coagulation bath is saved to read protein concentration and evaluate cross-linking.
5. Place dried films in 2000 ul of DI water.

Results

Effects of GFP:Gelatin Ratio and Transglutaminase on Cross-Linking of Protein Composite Gels

TABLE 3

| Group A - Moo Glue Coagulation Bath | | | | | | | |
|---|---|---|---|---|---|---|---|
| Study Group | GFP (mL) | GFP conc. (mg) | Gelatin (mg) | Gelatin:GFP | PBS (mL) | Protein Conc. PBS (mg/ml) | Crosslinked (Y/N) |
| 1 | 0.5 | 1.75 | 201.9 | 115:1 | 0.5 | 0.622 | Y |
| 2 | 0.5 | 1.75 | 174.8 | 100:1 | 0.375 | 0.211 | Y |
| 3 | 0.5 | 1.75 | 150.2 | 86:1 | 0.25 | 0.197 | Y |
| 4 | 0.5 | 1.75 | 125.3 | 72:1 | 0.125 | 0.465 | Y |
| 5 | 0.5 | 1.75 | 100 | 57:1 | 0 | 0.230 | Y |
| 6 (RFP) | 0.5 | Tube A | 176.6 | TBD | 0.375 | 0.432 | Y |
| 7 | 2.5 | 1.75 | 251.8 | 144:1 | 0.5 | 0.426 | Y |
| 8 | 3.5 | 1.75 | 299.7 | 171:1 | 0.5 | 0.159 | Y |

TABLE 4

| Group B - Anjimoto Activa Enzyme Bath | | | | | | | |
|---|---|---|---|---|---|---|---|
| Study Group | GFP (mL) | GFP conc. (mg) | Gelatin (mg) | Gelatin:GFP | PBS (mL) | Protein Conc. PBS (mg/ml) | Crosslinked? Y/N |
| 1 | 0.5 | 1.75 | 201 | 115:1 | 0.5 | 0.294 | Y |
| 2 | 0.5 | 1.75 | 176.5 | 101:1 | 0.375 | 0.166 | Y |
| 3 | 0.5 | 1.75 | 151.6 | 87:1 | 0.25 | 0.145 | Y |
| 4 | 0.5 | 1.75 | 124.8 | 71:1 | 0.125 | 0.093 | Y |
| 5 | 0.5 | 1.75 | 101.6 | 58:1 | 0 | 0.096 | Y |
| 6 (RFP) | 0.5 | Tube A | 175.1 | TBD | 0.375 | 0.300 | Y |
| 7 | 0.5 | 1.75 | 251.6 | 144:1 | 0.5 | 0.165 | Y |
| 8 | 0.5 | 1.75 | 300.1 | 171:1 | 0.5 | 0.316 | Y |

Example 3: Modification of Bacterial Nanocellulose with a Fluorescent Protein Materials and Methods A. Bacterial Nanocellulose (BNC) Biosynthesis A protocol for preparing BNC nanofibers is as follows. To reduce the environmental impacts of using cane sugar, extracted sugar from spent malt from brewery waste has been utilized by running hot water through the malt until desired sugar concentration is measured.

In a 1000 ml beaker:

1. Brew 2-3 bags of green tea to hot water.
2. Dissolve 58 grams of sugar.
3. Wait for solution to return to room temperature.
4. Add a small piece of SCOBY (symbiotic culture of bacteria and yeast) to the liquid culture media.
5. Add 10% starter culture (100 mL) or kombucha to the solution.
6. Cover beaker with cheese stocking treated with ethanol to prevent contamination.
7. Incubate static culture for 7 days.
8. Remove microbial cellulose pellicle from culture.
9. Continue static culture for more cellulose pellicles.

B. Microbial Cellulose Pellicle Purification

A. Immerse pellicle in $DiH_2O$ at 90° C. for 2 hours.

B. Place in a 0.5 M aqueous solution of NaOH at room temperature for 24 hours to lyse attached bacterial cells (0.5 M NaOH→1 g in 50 mL DiH2O).

C. Repeatedly wash pellicles in $DiH_2O$ to remove alkali and return to a pH of 7.0.

D. If storing, place pellicles in $DiH_2O$ at 4° C. to prevent dehydration.

C. Impregnation BNC with GFP

After biosynthesis and purification of BNC pellicles, conditions to impregnate BNC with GFP/RFP proteins were determined, which included coating and soaking the bacterial cellulose in/with GFP/RFP and testing the crosslinking by placing crosslinked samples in PBS.

Using transglutaminase and GFP concentrations indicated in Table 5, submerge (n=5) purified BNC pellicles in GFP/RFP for 24 hours (keep at least n=3 purified BNC pellicles as reference samples for FTIR). As BNC pellicle is likely to lay flat on the surface, be sure to flip for homogeneous coating.

TABLE 5

| Transglutaminase and GFP concentrations in F4 mechanical testing protocol | | | | | |
|---|---|---|---|---|---|
| Formulation | GFP amount (mg) | [GFP Stock] (mg/mL) | GFP Vol to added (mL) | Transglutaminase solution | Total Volume |
| F4 | 5.00 | 3.19 | 1.5674 | 1% wt | Enough for BNC pellicle to be fully submerged |

D. Simple Cross-Linking Test (n=3)

Place at least three (3) samples in PBS for 24 hours, then measure protein concentration in the solution.

E. Fourier Transform Infrared Spectroscopy (FTIR)

Assess chemical conformational characteristics of microbial cellulose biofilms (bonding/interaction between BNC and GFP/RFP) with Fourier transform infrared (FTIR) spectroscopy (LUMOS, Bruker). Collect spectra in attenuated total reflectance (ATR) mode from 600-4000 $cm^{-1}$ using 200 scans with a resolution of 4 $cm^{-1}$. For each biofilm, examine at least three samples of the same conditions (purified BNC and purified/coated GFP/BNC). For comparison, measure unpurified, as grown BNC.

Results

GFP-BC Composites

GFP was successfully immobilized into BNC nanofiber meshes. No color change was observed after the GFP-BNC pellicles were submerged in PBS solution for 24 hours, consistent with a chemical interaction between the GFP and BNC. Measurement of protein concentration in the PBS after the soak confirms this observation.

GFP did not fall into solution after a 24-hour immersion in PBS, indicating an interaction (e.g. van der Waals, hydrogen bonding, or electrostatic) between the protein and polysaccharide. This interaction enables GFP to be immobilized in matrix of BNC nanofibers, as evidenced by the color change of the nanofibers.

Due to the thickness of BNC and low concentration of GFP, major differences due to immobilization of GFP on BNC are not observed. However, new peaks at 1531 $cm^{-1}$ and 1634 $cm^{-1}$ appear for the GFP/BNC sample, which can be assigned to the amide I and amide II of GFP, respectively.

The emergence of new absorption peaks suggests a chemical interaction between GFP and BNC. The subtlety of the changes and lack of a shift in peak position is likely due to the thickness of the BNC samples. If the GFP is simply immobilized in the biofilm, it is expected that the protein significantly leaks into solution after a few hours or less.

EXPERIMENTAL DETAILS—SECOND SET

Overview

Inspired by the inherent aesthetic and performance properties of proteins found in nature, functional proteins have been engineered and green chemistry has been utilized to create biodegradable textile fibers with a desired trait, such as color. The technology has enabled creation of fibers with a range of inherent colors (e.g. red, purple, blue, and green) and natural fluorescence, attributed to protein structure, retained through fiber processing. This proof of concept may be expanded to engineer fibers with performance traits such as moisture management, antimicrobial properties, and UV protection, suitable for industrial spinning processes.

The fiber development platform described herein spans across three main areas of research: biotechnology/protein design, green chemistry/material science, and textile development. This platform is used to develop scalable solutions that impact the textile industry at scale, while employing use of low impact nutrient media, rapidly renewable and compostable feedstocks for fibers with desired properties attributed to protein shape, and a fiber formation process that can fit into existing fiber production infrastructure.

This disclosure also demonstrates the efficacy of enzymatically cross-linking proteins and protein-cellulose composites, and the ability to create fibers with a desired property, such as color, provided by low concentrations of recombinant proteins. Additionally, culture media nutrients for biosynthesis, as well as biopolymer feedstocks, may also be derived from waste streams, which lowers the environmental impact and cost of production.

1. Protein Design for Structural Color 1.1 Considerations 1.1.1. Inherent color: The generated biomaterial has a brightness preferably at least 5 $mM^{-1}cm^{-1}$, defined as the combination of light absorbance (extinction coefficient) and fluorescence quantum yield (ratio of fluorescent photons per absorbed photon), and measured with absorption and emission spectroscopy.

1.1.2. Color stability: Preferably at least 65% of brightness retained after 7-day immersion of biomaterial in aqueous solution, determined by UV-Vis spectroscopy.

1.1.3. Color retention thresholds: textile industry standards for color fastness (AATCC 107-1991/ISO 105 E01).

Figure 13A:
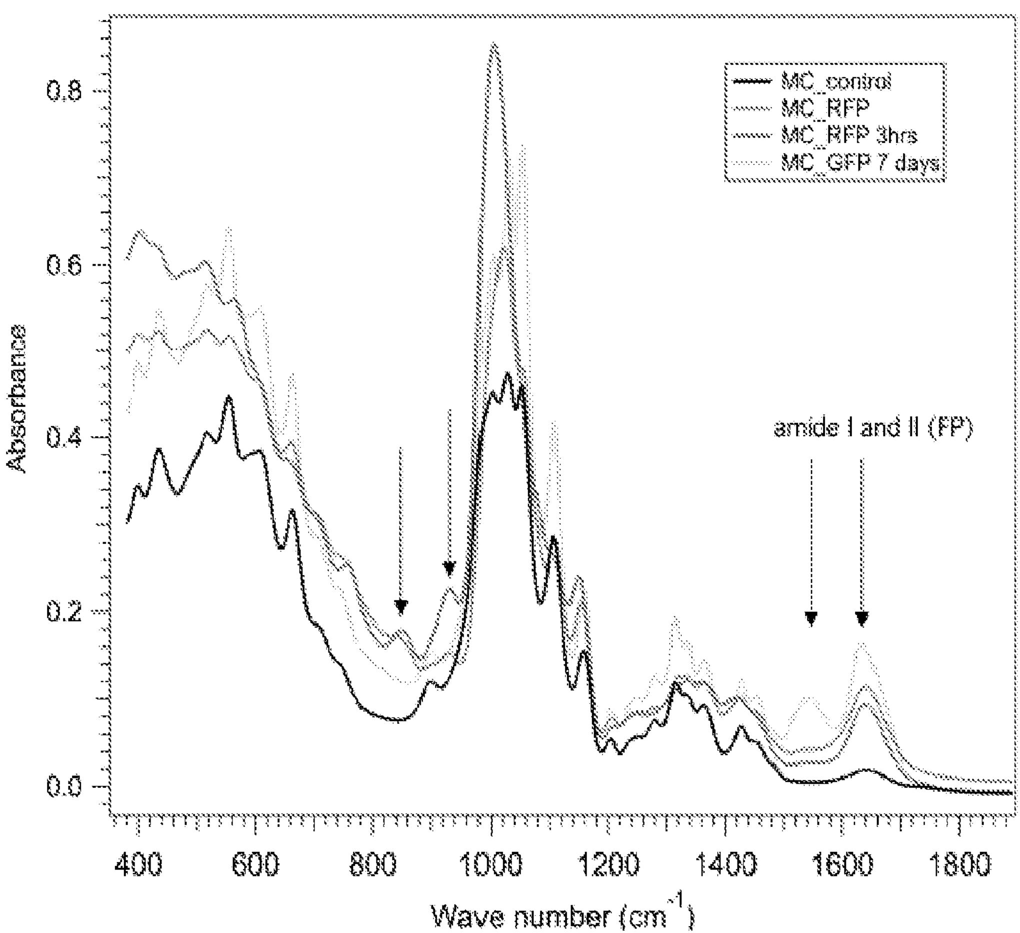
FIGS. 13A-13D: Inherent color (protein structure and function) retained in biofilm (FIG. 1A) and fibers (FIG. 1B).
Figure 13B:
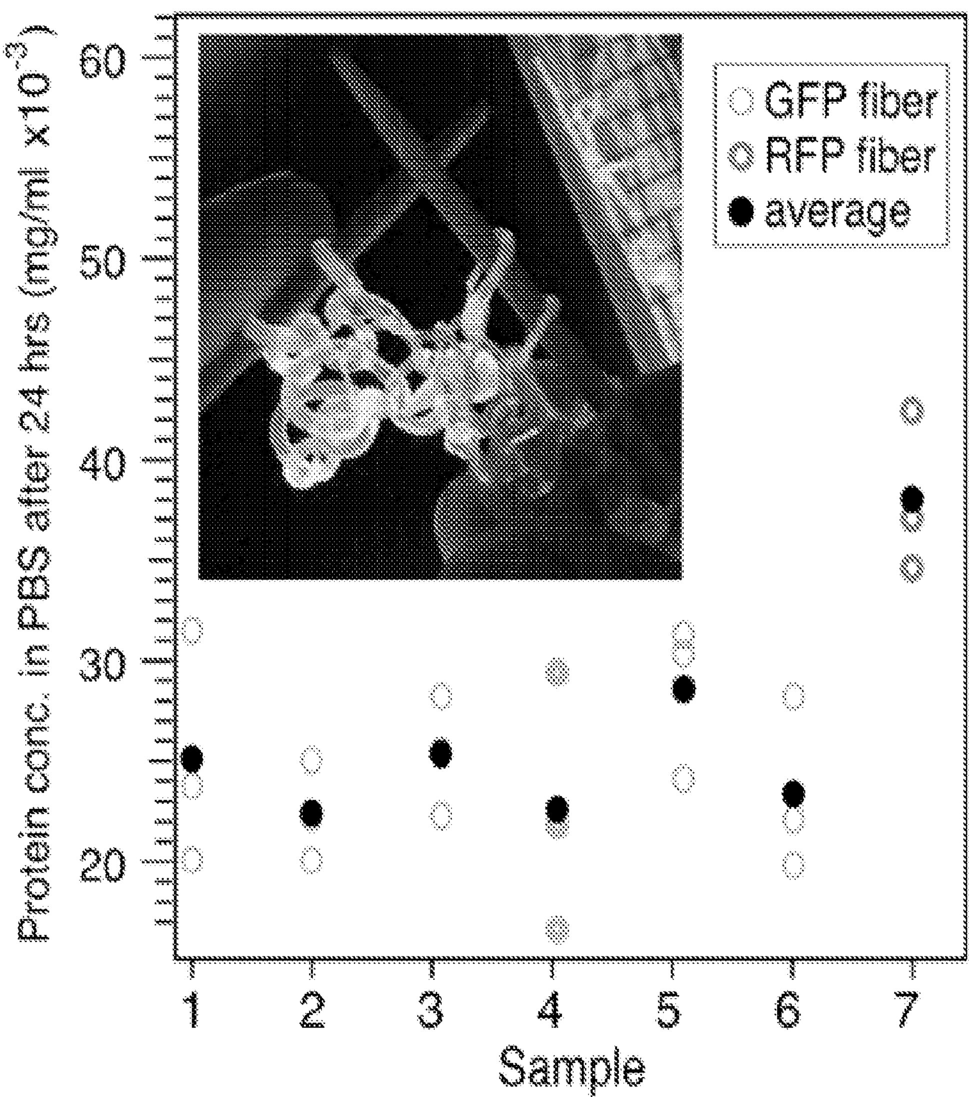

1.2 Milestones Reached 1.2.1. Inherent color (protein structure and function) retained in biopolymer film (FIG. 13A) and fiber form (FIG. 13B).

1.2.2. Color stability of fibers in aqueous environment after 24 hrs (FIG. 13B).

Figure 13C:
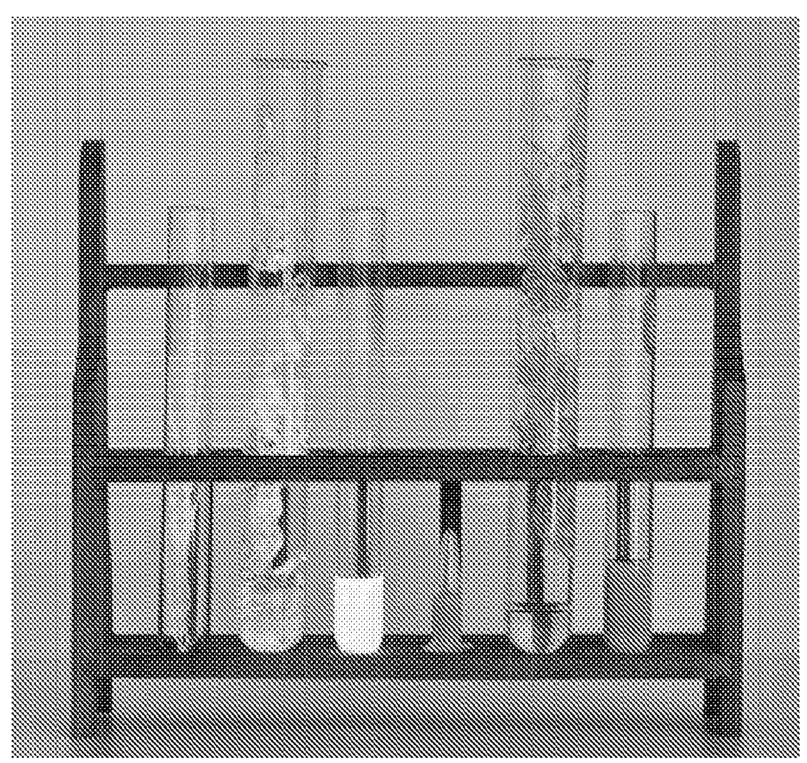
Figure 13D:
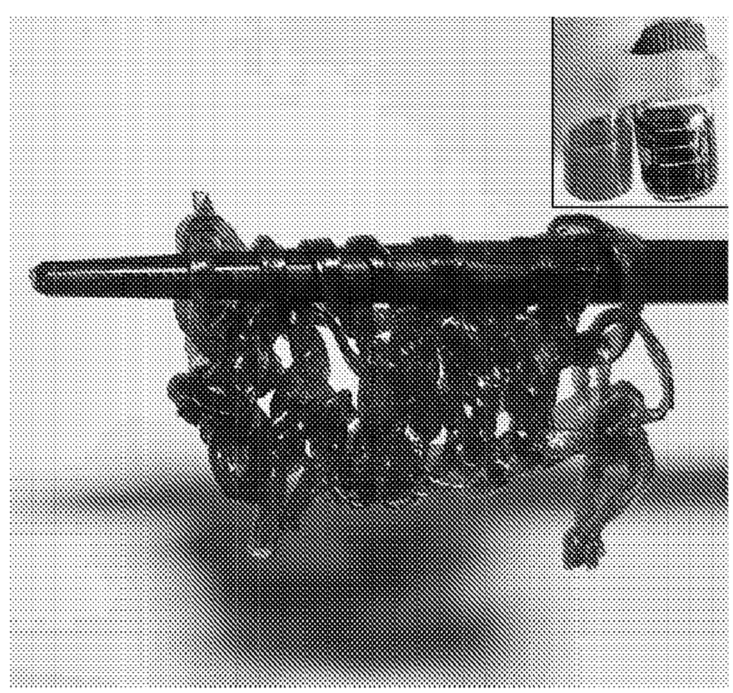

1.2.3. UV protection provided by a red fluorescent utilized to incorporate a UV-sensitive blue fluorescent protein, resulting in a UV-stable purple fiber (FIG. 13D—purple knit swatch).

1.2.4. Designed proteins for expanded color offering including red, pink, blue, purple and green proteins: Red Fluorescent Protein (RFP), mScarlet, and GFP (FIG. 14E)—photo showing pink and green fibers and colored proteins.

Table 6: Industry standards for color-fastness defined by the American Association of Textile Chemists and Colorists (AATCC)

| Standard | Colorfastness Test and Metric |
|---|---|
| AATCC TM16.1 | Light: Outdoor. 4-5 grade for polyester, fluorescent colors > 3) |
| AATCC TM15 | Perspiration. 4-5 graded (for polyester) to ship to all regions |
| AATCC TM61 | Laundering: Accelerated. Color change rating of 4 and a color staining rating of 3 to 5 for detergent washing. |
| AATCC TM107 | Water. 4-5 grade (for polyester) accepted for shipping to all regions |
| AATCC TM116 | Crocking - Grade 3 and 4 ratings for wet and dry rubbing, respectively |
| AATCC TM119 | Flat Abrasion (Frosting) Warp: 4-5 Weft: 4-5, fluorescent colors > 3 |
| AATCC TM163 | Storage: Dye Transfer |

2. Protein Design for Fiber Formation 2.1 Considerations

Engineer proteins that preferably self-assemble with minimal chemical intervention to form stable fibers with requisite properties (defined in Section 3: Fiber Formation), evaluated with:

2.1.1. UV-Visible Spectroscopy of protein concentration in the biomaterial as a metric for color uptake and colorfastness as a function of engineered charge on protein.

2.1.2. Protein stability (color) in fiber processing.

2.1.3. Sufficient cross-linking for minimal swell in aqueous solution (preferably <80% after 24 hours).

Figures 14A, 14B:
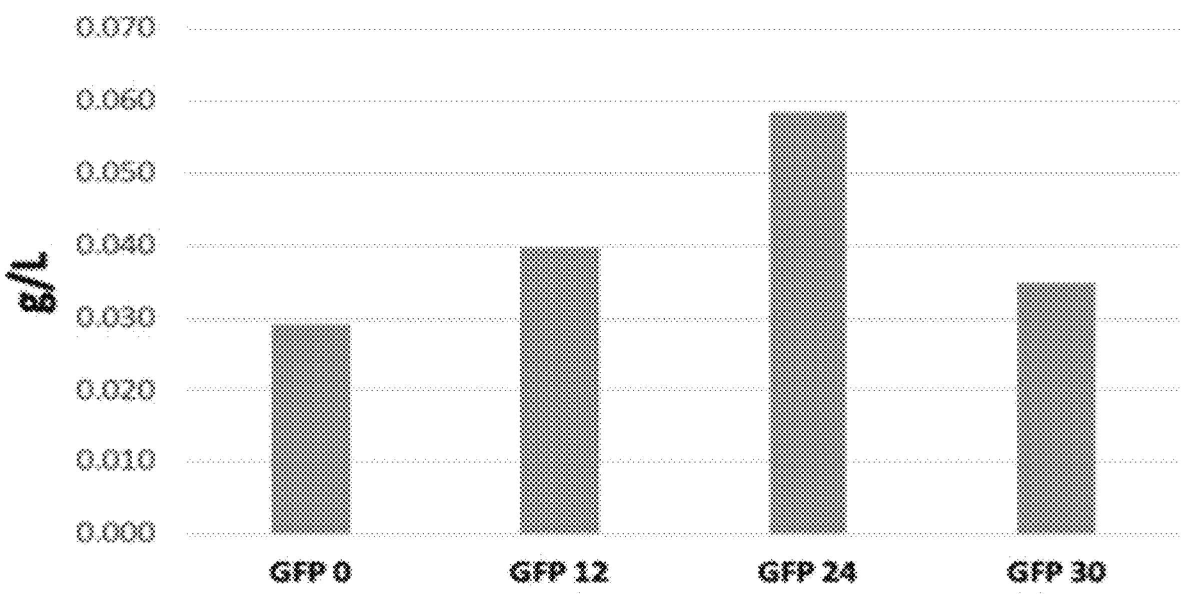
FIGS. 14A-14E: Color uptake and colorfastness as a function of protein charge evaluated as the intensity of fluorescent protein resonance in BNC, including.

2.2 Milestones Reached 2.2.1. Designed green fluorescent proteins with different end groups to evaluate effects of protein charge on color retention (protein function) in a biopolymer composite (FIGS. 14A and 14B).

Figure 14C:
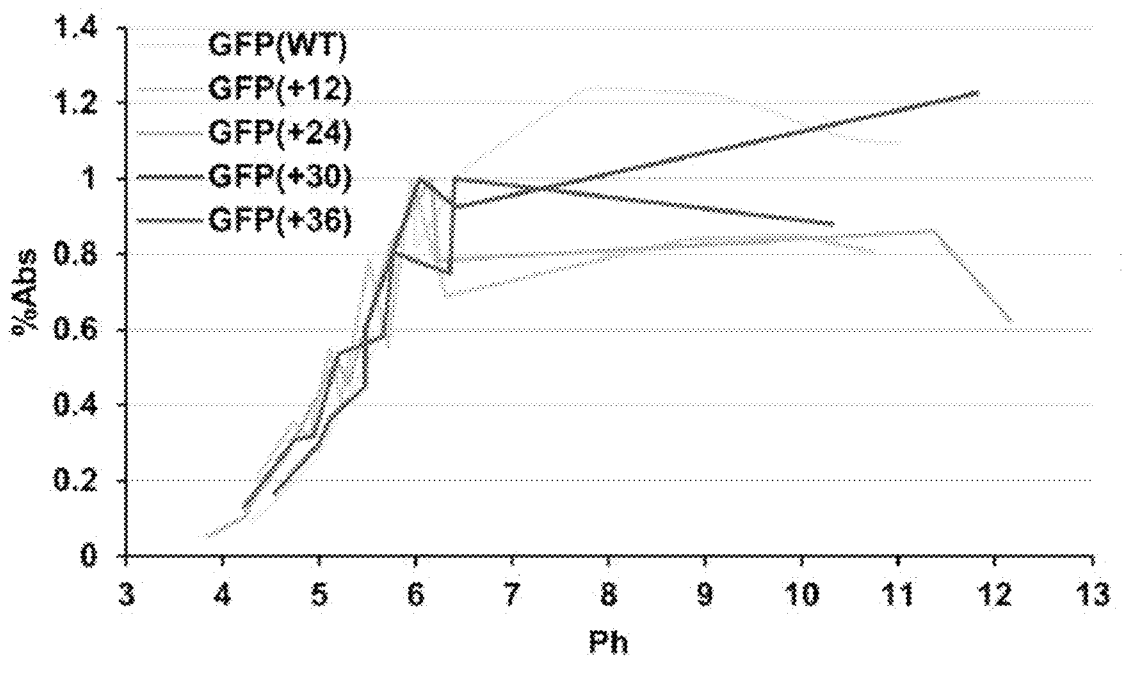
Figure 14D:
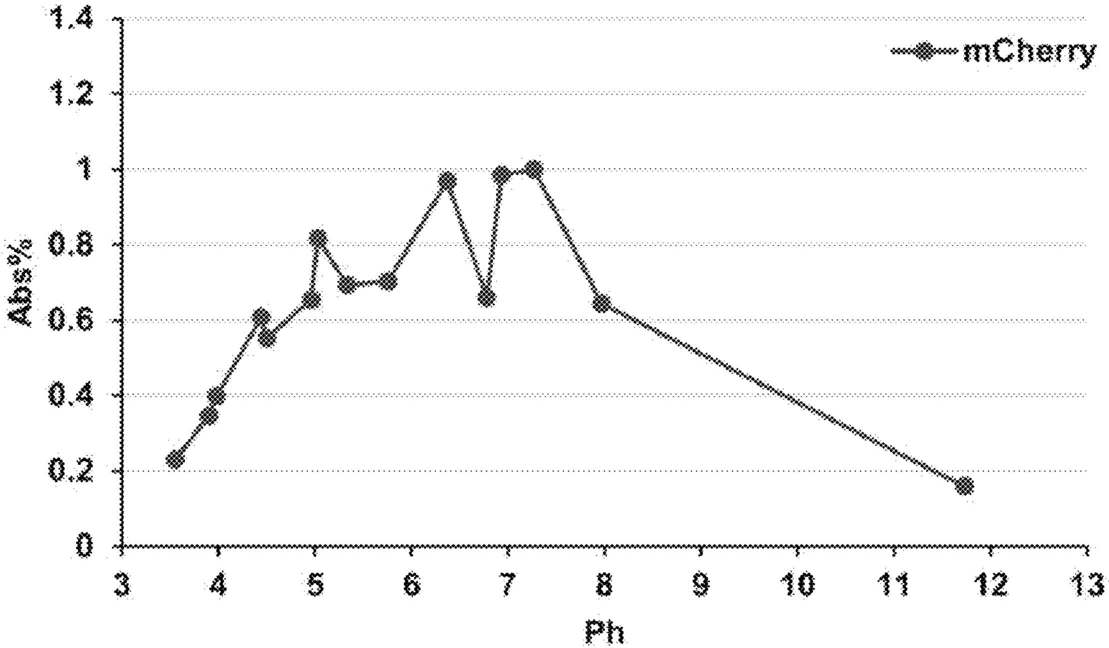
Figure 14E:
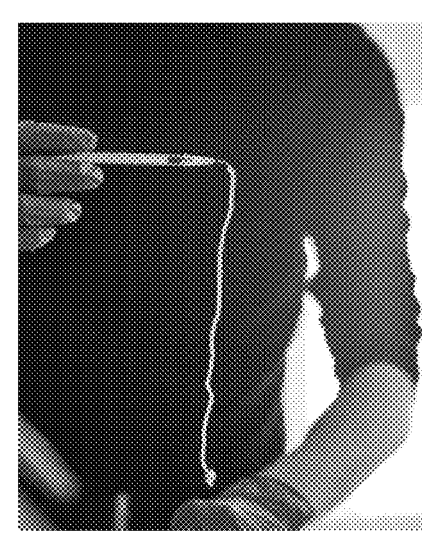
Figure 14E:
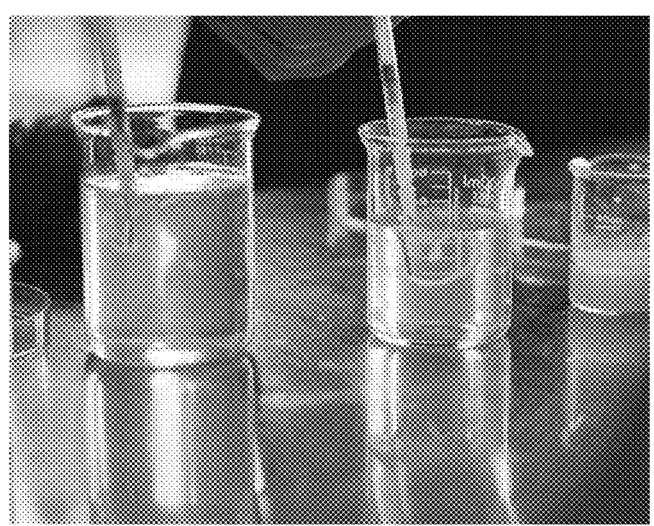
Figure 14E:
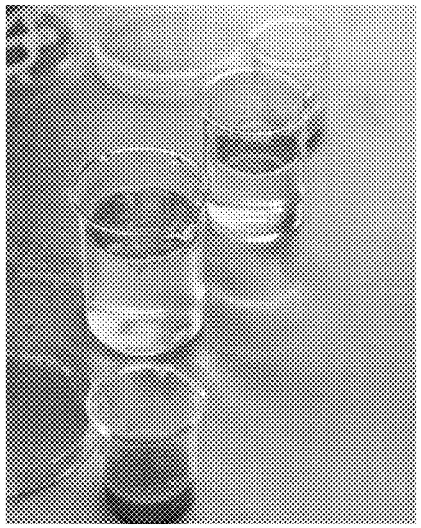
Figure 14E:
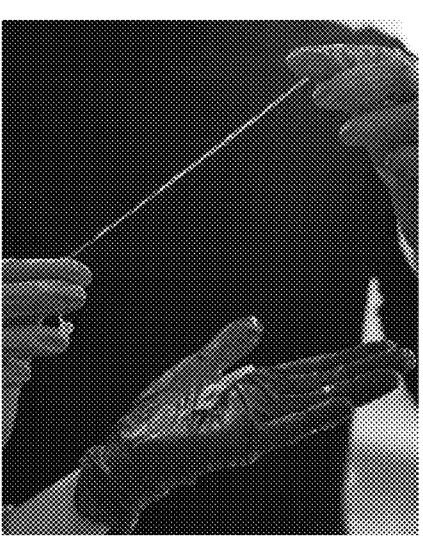

2.2.2. Evaluated pH stability of protein to identity and optimize processing conditions (FIGS. 14C and 14D).

2.3 Additional Tasks 2.3.1. Evaluate a series of proteins for affinity to fiber formation using the biomaterial platform, iterating and optimizing based on color and brightness criteria defined in Section 1.1.

2.3.2. Design binding sites to facilitate self-assembly of proteins into controlled form factors; i.e. fibers with requisite denier and extrusion profiles.

2.3.3. Design protein-based structural performance properties (stretch, moisture management, UV protection.

3. Fiber Formation 3.1 Considerations 3.1.1. Fiber color retention: The generated fibers retain preferably at least 70% of their color at 37° C. after fiber processing. Fiber color may be measured by UV-Vis spectroscopy. This preferred level is based on textile standards for color fastness tests (American Association of Textile Chemists and Colorists, AATCC 107-1991/ISO 105 E01).

3.1.2. Fiber mechanical properties: Preferably about 150 MPa-4 GPa Young's modulus, preferably about 115 MPa maximum tensile strength, and preferably about 6.7% ductility confirmed via, for example, tensile testing with an Instron device.

3.2 Milestones Reached 3.2.1. Mechanism and chemical fingerprints of enzymatic cross-linking of proteins (FIGS. 15A and 15B).

3.2.2. Color stability through green chemistry fiber processing (FIGS. 13B-13D).

3.2.3. Mechanical properties tested and iterated with fiber composition and protein design (FIG. 15C).

3.3 Additional Tasks 3.3.1. Mechanical fiber extrusion and uptake with control over dope flow rate, tension, speed, temperature, and gas flow.

TABLE 7

| 3.3.2. ASTM and AATC textile industry testing standards | |
|---|---|
| | Standard Test Method/Evaluation |
| Wash Wear | |
| ASTM E2274-16 | Evaluation of Laundry Sanitizers and Disinfectants |
| ASTM F732-17 | Wear Testing Polymetric Materials |
| ASTM G89-7 | Wear Testing |
| ASTM D6321/ D6321M-14 | Evaluation of Machine Washable T-Shirts |
| Strength | |
| ASTM DS034-09(2017) | Breaking Strength and Elongation of Textile Fabrics |
| ASTM D3787-16(2020) | Bursting Strength of Textiles-Constant-Rate-of-Traverse (CRT) Ball Burst Test |
| Stretch | |
| ASTM D4964-96(2020 | Tension and Elongation of Elastic Fabrics (Constant-Rate-of-Extension Type Tensile Testing Machine) |
| ASTM D6614/ D6614M-20 | Stretch Properties of Textile Fabrics - CRE Method |
| Abrasion/Durability | |
| ASTM D4966-12(2016) | Abrasion Resistance of Textile Fabrics (Martindale Abrasion Tester Method |
| ASTM D4157-13(2017) | Abrasion Resistance of Textile Fabrics (Oscillatory Cylinder Method) |
| ASTM D3744/ D3744M-18 | Aggregate Durability Index |

4. Diversity Fiber Feedstock 4.1 Considerations 4.1.1. Identify scalable, high volume/rapidly renewable, low-cost feedstock for biomaterial fibers (using, for example, cost/kg of polyester as a benchmark).

4.1.2. Biomaterial fibers preferably demonstrate requisite mechanical properties and color brightness (defined in Sections 1.1 and 3.1, respectively).

4.1.3. Biomaterial fibers are preferably biodegradable in natural terrestrial and aquatic environments. Example metrics:

DIN EN ISO 11721-1: Textiles—Determination of resistance of cellulose containing textiles to micro-organisms.

Soil burial test—textile mass lost. Examination of the decay process of a product by micro-organisms like fungi and bacteria in combination with oxygen in the soil.

4.1.4. Confirm biodegradation products are non-cytotoxic and non-cytogenetic; i.e. biomaterial fibers are preferably compostable. Cress and earthworm tests may be used to assess the impact on the environment and the ecotoxicological safety of the biotextile.

4.2 Milestones Reached 4.2.1. Utilized a range of proteins and polysaccharide composites for the biomaterial fibers, including gelatin (FIG. 1A-D), bacterial nanocellulose (BNC) (FIGS. 14A, 14B and 15C), protein-polysaccharide blends (FIG. 14E), and soy protein isolate (SPI) and its primary globular subunits (FIGS. 15A and 15B).

4.2.2. Molecular level analysis of efficacy of enzymatic linking for different proteins (FIGS. 16-16C and FIGS. 17A-17D, 18A-18F, 19A-19D, and 20A-20F).

4.2.3. Glycerol modifies the bonding in SPI, observed as an enhanced C—O stretch peak area for as-fabricated and vacuum dehydrated SPI films at pH 3, 5, 7, and 10, both with and without inclusion of transglutaminase (FIGS. 18A-18F and FIGS. 20A-20F).

4.3 Additional Tasks 4.3.1. Further expand repertoire of biopolymer feedstocks to enable systematic cost-benefit analysis.

5. Supplementary Data 5.1 Experiments

Soy protein isolate treated with 0.1 M NaOH, and subsequently adjusted to pH 3, 5, 7, or 10, respectively, with citric acid, with and without 10% v/v glycerol treatment and 1% w/w TG treatment.

FIGS. 19A-19D: FTIR peak integration (n=3) for as fabricated SPI films.

FIGS. 18A-18F: FTIR peak analysis (n=3) for as fabricated SPI films.

FIGS. 19A-19D: FTIR integration (n=3) for SPI films after vacuum dehydration at 25° C.

FIGS. 20A-20F: FTIR peak analysis (n=3) for SPI films after vacuum dehydration at 25° C.

5.2 Summary of Main Results for Cross-Linking of SPI 5.2.1 Bonding Mechanism

Transglutaminase (TG) causes amine groups ($NH_2$) to react with each other, forming ammonia ($NH_3$, off-gassed) and NH which crosslinks to form amides (NH—C═O).

7S—exhibited strong bond changes in TG bath due to its linear structure, in which there is less steric hindrance.

11S—optimal crosslinking raw material by physical observation, chemical analysis, and swell tests to date.

5.2.3 Structural Differences 7S crosslinks through its linear structure (observed via amide III shift), whereas SPI and 11S are aromatic.

5.2.4 FTIR Chemical Fingerprints

Amine stretch/amide II (NH): No NH bonds form in SPI with TG treatment.

7S forms NH bonds in TG bath and less so in TG dope, whereas 11S only forms NH bonds when in TG dope.

Amine stretch/amide I (C═O): No C═O bonds form in SPI with TG treatment. 7S form C═O bonds in TG bath and less so in TG dope, whereas 11S only forms C═O bonds when in TG dope.

Standard Methods

Standard methods in molecular biology are described Sambrook, Fritsch and Maniatis (1982 & 1989 2nd Edition, 2001 3rd Edition) *Molecular Cloning, A Laboratory Manual*, Cold Spring Harbor Laboratory Press, Cold Spring Harbor, NY; Sambrook and Russell (2001) *Molecular Cloning,* 3rd ed., Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp.

16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Miscellaneous

All references cited herein are incorporated by reference to the same extent as if each individual publication, database entry (e.g. Genbank sequences or GeneID entries), patent application, or patent, was specifically and individually indicated to be incorporated by reference in its entirety, for all purposes. This statement of incorporation by reference is intended, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

While the invention has been particularly shown and described with reference to various embodiments, it will be understood by persons skilled in the relevant art that various changes in form and details can be made therein without departing from the spirit and scope of the invention.

What is claimed is:

1. A method for generating a biotextile material comprising:

(a) obtaining a biopolymer composition comprising (i) a purified, recombinantly expressed protein, the recombinantly expressed protein having been expressed from a DNA coding sequence of a source protein selected from the group consisting of a fluorescent protein, elastin, or pelovaterin, and (ii) at least one of a gelatin, cellulose, or polysaccharide;

(b) exposing the composition to a transglutaminase curing bath maintained at a temperature of 25° C. or lower to enzymatically crosslink the recombinantly expressed protein to at least another unit of the recombinantly expressed protein or the gelatin, cellulose, or polysaccharide of the biopolymer composition; and (c) generating a biotextile material based on the cross-linked composition, the biotextile material exhibiting a functional characteristic associated with the recombinantly expressed protein.

2. The method according to claim 1, wherein the DNA coding sequence is modified to include at least one tag sequence that enhances the crosslinking capacity of the recombinantly expressed protein.

3. The method according to claim 1, wherein the source protein is a green fluorescent protein (GFP), a red fluorescent protein (RFP), a near-infrared fluorescent protein, or a blue fluorescent protein (BFP).

4. The method of claim 1, wherein the transglutaminase to which the composition is exposed is at a concentration of 0.01% to 15% per unit volume of the composition.

5. The method of claim 1, further comprising:

extruding fiber by using the crosslinked composition, wherein the fiber is extruded at rate of 1.75-2.0 ml per minute, and/or wherein constant tension is applied to the fiber during extrusion.

6. A method for generating a biotextile material comprising:

(a) obtaining a biopolymer composition comprising (i) a purified source protein, wherein the source protein is at least one of elastin, pelovaterin, a fluorescent protein, or soy protein isolate, and (ii) at least one of a gelatin, cellulose, or polysaccharide, and wherein the biopolymer composition is obtained in a solution having a pH between 3 and 10;

(b) crosslinking a molecule of the purified source protein to at least another molecule of the purified source protein or the gelatin, cellulose, or polysaccharide of the biopolymer composition by exposing the composition to a crosslinking enzyme and/or a solution comprising calcium chloride; and (c) generating a biotextile material based on the cross-linked composition, the biotextile material exhibiting a functional characteristic associated with the purified source protein.

7. The method of claim 6, wherein the source protein is a recombinantly expressed protein, and the recombinantly expressed protein is expressed from a DNA coding sequence of the source protein.

8. The method of claim 7, further comprising modifying the DNA coding sequence of the source protein to include at least one tag sequence that enhances a crosslinking capacity of the recombinantly expressed protein.

9. The method of claim 6, further comprising exposing the biopolymer composition obtained in (a) to a glycerol solution, wherein a concentration of glycerol in the solution is 0.1% to 10% v/v.

10. The method of claim 6, further comprising exposing the biopolymer composition obtained in (a) to a glycerol solution, wherein the biopolymer composition obtained in (a) comprises a soy protein isolate, and wherein the crosslinking is performed in (b) by exposing the composition to transglutaminase.

11. The method of claim 1, wherein the cellulose is methyl-cellulose or microbial nanocellulose.

12. The method of claim 1, wherein the transglutaminase curing bath has a pH in the range of 5.6-8.8.

13. The method of claim 1, wherein the composition is exposed to the transglutaminase curing bath for at least 15 minutes.

14. The method of claim 1, wherein in the composition, a ratio of the recombinantly expressed protein to the transglutaminase is in a range from 1:1 to 300:1.

15. The method of claim 1, wherein a concentration of the recombinantly expressed protein in the composition is 0.1%-0.2% per unit volume.

16. The method of claim 1, wherein the biopolymer composition obtained in (a) is in solution and an amount of the recombinantly expressed protein in the solution is in a range from 0.84 mg/ml to 3.495 mg/ml.

17. The method of claim 1, wherein the gelatin in the composition is at least 20% of the composition.

18. The method of claim 1, wherein the recombinantly expressed protein to the gelatin ratio is at least 1:1000 by mass; or wherein the cellulose is microbial nanocellulose and the recombinantly expressed protein to the microbial nanocellulose ratio is at least 1:1000 by mass.

* * * * *